United States Patent
Rosin-Arbesfeld et al.

(10) Patent No.: US 9,044,506 B2
(45) Date of Patent: *Jun. 2, 2015

(54) MIR-21 PROMOTER DRIVEN TARGETED CANCER THERAPY

(71) Applicant: Ramot at Tel Aviv University, Ltd., Tel Aviv (IL)

(72) Inventors: Rina Rosin-Arbesfeld, Herzliya (IL); Ella Sklan, Raanana (IL); Alona Zilberberg, Tel Aviv (IL); Naama David, Givatayim (IL)

(73) Assignee: Alona Zilberberg, Tel Aviv (IL)

( * ) Notice: Subject to any disclaimer, the term of this patent is extended or adjusted under 35 U.S.C. 154(b) by 21 days.

This patent is subject to a terminal disclaimer.

(21) Appl. No.: 13/942,394

(22) Filed: Jul. 15, 2013

(65) Prior Publication Data

US 2013/0310446 A1 Nov. 21, 2013

Related U.S. Application Data

(63) Continuation of application No. 13/145,332, filed as application No. PCT/IL2010/000049 on Jan. 19, 2010, now Pat. No. 8,492,133.

(60) Provisional application No. 61/145,751, filed on Jan. 20, 2009.

(51) Int. Cl.
*C12N 15/85* (2006.01)
*A61K 48/00* (2006.01)
*A61K 38/16* (2006.01)

(52) U.S. Cl.
CPC ......... *A61K 48/0058* (2013.01); *C07K 2319/33* (2013.01); *C07K 2319/55* (2013.01); *C12N 15/85* (2013.01); *C12N 2830/008* (2013.01); *C12N 2830/85* (2013.01); *A61K 38/164* (2013.01)

(58) Field of Classification Search
CPC . A61K 48/0058; A61K 38/164; C12N 15/85; C12N 2830/008; C12N 2830/85; C07K 2319/33; C07K 2319/55
See application file for complete search history.

(56) References Cited

U.S. PATENT DOCUMENTS

| | | | |
|---|---|---|---|
| 5,998,205 A * | 12/1999 | Hallenbeck et al. | 435/325 |
| 7,041,654 B2 | 5/2006 | Hochberg et al. | |
| 7,919,245 B2 | 4/2011 | Brown et al. | |
| 2006/0105360 A1 | 5/2006 | Croce et al. | |
| 2008/0050744 A1 | 2/2008 | Brown et al. | |
| 2008/0171715 A1 | 7/2008 | Brown et al. | |
| 2008/0199961 A1 | 8/2008 | Rasko et al. | |
| 2008/0261908 A1 | 10/2008 | Croce et al. | |
| 2008/0306006 A1 | 12/2008 | Croce et al. | |
| 2008/0306017 A1 | 12/2008 | Croce et al. | |
| 2008/0306018 A1 | 12/2008 | Croce et al. | |
| 2009/0192101 A1 | 7/2009 | Hung et al. | |

FOREIGN PATENT DOCUMENTS

| | | | |
|---|---|---|---|
| WO | 99/18195 A2 | 4/1999 | |
| WO | 03/093441 A2 | 11/2003 | |
| WO | 2005/052129 A2 | 6/2005 | |
| WO | WO 2005052129 A2 * | 6/2005 | |
| WO | 2006/065938 A2 | 6/2006 | |
| WO | 2007/034487 A1 | 3/2007 | |
| WO | 2008/073303 A2 | 6/2008 | |
| WO | 2008/087642 A2 | 7/2008 | |

OTHER PUBLICATIONS

Loffler et al. "Interleukin-6—dependent survival of multiple myeloma cells involves the Stat3-mediated induction of microRNA-21 through a highly conserved enhancer." Blood. (2007); 110 (4): pp. 1330-1333.*
Kumarswamy et al. "Regulation and function of miRNA-21 in health and disease." RNA Biology (2011); 8:5: pp. 706-713.*
Schetter et al. "MicroRNA Expression Profiles Associated With Prognosis and Therapeutic Outcome in Colon Adenocarcinoma."JAMA. (2008); 299(4): pp. 425-436.*
Amaral, Fernando Colbariet al., (2009) MicroRNAs differentially expressed in ACTH-secreting pituitary tumors. J Clin Endocrinol Metab 94(1):320-323.
Barnes, Dwight et al., (2008) Harnessing Endogenous miRNAs to Control Virus Tissue Tropism as a Strategy for Developing Attenuated Virus Vaccines. Cell Host & Microbe 4239-248.
Bartel, David P. (2004) MicroRNAs: genomics, biogenesis, mechanism, and function. Cell 116(2):281-297.
Betel, D. et al., (2008) The microRNA.org resource: targets and expression. Nucleic Acids Res 36(Database issue): D149-153.
Cai, Xuezhong et al., (2004) Human microRNAs are processed from capped, polyadenylated transcripts that can also function as mRNAs. RNA 10(12):1957-1966.
Chan, Jennifer A. et al., (2005) MicroRNA-21 is an antiapoptotic factor in human glioblastoma cells. Cancer Res 65 (14):6029-6033.
Chan, Shin-Hsuan et al., (2008) miR-21 microRNA expression in human gastric carcinomas and its clinical association. Anticancer Res 28(2A):907-911.
Chang, Steven S. et al., (2008) MicroRNA alterations in head and neck squamous cell carcinoma. Int J Cancer 123 (12):2791-2797.
Connolly, Erin et al., (2008) Elevated expression of the miR-17-92 polycistron and miR-21 in hepadnavirus-associated hepatocellular carcinoma contributes to the malignant phenotype. Am J Pathol 173(3):856-864.
Dillhoff, Mary et al., (2008) MicroRNA-21 is Overexpressed in Pancreatic Cancer and a Potential Predictor of Survival. J Gastrointest Surg 12(12):2171-2176.

(Continued)

*Primary Examiner* — Thaian N Ton
*Assistant Examiner* — Titlayo Moloye
(74) *Attorney, Agent, or Firm* — Browdy and Neimark, PLLC

(57) ABSTRACT

The invention provides a nucleic acid construct comprising a promoter sequence derived from microRNA-21 (miR-21) linked to a nucleic acid sequence encoding an anti-cancer agent, an example of which is a toxin. The constructs of the invention are particularly useful for treating tumors expressing miR-21.

14 Claims, 5 Drawing Sheets

(56) References Cited

OTHER PUBLICATIONS

Esquela-Kerscher, Aurora and SLACK, Frank J. (2006) Oncomirs—microRNAs with a role in cancer. Nat Rev Cancer 6(4):259-269.
Feber, Andrew et al., (2008) MicroRNA expression profiles of esophageal cancer. J Thorac Cardiovasc Surg 135 (2):255-260; discussion 260.
Fujita, Shuji et al., (2008) miR-21 Gene Expression Triggered by AP-1 Is Sustained through a Double-Negative Feedback Mechanism. J Mol Biol 378(3):492-504.
Fujita, Shuji and Iba, Hideo (2008) Putative promoter regions of miRNA genes involved in evolutionarily conserved regulatory systems among vertebrates. Bioinformatics 24(3):303-308.
Fulci, Valerio et al., (2007) Quantitative technologies establish a novel microRNA profile of chronic lymphocytic leukemia. Blood 109(11):4944-4951.
Gabriely, Galina et al., (2008) MicroRNA 21 promotes glioma invasion by targeting matrix metalloproteinase regulators. Mol Cell Biol 28(17):5369-5380.
Gao, Jie et al., (2007) Cloning and identification of microRNA from human osteosarcoma cell line SOSP-9607. Chinese Journal of Cancer (Ai Zheng) 26(6):561-565 article in Chinese with English abstract.
Giladi, Nis et al., (2007) Gene therapy approach in prostate cancer cells using an active Wnt signal. Biomedicine & Pharmacotherapy 61(9):527-530.
Iorio, Marilena V. et al., (2005) MicroRNA gene expression deregulation in human breast cancer. Cancer Res 65 (16):7065-7070.
Iorio, Marilena V. et al., (2007) MicroRNA signatures in human ovarian cancer. Cancer Res 67(18):8699-8707.
Jiang, Jinmai et al., (2008) Association of MicroRNA expression in hepatocellular carcinomas with hepatitis infection, cirrhosis, and patient survival. Clin Cancer Res 14(2):419-427.
Kumarswamy, R. et al., (2011) Regulation and function of miRNA-21 in health and disease. RNA Biol 8(5):706-713.
Kutay, Huban et al., (2006) Downregulation of miR-122 in the rodent and human hepatocellular carcinomas. J Cell Biochem 99(3):671-678.
Ladeiro, Yannick et al., (2008) MicroRNA profiling in hepatocellular tumors is associated with clinical features and oncogene/tumor suppressor gene mutations. Hepatology 47(6):1955-1963.
Lawrie, Charles H. et al., (2007) MicroRNA expression distinguishes between germinal center B cell-like and activated B cell-like subtypes of diffuse large B cell lymphoma. Int J Cancer 121(5):1156-1161.
Lawrie, Charles H. et al., (2008) Detection of elevated levels of tumour-associated microRNAs in serum of patients with diffuse large B-cell lymphoma. Br J Haematol 141(5):672-675.
Lee, Eun Joo et al., (2006) Expression profiling identifies microRNA signature in pancreatic cancer. Int J Cancer 120 (5):1046-1054.
Loffler, Dennis et al., (2007) Interleukin-6 dependent survival of multiple myeloma cells involved the Stat3-mediated induction of microRNA-21 through a highly conserved enhance. Blood 11(4):1330-1333.

Lui, Weng-Onn et al., (2007) Patterns of known and novel small RNAs in human cervical cancer. Cancer Res 67(13):6031-6043.
Markou, Athina et al., (2008) Prognostic value of mature microRNA-21 and microRNA-205 overexpression in non-small cell lung cancer by quantitative real-time RT-PCT. Clin Chem 54(10):1696-1704.
Meng, Fanyin et al., (2006) Involvement of human micro-RNA in growth and response to chemotherapy in human cholangiocarcinoma cell lines. Gastroenterology 130(7):2113-2129.
Nam, Eun Ji et al., (2008) MicroRNA expression profiles in serous ovarian carcinoma. Clin Cancer Res 14(9):2690-2695.
Neely, Lori A. et al., (2010) A microRNA expression ratio defining the invasive phenotype in bladder tumors. Urol Oncol 28(1):39-48.
Ohana, Patricia et al., (2005) Regulatory sequences of H19 and IGF2 genes in DNA-based therapy of colorectal rat liver metastases. J Gene Med 7(3):366-374.
Pichiorri, Flavia et al., (2008) MicroRNAs regulate critical genes associated with multiple myeloma pathogenesis. Proc Natl Acad Sci U S A 105(35):12885-12890.
Qian, Biyun et al., (2009) High miR-21 expression in breast cancer associated with poor disease-free survival in early stage disease and high TGF-beta1. Breast Cancer REs Treat 117(1):131-140.
Roldo, Claudia et al., (2006) MicroRNA expression abnormalities in pancreatic endocrine and acinar tumors are associated with distinctive pathologic features and clinical behavior. J Clin Oncol 24(29):4677-4684.
Schetter, Aaron J. et al., (2008) MicroRNA expression profiles associated with prognosis and therapeutic outcome in colon adenocarcinoma. JAMA 299(4):425-436.
Sempere, Lorenzo F. et al., (2007) Altered MicroRNA expression confined to specific epithelial cell subpopulations in breast cancer. Cancer Res 67(24):11612-11620.
Si, M.-L. et al., (2007) miR-21-mediated tumor growth. Oncogene 26(19):2799-2803.
Slaby, O. et al., (2007) Altered expression of miR-21, miR-31, miR-143 and miR-145 is related to clinicopathologic features of colorectal cancer. Oncology 72(5-6):397-402.
Tran, Nham et al., (2007) MicroRNA expression profiles in head and neck cancer cell lines. Biochem Biophys Res Commun 358(1):12-17.
Varda-Bloom, N. et al., (2008) Specific Induction of Tumor Neovasculature Death by Modified Murine PPE-1 Promoter Armed with HSV-TK. Pathobiology 75(6):346-355.
Volinia, Stefano et al., (2006) A microRNA expression signature of human solid tumors defines cancer gene targets. Proc Natl Acad Sci U S A 103(7):2257-2261.
Wang, Tongsheng et al., (2007) A micro-RNA signature associated with race, tumor size, and target gene activity in human uterine leiomyomas. Genes Chromosomes Cancer 46(4):336-347.
Yan, Li-Xu et al., (2008) MicroRNA miR-21 overexpression in human breast cancer is associated with advanced clinical stage, lymph node metastasis and patient poor prognosis. RNA 14(11):2348-2360.
Zhang, Zhiyu et al., (2008) miR-21 plays a pivotal role in gastric cancer pathogenesis and progression. Lab Invest 88(12):1358-1366.

* cited by examiner

Fig. 4A
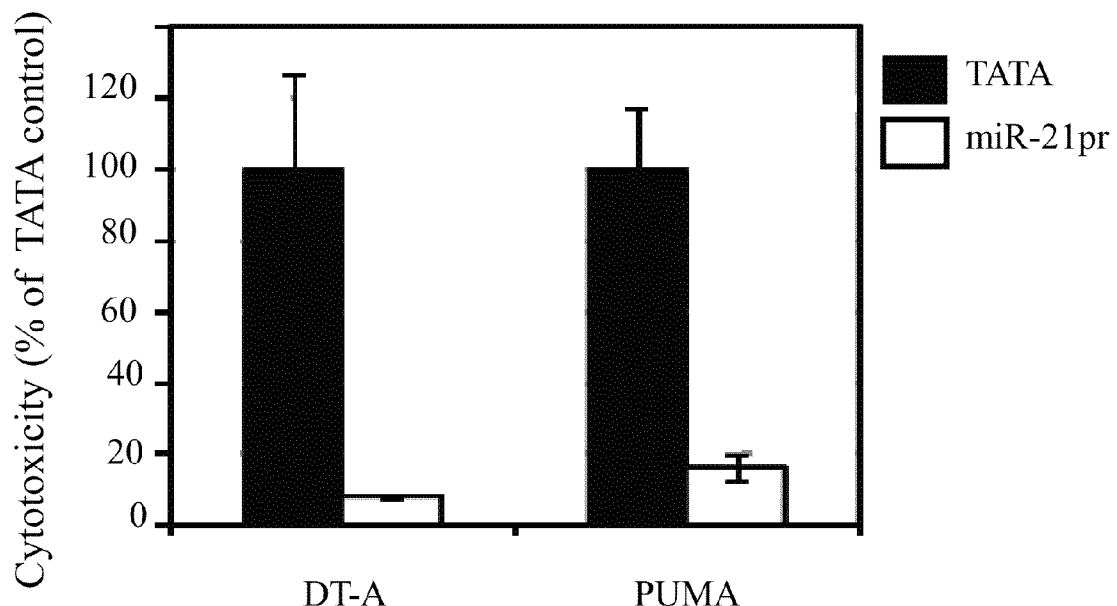
Fig. 4B
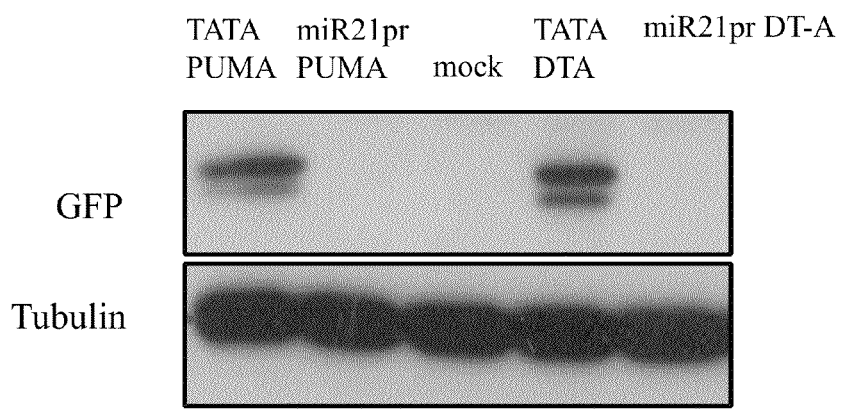
Figure 4

MIR-21 PROMOTER DRIVEN TARGETED CANCER THERAPY

RELATED APPLICATIONS

This application is a continuation of U.S. application Ser. No. 13/145,332, filed on Nov. 17, 2011, which is a national phase filing under 35 U.S.C. 371 of International Application No. PCT/IL2010/000049, filed on Jan. 19, 2010, which claims the benefit of U.S. Provisional Application No. 61/145,751, filed on Jan. 20, 2009, the entirety of these applications is hereby incorporated herein by reference for the teachings therein.

FIELD OF THE INVENTION

The present invention is directed to the field of cancer treatment, and provides a nucleic acid construct particularly useful for treating tumors expressing miR-21.

BACKGROUND OF THE INVENTION

MicroRNAs (miRNAs) are an abundant class of short (20-24 nt) endogenous noncoding RNAs that act as post-transcriptional regulators of gene expression by base-pairing with their target mRNAs (for review see for example, Bartel, Cell 2004, 116:281-297). In general, genes encoding miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70 nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA.

To date, several hundred miRNAs have been described in humans and a large number of them have been implicated in cancer. miRNAs that have been experimentally shown directly to induce tumor phenotypes (i.e., formation) have been termed "oncomirs". MiR-21 (also known as MIRN21, miRNA21, hsa-mir-21 and MIR21) is such an oncomir shown to target multiple tumor/metastasis suppressor genes and to have a role in tumor growth, invasion and metastasis. Various studies show that miR-21 is exclusively expressed in cancerous cell lines and solid human tumors, but not in non-transformed cell lines or in the adjacent non cancerous tissue (see for example, Iorio et al., Cancer Res, 2005. 65(16): 7065-7070; Si et al., Oncogene, 2007. 26(19): 2799-2803; Volinia et al., Proc Natl Acad Sci USA, 2006. 103(7): 2257-2261). Thus, evaluation of miR-21 expression has been suggested in cancer diagnosis (see, for example, U.S. Patent Application Publication No. 2006/0105360).

U.S. Patent Application Publication No. 2008/0306018 discloses methods for diagnosing pancreatic cancer comprising measuring the level of at least one miRNA gene product, including miR-21, in a test sample from the subject. This publication further discloses a method of treating pancreatic cancer in a subject in which at least one miRNA gene product is downregulated or upregulated in the cancer cells relative to control cells, inter alia when miR-21 is upregulated in the cancer cells, the method comprising administering to the subject an effective amount of at least one compound for inhibiting expression of the at least one miRNA gene product, such that proliferation of cancer cells in the subject is inhibited. Also disclosed are pharmaceutical compositions for treating pancreatic cancer, comprising at least one isolated miRNA gene product or an inhibitor thereof.

Similar methods and compositions have been disclosed for the treatment of lung cancer (U.S. Patent Application Publication No. 2008/0306017), breast cancer (U.S. Patent Application Publication No. 2008/0261908) and solid cancers such as prostate cancer, stomach cancer, pancreatic cancer, lung cancer, breast cancer and colon cancer (U.S. Patent Application Publication No. 2008/0306006). Other exemplary publications which suggest elevating or inhibiting the expression of miR-21 include U.S. Patent Application Publication Nos. 2008/0171715, 2008/0199961 and 2008/0050744. Certain attempts to use miRNAs to control tissue tropism have also been reported (see for example, Barnes et al., Cell Host Microbe, 2008. 4(3):239-248).

Selective targeting of a specific cancer using differentially expressed genes has been previously demonstrated successfully where regulatory sequences of the H19 gene differentially expressed in bladder cancer were used to control the expression of diphtheria toxin (Ohana et al., J Gene Med, 2005. 7(3): 366-374).

WO 99/18195 and U.S. Pat. No. 7,041,654 teach the specific expression of heterologous sequences, particularly genes encoding cytotoxic products (e.g. diphtheria toxin), in tumor cells under the control of a cancer specific promoter (e.g., H19 and IGF promoters).

WO 2007/034487 discloses a nucleic acid construct comprising: (i) a first nucleic acid sequence encoding TNF alpha; (ii) a second nucleic acid sequence encoding a Diphtheria toxin; and (iii) at least one additional nucleic acid sequence comprising a cancer specific promoter (e.g. H19 and IGF promoters); the TNF alpha and Diphtheria toxin encoding sequences being under an expression control of the cancer specific promoter. Also disclosed are construct systems and methods and uses thereof.

WO 2008/087642 discloses compositions and methods for the treatment of cancer and other conditions that are associated with elevated expression of the H19 gene, utilizing constructs encoding H19-silencing nucleic acid agents such as inhibitory RNA.

WO 2006/065938 discloses, inter alia, a method for treating cancer in a mammal comprising administering to the mammal an effective amount of a nucleic acid that encodes an anticancer agent operably linked to a SPANX-N1 promoter.

WO 2003/093441 discloses a method of inhibiting expression of a gene in a cell comprising introducing into said cell a DNA construct comprising a promoter functional in said cell operably linked to a nucleic acid sequence encoding an miRNA precursor having a stem loop structure and comprising in said stem a sequence complementary to a portion of an RNA transcript of said gene, wherein, following introduction of said construct into said cell, said nucleic acid sequence is transcribed and processed so that said miRNA precursor is produced. Further disclosed is a plasmid construct comprising precursor miRNA-21 linked to a CMV promoter.

Cai et al. disclose a plasmid containing the firefly luciferase gene linked to an ~1 kb DNA fragment of the pri-miR-21 transcription unit corresponding to the region from −959 to +49 relative to the T1 transcription start site (Cai et al., RNA (2004) 10:1957-1966). According to this disclosure, firefly luciferase activity was detected in 293T cells transfected with such a plasmid, leading the authors to conclude that sequences located 5' to the pri-miR-21 transcription unit can function as an mRNA promoter.

Fujita and Iba disclose a putative promoter region of miR-21 462 nucleotides in length (Fujita and Iba Bioinformatics 2008, 24(3):303-308), and Fujita et al disclose the miR-21 promoter including binding sites for activation protein 1 and PU.1 (Fujita et al., J Mol Biol 2008 May 2; 378(3):492-504).

While several therapeutic approaches utilizing gene therapy in cancer patients have been suggested, there exists a need for additional efficacious anti-cancer agents and vectors. As tumors are known to exhibit significant genomic instability and heterogeneity, the use of hitherto known gene therapy vectors is likely to fail in a substantial number of the patients.

Nowhere in the prior art is it taught or suggested that a miR-21 promoter can be used in recombinant nucleic acid constructs for expressing selectively cytotoxic agents in cancer cells. Nor does the art demonstrate the use of such vectors as an effective and safe anti-cancer treatment in vivo. There remains an unmet medical need for developing gene therapy vectors having enhanced therapeutic activity, minimized toxicity and a broad target range for treating neoplastic disorders.

SUMMARY OF THE INVENTION

The invention is directed to nucleic acid constructs and methods for providing targeted cancer therapy. Specifically, the constructs of the invention comprise at least one nucleic acid sequence encoding a cytotoxic or cytostatic anti-cancer molecule, such as a toxin, the nucleic acid sequence being operably linked to an miR-21 transcription-regulating sequence. Vectors comprising these constructs, pharmaceutical compositions comprising them and use thereof for treating cancers and solid tumors are also provided.

The present invention discloses for the first time novel nucleic acid constructs and vectors in which expression of an anti-cancer agent is placed under the transcriptional control of an miR-21 promoter sequence. The inventors of the present invention have surprisingly demonstrated that such constructs have activity in depressing de novo protein synthesis in cancer cells in vitro, and moreover inhibit tumor growth and metastasis in vivo.

The invention is based, in part, on the finding that direct injection into tumors induced in mice, of a nucleic acid construct having an miR-21 promoter operatively linked to a nucleic acid sequence encoding diphtheria toxin, results either in complete eradication of the tumor or substantial inhibition of tumor growth.

Thus, in a first aspect the present invention provides a nucleic acid construct comprising a miR-21 promoter sequence and at least one nucleic acid sequence encoding an anti-cancer agent, wherein the nucleic acid sequence encoding the anti-cancer agent is operably linked to the miR-21 promoter sequence.

In particular embodiments, the nucleic acid construct is the product of recombinant methods, a chemical synthesis or a combination thereof.

In particular embodiments, the miR-21 promoter sequence has at least 80% identity with SEQ ID NO: 1. In particular embodiments, the miR-21 promoter sequence has at least 85%, or at least 90% identity, or at least 95% identity with SEQ ID NO: 1. In particular embodiments, the miR-21 promoter sequence comprises SEQ ID NO: 1.

In particular embodiments, the anti-cancer agent is selected from cytotoxic and cytostatic proteins and peptides capable of killing a target cell or inhibiting its growth or proliferation. In particular embodiments, the anti-cancer agent is selected from a toxin, a drug-metabolizing enzyme which converts a prodrug to a drug having cytotoxic activity, an inducer of apoptosis, and a combination thereof. In particular embodiments, the toxin is selected from the group consisting of a bacterial toxin, a plant toxin, a fungal toxin, and a combination thereof. In particular embodiments, the bacterial toxin is selected from the group consisting of diphtheria toxin, *Pseudomonas* exotoxin, cholera toxin, anthrax toxin, botulinum toxin, pertussis toxin, *E. coli* enterotoxin, and shiga toxin. In particular embodiments, the plant toxin is selected from the group consisting of ricin, modeccin, abrin, volkensin and viscumin. In particular embodiments, the fungal toxin is selected from the group consisting of α-sarcin, restrictocin, mitogillin, enomycin, RNase T1 and phenomycin.

In particular embodiments, the toxin comprises a cytotoxic fragment of a naturally occurring toxin. In particular embodiments, the cytotoxic fragment of a toxin is fragment A of diphtheria toxin (DT-A). In particular embodiments, DT-A has the amino acid sequence of SEQ ID NO: 19. In particular embodiments, the nucleic acid sequence encoding DT-A comprises SEQ ID NO: 18.

In particular embodiments, the drug-metabolizing enzyme is a kinase. In particular embodiments, the kinase is a thymidine kinase. In particular embodiments, the prodrug target of the thymidine kinase is ganciclovir. In particular embodiments, the kinase is a viral thymidine kinase. In particular embodiments, the inducer of apoptosis is selected from the group consisting of PUMA; BAX; BAK; Bcl-XS; BAD; BIM; BIK; BID; HRK; Ad E1B; an ICE-CED3 protease; TRAIL; SARP-2; and apoptin.

In a particular embodiment, the construct comprises SEQ ID NO: 1 as the miR-21 promoter sequence and further comprises SEQ ID NO: 18 as the nucleic acid sequence encoding an anti-cancer agent. In particular embodiments, the nucleic acid sequence comprising an miR-21 promoter sequence is substantially devoid of a nucleic acid sequence corresponding to or complementary to an miR-21 transcription or processing product. In particular embodiments, the nucleic acid construct is substantially devoid of a nucleic acid sequence corresponding to or complementary to a form of miR-21 selected from the group consisting of: a primary transcript of miR-21 (pri-miR-21); a precursor of miR-21 (pre-miR-21); an RNA duplex of miR-21, and a mature miR-21. In particular embodiments, the nucleic acid construct is substantially devoid of a nucleic acid sequence corresponding to or complementary to a nucleic acid sequence selected from the group consisting of: SEQ ID NO: 2; SEQ ID NO: 3; SEQ ID NO: 4; SEQ ID NO: 5 and SEQ ID NO: 26.

In a particular embodiment, the nucleic acid construct comprises a sequence selected from the group consisting of SEQ ID NO: 7 and SEQ ID NO: 8.

In a particular embodiment, the miR-21 promoter sequence is a variant of a native miR-21 promoter, such as a homolog, analog or fragment of a native miR-21 promoter.

In another aspect, the invention provides a vector comprising the recombinant nucleic acid construct of the invention.

In another aspect, the invention provides an isolated host cell comprising the vector of the invention.

In a particular embodiment, the vector is selected from the group consisting of SEQ ID NO: 9 and SEQ ID NO: 10.

In a particular embodiment, the construct encodes a fusion protein comprising the anti-cancer agent. In a particular embodiment, the construct further comprises a nucleic acid sequence that encodes an antibody or a fragment thereof comprising at least the antigen binding portion of the antibody, wherein the antibody or antibody fragment is specific for a cancer-related protein. In a particular embodiment, the construct comprises a nucleic acid sequence encoding a fusion protein wherein the fusion protein comprises segments corresponding to the anti-cancer agent and to the antibody or antibody fragment.

In another aspect, the invention provides a pharmaceutical composition comprising as an active ingredient at least one nucleic acid construct of the invention and a pharmaceutically acceptable carrier, excipient or diluent.

In another embodiment, the present invention provides a method for treating cancer in a human subject, the method comprising administering to a human subject in need thereof a therapeutically effective amount of a nucleic acid construct of the present invention, thereby treating cancer in the human subject.

In another embodiment, the present invention provides a method for inhibiting tumor progression in a human subject, the method comprising administering to a human subject in need thereof a therapeutically effective amount of a nucleic acid construct of the present invention, thereby inhibiting tumor progression in the human subject.

In another embodiment, the present invention provides a method for inhibiting tumor metastasis in a human subject, the method comprising administering to a human subject in need thereof a therapeutically effective amount of a nucleic acid construct of the present invention, thereby inhibiting tumor metastasis in the human subject.

In another embodiment, the present invention provides a method for reducing or alleviating a symptom associated with a neoplastic disorder in a human subject, the method comprising administering to a human subject in need thereof a therapeutically effective amount of a nucleic acid construct of the present invention, thereby reducing or alleviating a symptom associated with a neoplastic disorder in the human subject.

In the methods of the invention, said subject is afflicted, in one embodiment, with a cancer, tumor or a neoplastic disorder characterized by endogenous expression of miR-21 in at least a portion of the cells thereof.

In particular embodiments, the administering is carried out by a route selected from the group consisting of injection, infusion and direct injection into the tumor.

In particular embodiments, the administering comprises administering a single dose or multiple doses of the nucleic acid construct.

In particular embodiments, the methods further comprise a step of determining the level of miR-21 transcriptional activity in a biological sample e.g. cells or tissue, from the subject.

In particular embodiments, the methods are carried out in conjunction with at least one additional cancer therapy modality. In particular embodiments, the additional cancer therapy modality is selected from the group consisting of bone marrow transplant, cord blood cell transplant, surgery, chemotherapy, radiation therapy, immunotherapy and a combination thereof.

In another aspect, the present invention provides use of a nucleic acid construct of the invention for the preparation of a medicament for treating cancer in a human subject.

In another aspect, the present invention provides use of a nucleic acid construct of the invention for the preparation of a medicament for inhibiting tumor progression in a human subject.

In another aspect, the present invention provides use of a nucleic acid construct of the invention for the preparation of a medicament for inhibiting tumor metastasis in a human subject.

In another aspect, the present invention provides use of a nucleic acid construct of the invention for the preparation of a medicament for reducing or alleviating a symptom associated with a neoplastic disorder.

In another aspect, the present invention provides a kit containing i) one or more dosage units of a nucleic acid construct of the invention sufficient for one or more courses of treatment for a cancer, tumor or neoplasm expressing miR-21; and ii) instructions for administering said nucleic acid construct to a subject in need thereof.

The compositions, methods and kits of the present invention are useful in the treatment of a variety of cancers and neoplastic disorders associated with expression of miR-21. In a particular embodiment, the cancer is selected from the group consisting of a sarcoma, a carcinoma, an adenocarcinoma, a lymphoma, and a leukemia. In a particular embodiment, the cancer is selected from the group consisting of breast cancer, colon cancer, hepatocellular carcinoma, cervical cancer, cholangiocarcinoma, endometrioid ovarian carcinoma, esophageal cancer, glioblastoma, head and neck cancer, leukemia, lymphoma, lung cancer, multiple myeloma, pancreatic cancer, osteosarcoma, pituitary tumor, prostate cancer, stomach cancer, and uterine leiomyoma. In a particular embodiment, the cancer is selected from the group consisting of breast cancer, colon cancer and hepatocellular carcinoma.

Other objects, features and advantages of the present invention will become clear from the following description and drawings.

BRIEF DESCRIPTION OF THE DRAWINGS

FIG. 4 demonstrates inhibition of expression of *Renilla* luciferase or green fluorescent protein (GFP) in models of reduction of de novo protein synthesis.

FIG. 4A (white bars) shows the results of co-transfection experiments in which cells were co-transfected with miR-21 Pr DT-A (SEQ ID NO: 9) or miR-21 pr PUMA (a vector encoding the p53 up-regulated modulator of apoptosis (PUMA) under the control of the miR-21 promoter; SEQ ID NO: 10), together with a reporter plasmid encoding *Renilla* luciferase. FIG. 4A (black bars) shows the results of cotransfection experiments in control systems in which cells were co-transfected with miR-21 TATA box DT-A (SEQ ID NO: 13) or TATA PUMA (a vector encoding PUMA under the control of the TATA-box sequence of the miR-21 promoter; SEQ ID NO: 29), together with the plasmid encoding *Renilla* luciferase.

FIG. 4B shows the results of co-transfection experiments performed as for those depicted in FIG. 4A, except that a plasmid encoding GFP was used as the reporter plasmid. Cells were harvested 72 hours post-transfection and subjected to luciferase assay (FIG. 4A) or Western blot analysis (FIG. 4B).

DETAILED DESCRIPTION OF THE INVENTION

Figure 1:
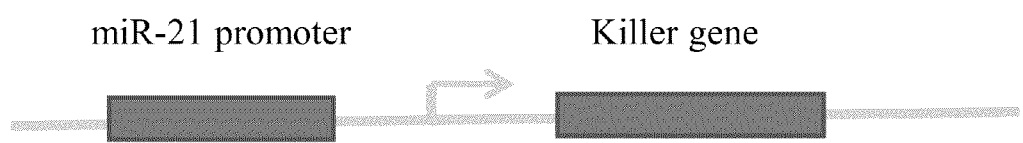
FIG. 1 provides a schematic representation of the nucleic acid construct of the invention, in which a nucleic acid sequence encoding an anti-cancer agent ("killer gene") is operably linked to a miR-21 promoter sequence.

The present invention is directed to nucleic acid constructs and methods for providing targeted cancer therapy. Specifically, the constructs of the invention comprise at least one nucleic acid sequence encoding a heterologous anti-cancer gene product, the nucleic acid sequence being operably linked to a miR-21 transcription-regulating sequence, in particular, an miR-21 promoter sequence. Vectors comprising these constructs, pharmaceutical compositions comprising them and methods of use thereof are also provided.

The efficacy of the present invention is unexpected over prior art disclosures which teach suppression of miR-21 driven processes for treatment of cancers in which miR-21 is highly expressed, such as by administration of agents which inhibit miR-21 activity, or use of miR-21 for inactivating genes involved in oncogenesis. That is, the harnessing of the miR-21 promoter for driving expression of tumor killing agents, as taught by the present invention, provides a reversal of prior art approaches to therapy of miR-21-associated cancers.

Definitions

As used herein, the terms "microRNA" and "miRNA" interchangeably refer to a single-stranded non-coding regulatory RNA of approximately 22-25 nucleotides in length, generated by the action of RNase-III-type enzymes on an endogenous primary transcript (pri-miRNA).

As used herein, the terms "miRNA biogenesis", "miRNA pathway" and "miRNA processing pathway" interchangeably refer to the RNA metabolic process leading to miRNA formation that includes transcription of the primary miRNA transcript (pri-miRNA), cleavage of pri-miRNA to create an intermediate precursor miRNA (pre-miRNA) and subsequent processing of pre-miRNA to create the mature miRNA.

As used herein, the term "miR-21" refers to the mature processed form of the miRNA having the sequence of SEQ ID NO: 5.

As used herein, the term "miR-21 promoter" refers to the native nucleic acid sequence which is located upstream of an miR-21 gene and is required for the transcription thereof, so as to produce a primary transcript of miR-21 (pri-miR-21). Exemplary human pri-miR-21 sequences include: GenBank accession number BC053563 (disclosed herein as SEQ ID NO: 2); GenBank accession number AY699265 (disclosed herein as SEQ ID NO: 3), and that disclosed in Fujita et al., J Mol Biol 2008 May 2; 378(3):492-504 (disclosed herein as SEQ ID NO: 26). As used herein, the term "miR-21 promoter sequence" refers to a nucleic acid sequence derived from an miR-21 promoter and having at least about 80% identity to SEQ ID NO:1.

As used herein, the term "an miR-21 transcription or processing product" refers to a nucleic acid transcription or processing product derived from an miR-21 gene in the pathway to mature miR-21, including a primary transcript of miR-21 (pri-miR-21), such as those having GenBank accession numbers BC053563 and AY699265; an intermediate precursor of miR-21 (pre-miR-21), such as those having GenBank accession numbers NR_029493, AF_480546 and AF_480557; and mature miR-21, such as that having GenBank accession number NR_029493.

As used herein, the term "nucleic acid sequence corresponding to or complementary to an miR-21 transcription or processing product" refers to a DNA or RNA sequence that is either identical to i.e. "corresponds to" the sequence of an miR-21 transcription or processing product, or could demonstrate complete base-pairing i.e. is "complementary to" to the miR-21 transcription or processing product. For example, a subject DNA would "correspond to" a cDNA produced from an miR-21 RNA transcript, provided that the sequences of the subject DNA and the cDNA were identical, whereas the same subject DNA would be "complementary to" the aforementioned miR-21 transcript.

As used herein, the term "nucleic acid construct" refers to a continuous polynucleotide molecule comprising at least two heterologous nucleic acid sequences that are joined together to form a single unit. The nucleic acid sequences comprising the construct may include polypeptide coding sequences and non-coding sequences.

The terms "polynucleotide", "polynucleotide sequence", "nucleic acid", "nucleic acid sequence" and "oligonucleotide" are used interchangeably herein to refer to polymeric forms of nucleotides of any length, such as deoxyribonucleotides, ribonucleotides, or modified forms thereof in the form of an individual fragment or as a component of a larger construct, in a single strand or in a double strand or multi-strand form. The polynucleotides to be used in the invention include sense and antisense sequences of DNA or RNA, genomic DNA, cDNA, DNA-RNA hybrids, or a polymer comprising purine and pyrimidine bases or other natural, chemically or biochemically modified, non-natural, or derivatized nucleotide bases. Further included are mRNA or cDNA that comprise intronic sequences The backbone of the polynucleotide can comprise sugars and phosphate groups (as typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer (see, e.g., Peyrottes et al. (1996) Nucl. Acids Res. 24:1841-1848; Chaturvedi et al (1996) Nucl. Acids Res. 24:2318-2323). A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component, capping, substitution of one or more of naturally occurring nucleotides with an analog, and introduction of means for attaching the polynucleotide to proteins, metal ions, labeling components, other polynucleotides, or a solid support.

A polynucleotide can comprise a nucleotide sequence disclosed herein wherein thymidine (T) can also be uracil (U); this definition pertains to the differences between the chemical structures of DNA and RNA, in particular the observation that one of the four major bases in RNA is uracil (U) instead of thymidine (T).

The term "recombinant nucleic acid construct" as used herein refers to a nucleic acid construct that has been subjected to molecular manipulation in vitro, such as for example joining together nucleic acid sequences by ligation.

As used herein, the term "operably linked" refers to the structural and functional relationship between two or more nucleic acid sequences joined together as part of the same polynucleotide, generally a regulatory sequence and a protein coding sequence. For example, a nucleic acid sequence encoding a protein is operably linked to a promoter if transcription is initiated from the promoter; or a nucleic acid sequence encoding a protein is operably linked to a ribosome binding site if translation of the corresponding mRNA is initiated from the ribosome binding site. In the present invention, a nucleic acid encoding a protein having anti-cancer activity is operably linked to an miR-21 transcription control sequence, preferably an miR-21 promoter sequence, such that transcription of the nucleic acid is effected or enhanced. Generally, "operably linked" means that the nucleic acid sequences being linked are contiguous, although enhancers do not have to be contiguous. Linking is accomplished by ligation at convenient restriction sites, or if such sites do not exist, synthetic oligonucleotide adaptors or linkers may be used in accordance with conventional practice.

Transcription control sequences are sequences, which control the initiation, elongation, and termination of transcription. Particularly important transcription control sequences are those which control transcription initiation, such as promoter, enhancer, operator and repressor sequences.

As used herein, the term "vector" refers to a nucleic acid construct, comprising a regulatory sequence linked to a heterologous polynucleotide that is inserted to target cells for replication and/or expression therein. The vector can be a viral expression vector, a plasmid or a construct of naked DNA, and, optionally, can include additional sequences required for construction, selection, stability, penetration, etc.

As used herein, the terms "protein" and "polypeptide" refer interchangeably to a polymer of at least about 10 amino acids joined together through peptide bonds. Throughout the specification, standard three letter or single letter designations for amino acids are used.

As used herein, the terms "recombinant protein" and "recombinant polypeptide" refer interchangeably to a protein produced using cells that do not have, in their native state, an endogenous copy of the nucleic acid (DNA or RNA) capable of expressing the protein. The cells produce the recombinant protein because they have been genetically altered by the introduction of the appropriate isolated nucleic acid sequence, for example as a component of an expression vector.

As used herein, the term "fusion protein" as used herein refers to a protein sequence composed of segments i.e. amino acid sequences, which correspond to heterologous protein sequences, such as proteins of different function and/or proteins from different organisms. The segments are joined either directly or indirectly to each other via peptide bonds, and may correspond to either full-length proteins or fragments thereof. By indirect joining it is meant that an intervening amino acid sequence, such as a peptide linker is juxtaposed between segments forming the fusion protein. Fusion proteins may be produced by recombinant technology from a polynuceotide comprising the nucleic acid sequences encoding the various segments of the fusion protein.

As used herein, the term "drug-metabolizing enzyme" refers to an enzyme which converts a prodrug into a cytotoxic product.

As used herein, the term "prodrug" refers to a precursor or derivative form of a pharmaceutically active substance that is less cytotoxic to tumor cells compared to the parent drug and is capable of being enzymatically activated or converted into the more active parent form.

As used herein, the term "heterologous" when used in reference to distinct nucleic acid sequences or distinct protein sequences, means that the sequences differ with respect to their sequence, structure and/or the organism from they are derived or produced.

As used herein, the term "homolog" refers to a molecule, generally a polypeptide or nucleic acid sequence, which exhibits homology to another molecule, by having sequences of chemical residues that are identical or similar at corresponding positions.

Sequence similarity and sequence identity are calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. In general, percent sequence identity is calculated by counting the number of residue matches (e.g., nucleotide residue or amino acid residue) between the query and test sequence and dividing total number of matches by the number of residues of the individual sequences found in the region of strongest alignment, or along a complete region following the introduction of gaps, as is known in the art. Algorithms for computer-based alignment and sequence analysis are known in the art (see, e.g., Altschul et al., (1990) J. Mol. Biol., 215:403-10), and publicly available software tools such as BLAST, BLAST-2, ALIGN, ALIGN-2 or Megalign (DNASTAR), are well known in the art.

Accordingly, "percent (%) nucleic acid sequence identity" with respect to a miR-21 promoter nucleic acid sequence identified herein is defined as the percentage of nucleotides in a candidate sequence that are identical with a disclosed miR-21 promoter nucleic acid sequence, after aligning the sequences and introducing gaps, if necessary, to achieve the maximum percent sequence identity. Alignment for purposes of determining percent nucleic acid sequence identity can be achieved using the aforementioned computer software tools.

As used herein, the term "variant" refers to substantially similar sequences possessing common qualitative biological activities. An oligonucleotide variant includes a pharmaceutically acceptable salt, homolog, analog, extension or fragment of a nucleotide sequence useful for the invention, such as an miR-21 promoter sequence. Encompassed within the term "variant" are chemically modified natural and synthetic nucleotide molecules. Also encompassed within the term "variant" are substitutions (conservative or non-conservative), additions or deletions within the nucleotide sequence of the molecule, as long as the required function is sufficiently maintained. Oligonucleotide and polynucleotides variants may share at least 50%, 55%, 60%, 65%, 70%, 75%, 80%, 85%, 90%, 95%, 96%, 97%, 98% or 99% sequence identity.

As used herein in the context of polynucleotides, the terms "hybridize", "hybridizing", "hybridizes" and the like, refer to conventional hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, John Wiley and Sons, Baltimore, Md., 1988.

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0. 1×SSC containing EDTA at 55° C.

As used herein, the term "isolated" in reference to a nucleic acid molecule means that the nucleic acid molecule is initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments, a nucleic acid is isolated by virtue of it having been synthesized in vitro separate from endogenous nucleic acids in a cell. It will be understood, however, that isolated nucleic acids may be subsequently mixed or pooled together.

As used herein, the term "anti-cancer agent" refers to a protein or peptide that exerts an inhibitory or cytotoxic effect on a cancer cell, either directly or indirectly. For example, a cytotoxic drug that kills a cancer cell exerts a direct effect on the cancer cell, while an enzyme which converts a prodrug to its active cytotoxic form which then kills the cancer cell, exerts an indirect effect.

The terms "cancer" and "neoplasm" are used herein interchangeably to refer to a disease state characterized by cells in an abnormal state or condition characterized by rapid proliferation. A "tumor" containing such cells may be either benign, premalignant or malignant. The terms include disease states characterized by all types of hyperproliferative growth, hyperplastic growth, cancerous growths, oncogenic processes, metastatic tissues, malignantly transformed cells, tissues, or organs, irrespective of histopathologic type or stage of invasiveness.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of connective tissue such as bone or cartilage.

As used herein, the term "leukemia" and "leukemic cancer" refer to all cancers of the hematopoietic and immune systems (blood and lymphatic system). These terms refer to a progressive, malignant disease of the blood-forming organs, marked by distorted proliferation and development of leukocytes and their precursors in the blood and bone marrow. Myelomas refer to other types of tumors of the blood, bone marrow cells. Lymphomas refer to tumors of the lymph tissue.

As used herein, the term "pharmaceutical composition" refers to a preparation comprising one or more pharmaceutically active ingredients e.g. a nucleic acid construct encoding an anti-cancer agent, and generally further comprising at least one pharmaceutically acceptable diluent, carrier or excipient. The purpose of a pharmaceutical composition is to facilitate administration of a pharmaceutically active ingredient to a subject.

As used herein, the term "active ingredient" refers to a component of a pharmaceutical composition that provides the primary pharmaceutical benefit, as opposed to an "inactive ingredient" which is generally recognized as providing no pharmaceutical benefit.

As used herein, the term "carrier, excipient or diluent" refers to an inactive ingredient, for example a tonicity adjusting agent, wetting agent or preservative, which facilitates formulation and/or administration of an active pharmaceutical ingredient.

As used herein, the term "pharmaceutically acceptable" refers to a non-toxic and inert substance that is physiologically compatible with humans or other mammals.

As used herein, the term "subject" refers to any mammal of any age having a cancer, in particular a human subject, but also including non-human mammals, such as primate, canine, feline, bovine, equine and murine species.

The term "antibody" (also referred to as an "immunoglobulin") is used in the broadest sense, and refers to polypeptides which exhibit binding specificity to a specific antigen. The term encompasses polyclonal and monoclonal antibodies, including both full length antibodies and antibody fragments so long as they exhibit the desired biological activity.

The terms "native" and "full length" antibodies" as used herein interchangeably refer to heterotetrameric glycoproteins of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

Depending on the amino acid sequence of the constant domain of their heavy chains, antibodies can be assigned to different classes. There are five major classes of antibodies IgA, IgD, IgE, IgG, and IgM, and several of these may be further divided into subclasses (isotypes), e.g., IgG1, IgG2, IgG3, IgG4.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The terms "polyclonal antibody" and "polyclonal antiserum" as used herein refer to a population of antibody molecules synthesized by a population of B cells. Polyclonal antibodies encompass a population of different antibody molecules which specifically bind to a particular antigen, wherein various antibodies in the mixture recognize different epitopes (also termed antigenic determinants).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, each monoclonal antibody is directed against a single epitope on the antigen. The modifier "monoclonal" indicates the character of the antibody as being obtained from a substantially homogeneous population of antibodies, and is not to be construed as requiring production of the antibody by any particular method. For example, monoclonal antibodies may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries, as is known in the art, for example using techniques such as those described in Clackson et al., Nature 352:624-628 (1991) and Marks et al., J. Mol. Biol. 222:581-597 (1991).

The terms "specifically interacts", "specifically binds" and "having specificity for" are used herein interchangeably to refer to high avidity and/or high affinity binding of an antibody to an antigen or epitope thereof, e.g., an epitope on a cancer cell. Antibody binding to its epitope is stronger than binding of the same antibody to any other epitope. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g., by use of appropriate controls.

The singular forms "a", "an", and "the" include plural referents unless the context clearly dictates otherwise. Thus, for example, reference to "a construct" includes one or more of such constructs, and so forth.

miR-21 Processing Pathway

Transcription of miRNA genes, including that of miR-21, is mediated by RNA polymerase II (pol II) to produce long primary transcripts (pri-miRNAs) that are often several kilobases long. Pri-miRNA transcripts contain both a 5' terminal cap structure and a 3' terminal poly(A) tail. Several poly(A)-containing transcripts containing both miRNA sequences and regions of adjacent mRNAs have been characterized. A human pri-miR-21, 3463 nucleotides in length, is disclosed under GenBank accession number AY699265, and a highly similar sequence from a human cDNA clone, 3404 nucleotides in length, is disclosed under GenBank accession number BC053563. A human pri-miR-21 is disclosed by Fujita et al., J Mol Biol 2008 May 2; 378(3):492-504.

Homologous miR-21 genes of non-human species are also known, including for example those available under GenBank accession numbers AY865965 (from Pan paniscus); AY865964 (from *Ateles geoffroyi*); AY865963 (from *Macaca nemestrina*); AY865962 (from *Pongo pygmaeus*); AY865961 (from *Gorilla gorilla*); AY865960 (from *Pan troglodytes*), and AY865959 (from *Macaca mulatta*).

The maturation of miRNA from pri-miRNAs involves trimming of pri-miRNAs into hairpin intermediates called precursor miRNAs (pre-miRNAs), that are subsequently cleaved into mature miRNAs. The stem-loop structure of pri-miRNA molecules are cleaved by the nuclear RNase III enzyme Drosha to release the pre-miRNA molecules. Drosha is a large protein of approximately 160 kDa, and, in humans, forms an even larger complex of approximately 650 kDa known as the Microprocessor complex. The enzyme is a Class II RNAse III enzyme having a double-stranded RNA binding domain (dsRBD).

Human sequences of pre-miR-21 include those available under GenBank accession numbers NR_29493; AF480546, and AF480557. Highly homologous non-human pre-miR-21 sequences include those available under GenBank accession numbers NR_032094 (*Equus caballus*); NR_030880 (*Bos taurus*); NR_029738 (*Mus musculus*); and NR_032151 (*Monodelphis domestica*).

Following export of pre-miRNA molecules to the cytoplasm, another RNase III enzyme called "Dicer" cleaves the pre-miRNA to produce the mature miRNA. Mature miRNAs are incorporated into an effector complex known as the miRNA-containing RNA-induced silencing complex or miRISC.

Mature human miR-21 is available under GenBank accession number NR_29493 and is disclosed herein as SEQ ID NO:5. Identical or nearly identical non-human miR-21 sequences include those available under GenBank accession numbers NR_032094 (*Equus caballus*); NR_030880 (*Bos taurus*); NR_029738 (*Mus musculus*); and NR_032151 (*Monodelphis domestica*).

Additional information concerning miRNAs and associated pri-miRNA and pre-miRNA sequences is available in miRNA databases such as miRBase (Griffiths-Jones et al. 2008 Nucl Acids Res 36, (Database Issue:D154-D158) and the NCBI human genome database.

It is to be noted that the sequences referred to and disclosed herein are expressed with DNA thymine bases (T) rather than the corresponding RNA uracil (U) bases, even in cases where the native sequences are RNA, such as for example mature miR-21.

Nucleic Acid Constructs, Vectors and Host Cells

The nucleic acid construct of the invention comprises a nucleic acid sequence encoding an anti-cancer agent operably linked to an miR-21 promoter sequence.

The miR-21 promoter sequence corresponds to a region positioned upstream of an miR-21 gene that functions in transcription of the corresponding pri-miR-21 transcript. The miR-21 promoter sequence used for the present invention may be the native sequence or a fragment thereof, as long as it retains the capability to drive transcription of the nucleic acid sequence to which it is operably linked.

The miR-21 promoter for use in the invention may be that which drives transcription of any of the known forms of pri-miR-21, such as the pri-miR-21 transcripts disclosed under GenBank accession numbers AY699265 and BC053563 and in Fujita et al., J Mol Biol 2008 May 2; 378(3):492-504. Transcripts of miR-21 may be characterized by methods known in the art, for example rapid amplification of cDNA ends (RACE), polymerase chain reaction (PCR) and primer extension, as described for example in Cai et al., RNA (2004) 10:1957-1966.

Putative promoter sequences located upstream i.e. 5' of known or identified pri-miR-21 transcription units may be PCR amplified from genomic DNA using appropriate primers, and isolated and purified using standard methods known in the art. Such purified fragments may then be ligated into vectors comprising heterologous nucleic acid sequences encoding reporter proteins, for example firefly luciferase. Such vectors are then transfected into cells and analyzed for the presence of the reporter protein, thereby indicating whether the test sequence functions as an mRNA promoter capable of driving expression of the reporter sequence. In parallel systems, one or more shorter subfragments may be separately cloned into the same vector and evaluated for reporter sequence expression, so as to identify the minimal region with promoter activity. A short subfragment, such as a putative TATA box, as well as antisense orientations of the various test sequences, may be similarly processed to serve as negative controls.

Exemplary experiments of this type are disclosed in Example 2 herein, which shows that an miR-21 promoter sequence of SEQ ID NO: 1 drives expression of a luciferase reporter gene, while a short fragment of the miR-21 promoter corresponding only to the TATA box (SEQ ID NO: 6), is incapable of driving expression of the same reporter sequence.

Accordingly, an exemplary miR-21 promoter sequence for use in the invention is SEQ ID NO: 1. SEQ ID NO 1 corresponds to nucleotides −1326 to −608 relative to the pri-mir-21 T1 transcription start site disclosed in Fujita et al., J Mol Biol 2008 May 2; 378(3):492-504. In other embodiments, the miR-21 promoter sequence has at least 80% identity with SEQ ID NO: 1, such as at least 85%, or at least 90% identity, or at least 95% identity with SEQ ID NO: 1. In particular embodiments, the miR-21 promoter sequence comprises SEQ ID NO: 1.

In particular embodiments, the miR-21 promoter sequence comprises recognition sequences typically present in eukaryotic promoters, in particular, the TATA box. Other promoter elements which may be present in the miR-21 promoter sequence include initiator, CCAAT box and GC box sites. The TATA box, typically located 25-30 base pairs upstream of the transcription initiation site, is thought to be involved in directing RNA polymerase to begin RNA synthesis. The other upstream promoter elements determine the rate at which transcription is initiated. Preferably, the miR-21 promoter sequence utilized in the nucleic acid construct of the present invention is active in the specific target cell population. In the constructs of the invention, it may be preferable to position the miR-21 promoter sequence relative to the sequence encoding the anti-cancer agent, such that the TATA box is the same distance from the transcription initiation site as occurs in the native gene encoding the anti-cancer agent.

The nucleic acid sequence comprising an miR-21 promoter sequence may, in some embodiments, be substantially devoid of a nucleic acid sequence corresponding to or complementary to an miR-21 transcription or processing product. furthermore, the nucleic acid construct may be substantially devoid of a nucleic acid sequence corresponding to or complementary to a precursor or intermediate form of miR-21, such as a primary transcript of miR-21 (pri-miR-21); a precursor of miR-21 (pre-miR-21); an RNA duplex of miR-21, and a mature miR-21. In particular embodiments, the nucleic acid construct of the invention is substantially devoid of a nucleic acid sequence corresponding to or complementary to a nucleic acid sequence selected from the group consisting of: SEQ ID NO: 2; SEQ ID NO: 3; SEQ ID NO: 4; and SEQ ID NO: 5.

In a particular embodiment, the nucleic acid construct comprises a sequence selected from the group consisting of SEQ ID NO: 7 and SEQ ID NO: 8.

The constructs, vectors and nucleic acid sequences of the present invention may be produced using standard recombinant, enzymatic and chemical synthetic methods well known in the art. A combination of such techniques may be used. An isolated nucleic acid sequence can be obtained from its natural source, either as an entire (i.e., complete) gene or a portion thereof. The desired nucleic acid molecule may be produced by polymerase chain reaction (PCR) amplification from a genomic template using suitable primer sequences. The amplified fragment may be manipulated by addition of synthetic restriction endonuclease sites, linkers etc for cloning into a particular vector enabling propagation and/or further manipulation and/or expression of a particular nucleic acid sequence. Such procedures enable construction of a single molecule e.g. construct or vector, characterized by the juxtaposition of specific heterologous nucleic acid sequences and including suitable flanking sequences which enable the desired functionalities of the construct. In addition, at least some of the desired nucleic acid molecules may be produced by assembly of chemically synthesized. oligonucleotides (see e.g. Sambrook et al., 2001, Molecular Cloning: A Laboratory Manual; Ausubel et al., supra). For example, a nucleic acid sequence produced by oligonucleotide assembly may be ligated to a heterologous sequence that was produced by PCR amplification, and the resultant molecule may be manipulated by addition of synthetic restriction endonuclease sites, linkers etc for cloning into a particular expression vector, as is well known in the art.

Nucleic acid sequences useful for the invention include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the intended function of the nucleic acid such as encoding an anti-cancer agent or acting as a promoter for transcription thereof.

Any of the miR-21 promoter sequences used for the invention can be altered by additions, substitutions or deletions and assayed for the level of expression of sequences operably linked thereto, in cancer cells. Similarly, sequences encoding anti-cancer agents may be altered in order to manipulate any of a number of properties, such as for example the level of their toxicity, targeting capacity, in vivo stability, etc.

Sequence alterations can be generated using a variety of chemical and enzymatic methods known to those skilled in the art. For example, regions of the sequences defined by restriction sites can be deleted. Oligonucleotide-directed mutagenesis can be employed to alter the sequence in a defined way and/or to introduce restriction sites in specific regions within the sequence. Additionally, deletion mutants can be generated using DNA nucleases such as Bal31 or ExoIII and S1 nuclease. Progressively larger deletions in the regulatory sequences are generated by incubating the DNA with nucleases for longer periods of time (See, e.g., Ausubel et al., supra for a review of mutagenesis techniques).

Sequence diversity can be introduced by a variety of mutagenesis schemes known in the art. Random, non-specific methods of introducing mutations include classical in vivo mutagenesis techniques, such as exposure of entire organisms to radiation or chemical mutagens, or use of transposons. More localized mutations in microorganisms in vivo can be performed by using mutator strains of bacteria, transducing phages, episomes, or homologous recombination.

Mutations can be induced in vitro by many other methods in addition to homologous recombination and random mutagenesis, which include deletion analysis, linker mutations, reporter gene fusion, restriction/ligation assembly, oligonucleotide-directed mutagenesis, and cassette mutagenesis. PCR-based methods that can introduce sequence diversity are also available such as error-prone PCR and assembly PCR (also known as parallel PCR). Furthermore, various combinations of the above techniques have led to specialized methods which include sexual PCR (also known as DNA shuffling), recursive ensemble mutagenesis and exponential ensemble mutagenesis.

Homologous recombination occurs naturally in living cells. In eucaryotes, homologous recombination occurs at meiosis, and is thought to be one of the inherent evolutionary mechanisms. A number of patents describe the use of in vivo homologous recombination to manipulate DNA sequences (see, e.g., U.S. Pat. Nos. 5,093,257; 5,413,923; 5,521,077; 5,202,238; 5,763,240; and 6,015,708).

Means of performing random, or localized random, in vitro mutagenesis are essentially similar to those that can be used for in vivo mutagenesis, e.g., irradiation, chemical mutagens, transposon mutagenesis. Aside from random mutagenesis methods, any of various techniques by which specific mutations can be made in vitro can be considered to be a form of site-directed mutagenesis (Kendrew, J., 1994, in The Encyclopedia of Molecular Biology, Blackwell Science Inc., London). Non-PCR-based in vitro approaches to site-directed mutagenesis can be grouped generally into the categories of oligonucleotide-directed mutagenesis, methods that restructure fragments of DNA (e.g., cassette mutagenesis, gene assembly), and localized random mutagenesis (Botstein and Shortle, 1985, Science 229, 1193 1201).

Oligonucleotide-directed mutagenesis is based on the principle that an oligonucleotide encoding the desired mutation(s) is annealed to one strand of the DNA of interest and serves as a primer for initiation of DNA synthesis to produce a strand containing the mutation. Various forms of the basic technique, including single or multiple substitutions, insertions or deletions, are described by Kramer et al., 1982, Nucleic Acids Res. 10:6475 6485; Zoller and Smith, 1982, Nucleic Acids Res.10:6487 6500; Smith et al., 1982, "Site-Directed Mutagenesis", Trends in Biochem. Sci., 7:440 442; and Norris et al., 1983, Nucleic Acids Res. 11:5103 5112.

Cassette mutagenesis is characterized by replacement, typically by restriction/ligation, of a portion of the endogenous gene with a "cassette", which often is a synthetic oligonucleotide (see, e.g., Estell et al., 1985, J. Biol. Chem. 260(11):6518 6521; Wells et al., 1985, Gene 34:315 323; Beck von Bodman et al., 1986, Proc Natl Acad Sci. 83:9443 9447; Reidhaar-Olson and Sauer, 1988, Science 241:53 57; U.S. Pat. Nos. 4,894,331; 5,155,033; and 5,182,204).

Gene assembly entails the use of oligonucleotides, which can be a mixture of synthetic oligomers and fragmented native sequences. Stochastic polymerization of the oligonucleotide pool by treatment with a DNA ligase results in the assembly of novel polynucleotide sequences (see, e.g. U.S. Pat. No. 5,723,323).

Error-prone PCR is a means of randomly introducing several point mutations in a PCR product as a result of using a DNA polymerase that demonstrates low fidelity (see, e.g., Leung et al., 1989, Technique 1:1115, 1989; U.S. Pat. No. 5,223,408).

Assembly PCR describes a process whereby, using a pool of oligonucleotides, many different PCR reactions occur in parallel in the same reaction mixture, with the products of one PCR reaction priming the products of another reaction (Stemmer et al., 1995, Gene 164:49-53). The method relies on DNA polymerase, rather than DNA ligase, to build increasingly longer DNA fragments during the assembly process (see e.g., U.S. Pat. Nos. 5,605,793 and 5,830,696).

In sexual PCR, also called DNA shuffling, related but not identical DNA sequences are randomly fragmented, after which the fragments are reassembled by assembly PCR under conditions that permit homologous recombination (Stemmer, 1994, Nature 370:389 391). Repeated cycles of point mutagenesis, recombination, and selection produce in vitro molecular evolution. This process is repeated for as many cycles as necessary to obtain a desired property or function (Stemmer, 1994, Proc Natl Acad Sci. 91:10747 10751).

Recursive Ensemble Mutagenesis ("REM") is a protein engineering method that employs multiple cycles of cassette mutagenesis to identify "optimal" amino acids at targeted positions in a given protein. REM uses information gained from previous iterations of combinatorial cassette mutagenesis to search sequence space more efficiently. Through multiple rounds of optimized point mutation and recombination, rapid evolution of DNA sequences is achieved (Arkin and Youvan, 1992, Proc Natl Acad Sci. 89:7811 7815; Delagrave et al., 1993, Protein Engineering 6:327 33 1).

In exponential ensemble mutagenesis, several nucleotides are randomized in parallel to identify amino acids, at each altered position, that lead to functional proteins. The method thereby generates combinatorial libraries with a high percentage of optimized proteins. Exponential ensemble mutagenesis can be advantageous when it is desirable to change many residues simultaneously. With the greater frequency of functional mutants which is obtained by this method, entire proteins can be mutagenized combinatorially (Delagrave and Youvan, 1993, Biotechnology 11:1548 1552; U.S. Pat. No. 5,521,077).

The altered sequences created by use of any technique known in the art to introduce sequence diversity, including those disclosed herein, are evaluated for their ability to direct expression of heterologous polynucleotides in appropriate host cells, particularly miR-21-expressing cancer derived cells e.g., pancreatic carcinoma cells. It is within the scope of the present invention to use any altered miR-21 promoter sequence that can direct tumor-specific expression to create a recombinant expression vector.

Synthetic methods suitable for preparing nucleic acid molecules include for example, assembly of oligonucleotides (see e.g. U.S. Pat. No. 5,583,013), or in vitro chemical synthesis using phosphotriester, phosphite or phosphoramidite chemistry and solid phase techniques such as those described in EP 266,032, or via deoxynucleoside H-phosphonate intermediates (see e.g. U.S. Pat. No. 5,705,629). In the present invention, one or more oligonucleotides may be used to prepare the various nucleic acid molecules. Various different mechanisms of oligonucleotide synthesis have been disclosed in for example, U.S. Pat. Nos. 4,659,774; 4,816,571; 5,141,813; 5,264,566; 4,959,463; 5,428,148; 5,554,744; 5,574,146, and 5,602,244.

The nucleotide sequence encoding an anti-cancer agent can be selected from those encoding a wide variety of proteins such as, but not limited to, genes encoding toxic gene products, cytostatic gene products, gene products essential for viral replication, genes encoding drug metabolizing enzymes and genes encoding inducers of apoptosis, as further described below.

The constructs of the invention may further comprise additional heterologous protein-encoding sequences in addition to those encoding the anti-cancer agent. These sequences may encode markers useful for selection or detection of cells transformed with the desired constructs in the course of cloning, propagation, manipulation, cell transfer, etc., such as, but not limited to, an enzyme or an antigenic marker. However, it is to be explicitly understood that the present invention specifically excludes constructs comprising an miR-21 promoter sequence operably linked to a nucleic acid sequence encoding a reporter protein, such as luciferase, as are known in the art.

Although the present invention relates to cell-specific expression of heterologous polynucleotides to target cancer cells, greater specificity of treatment can be achieved by using cancer-specific delivery of the vectors of the invention. For example, antibodies that recognize cell surface antigens unique to cancer cells, or that are more prevalent on cancer cells, compared to normal cells are known in the art, and can be used together with a vector of the invention to specifically target and kill tumor cells (See, e.g., Dillman, "Antibody Therapy: Principles of Cancer" Oldham (ed.), Raven Press, Ltd., New York, 1987). Accordingly, constructs according to the invention may include nucleic acid sequences encoding antibodies or antigen binding fragments thereof that can serve to target the anti-cancer agent to the target cancer cell. In particular embodiments, the construct encodes a fusion protein, i.e. a single protein comprising heterologous protein segments, in which one segment is the anti-cancer agent, and the other segment is an antibody or antibody fragment which is specific for a cancer-specific marker or a cancer-related protein.

The nucleic acid constructs of the invention may be comprised in a vector, in particular a eukaryotic expression vector. In particular embodiments, a vector useful for the invention may have the nucleic acid sequence of SEQ ID NO: 9 or SEQ ID NO: 10.

The term "vector" is used to refer to a carrier nucleic acid molecule into which a nucleic acid sequence or construct can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). The vectors of the present invention may include sequences which render the vector suitable for replication and integration in a particular type of host cells, for example, prokaryotes or eukaryotes, or they may be capable of propagation in more than one type of host e.g. shuttle vectors which may be propagated in both prokaryotes and eukaryotes.

Vectors suitable for cultivation of the subject polynucleotides in bacterial cells (e.g., *E. coli*), include, but are not limited to, plasmids of the types: pBR322-derived plasmids, pEMBL-derived plasmids, pEX-derived plasmids, pBTac-derived plasmids, and pUC-derived plasmids. For replication in yeast, cloning and expression vehicles useful for introducing genetic constructs in *S. cerevisiae* include, but are not limited to, the YEP24, YIPS, YEP51, pYES2 and YRP17 plasmids (See, e.g., Broach et al., 1993, in Experimental Manipulation of Gene Expression, ed. M. Inouye, Academic Press, p. 83). These vectors can replicate in *E. coli* due to the presence of the pBR322 ori, and in yeast due to the replication determinant of the yeast 2 μm circle plasmid. In addition, drug-resistant markers such as ampicillin can be used.

Similarly, mammalian vectors for the polynucleotides of the invention may comprise prokaryotic sequences to facilitate the propagation of the vector in bacteria. Such vectors, when transfected into mammalian cells, can be designed to integrate into the mammalian chromosome for long-term stability using a linked selectable marker gene. Alternatively, derivatives of viruses such as the bovine papillomavirus (BPV-1) or Epstein-Barr virus can be used for transient expression The term "expression vector" refers to a vector containing a nucleic acid sequence coding for at least part of a gene product capable of being transcribed. Expression vectors can contain a variety of "control sequences," which refer to nucleic acid sequences necessary for the transcription and translation of an operably linked coding sequence in a particular host organism. In addition to control sequences that govern transcription and translation, vectors and expression vectors may contain nucleic acid sequences that serve other functions as well.

Control sequences typically found in expression vectors include transcription and translation initiation sequences, transcription and translation terminators, and a polyadenylation signal.

Enhancer elements can augment transcription up to 1,000-fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase RNA stability. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Exemplary termination and polyadenylation signals that are suitable for the present invention include those derived from SV40.

It is to be understood that while the miR-21 promoter sequence according to the invention may comprise at least some of the aforementioned elements, the construct or vector which comprises the miR-21 promoter sequence may contain additional types of such elements. In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

In certain embodiments of the invention, the expression vector comprises a virus or an engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (see e.g. Nicolas and Rubenstein, Biotechnology. 1988; 10:493-513; Baichwal and Sugden, Oncogene. 1988 May; 2(5):461-7; Gélinas and Temin Proc Natl Acad Sci USA. 1986 December; 83(23):9211-5; Coupar et al., Gene. 1988 Aug. 15; 68(1):1-10). Nucleic acid constructs can be inserted into a viral vector, such as, but not limited to, a papovavirus, a retrovirus, an adenovirus, an adeno-associated virus, a vaccinia virus or a herpesvirus (for review, see for example *Viral Vectors: Gene Therapy and Neuroscience Applications*, Kaplitt and Loewy (eds.), Academic Press, San Diego (1995)).

The infection spectrum of viruses and viral-based vectors can be limited by modifying the viral packaging proteins on the surface of the viral particle (See, e.g., PCT publications WO93/25234 and WO94/06920). Strategies for modifying the infection spectrum of retroviral vectors include, but are not limited to, coupling antibodies specific for cell surface antigens to the viral env protein (Roux et al., 1989, Proc. Nat. Acad Sci. USA 86:9079 9083; Julan et al., 1992, J. Gen. Virol. u3:3251 3255; Goud et al., 1983, Virology 163:251 254) or coupling cell surface receptor ligands to the viral env proteins (Neda et al., 1991, J. Biol. Chem 266:14143 14146). Coupling can be in the form of chemical crosslinking with a protein or other compound (e.g., lactose to convert the env protein to an asialogycoprotein), or in the form of fusion proteins (e.g., single-chain antibody/env fusion proteins). Accordingly, cancer cells can be targeted to the surface of a recombinant virus by using, for example, coupling antibodies that are directed against tumor-associated molecules, or by using cancer cell surface proteins. Such techniques, while useful for limiting, or otherwise directing, the infection to certain tissue types, can also be used to convert an ectotropic vector into an amphotropic vector.

In a particular embodiment, an adenovirus-derived vector may be used in the present invention. The genome of an adenovirus can be manipulated such that it encodes and expresses a gene product of interest, but is inactivated in terms of its ability to replicate in a normal lytic viral life cycle (see, e.g., Berkner et al., 1988, BioTechniques 6:616; Rosenfeld et al., 1991, Science 252:431 434; Rosenfeld et al., 1992, Cell 68:143 155). Suitable adenoviral vectors derived from the adenovirus strain AD type 5 d1324 or other strains of adenovirus (e.g., Ad2, Ad3, Ad7, etc.), are well known to those skilled in the art.

Recombinant adenoviruses can be advantageous in certain circumstances in that they can be used to infect a wide variety of cell types, including airway epithelium (Rosenfeld et al., 1992, Cell 68:143 155), endothelial cells (Lemarchand et al., 1992, Proc Natl Acad Sci. 89:6482 6486), hepatocytes (Herz and Gerard, 1993, Proc Natl Acad Sci. 90:2812 2816), and muscle cells (Quantin et al., 1992, Proc Natl Acad Sci. 89:2581 2584). Furthermore, the virus particle is relatively stable, amenable to purification and concentration, and can be modified so as to affect the spectrum of infectivity.

Additionally, introduced adenoviral DNA (and foreign DNA contained therein) is generally not integrated into the genome of a host cell but remains episomal, thereby avoiding potential problems (e.g., insertional mutagenesis) that can occur when introduced DNA (e.g., retroviral DNA) becomes integrated into the host genome.

Moreover, the carrying capacity of the adenoviral genome for foreign DNA is large (up to 8 kilobases) relative to other gene delivery vectors (Berkner et al., 1988, BioTechniques 6:616; Haj-Ahmand and Graham, 1986, J. Virol. 57:267). A replication-defective adenoviral vector useful for the methods of the invention may have all or part of the viral E1 and E3 genes deleted, but retains as much as 80% of the adenoviral genetic material (see, e.g., Jones et al., 1979, Cell 16:683; Berkner et al., supra; Graham et al. in Methods in Molecular Biology, Vol. 7, E. J. Murray (ed.), Humana, Clifton N.J. (1991) pp. 109-127).

Adeno-associated virus (AAV) can also be used in accordance with the present invention (see, e.g., Walsh et al., 1993, Proc. Soc. Exp. Biol. Med. 204:289-300; U.S. Pat. No. 5,436, 146). Adeno-associated virus is a naturally occurring defective virus that requires another virus, such as an adenovirus or a herpes virus, as a helper virus for efficient replication and a productive life cycle (see, e.g., Muzyczka et al., 1992, Curr Top Microbiol Immunol. 158:97-129). Also, AAV is one of the few viruses that can integrate its DNA into non-dividing cells, and exhibits a high frequency of stable integration (see, e.g., Flotte et al., 1992, Am J Respir Cell Mol Biol. 7:349 354; Samulski et al., 1989, J. Virol. 63:3822 3828; McLaughlin et al., 1989, J. Virol. 63:1963 1973).

Vectors containing as few as 300 base pairs of AAV can be packaged and can integrate. The capacity for the insertion of exogenous DNA is limited to about 4.5 kb. An AAV vector such as that described in Tratschin et al. (1985, Mol. Cell. Biol. 5:3251-3260) can be used to introduce DNA into cells. A variety of nucleic acids have been introduced into different cell types using AAV vectors (see, e.g. Hermonat et al., 1984, Proc Natl Acad Sci. 81:6466-6470; 15 Tratschin et al., 1985, Mol. Cell. Biol. 4:2072-2081; Wondisford et al., 1988, Mol. Endocrinol. 2:32 39; Tratschin et al., 1984, J. Virol. 51:611-619; Flotte et al., 1993, J. Biol. Chem. 268:3781-3790).

Mammalian expression vectors which may serve as vector backbone for the constructs of the present invention include, but are not limited to, pcDNA3, pcDNA3.1 (+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, available from Invitrogen®; pCI available from Promega®, pMbac, pPbac, pBK-RSV and pBK-CMV, available from Strategene®; and pTRES, available from Clontech®.

Other exemplary vectors include pSVT7 and pMT2 (derived from SV40); pBV-1MTHA (derived from bovine papilloma virus); pHEBO and p2O5; (derived from Epstein-Barr virus); pMSG; pAV009/A$^+$; pMTO10/A$^+$; pMAMneo-5, and baculovirus pDSVE.

Host cells transfected with vectors of the invention can be any prokaryotic or eukaryotic cell. Transforming or transfecting the vector into host cells, either eukaryotic (e.g., yeast, avian, insect or mammalian) or prokaryotic (e.g., bacterial cells) are standard procedures used widely in the microbial or tissue-culture technologies.

Methods suitable for nucleic acid delivery to effect expression of anti-cancer agents according to the present invention include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (see e.g. U.S. Pat. Nos. 5,994, 624, 5,981,274, 5,945,100, 5,780,448, 5,736,524, 5,702,932, 5,656,610, 5,589,466 and 5,580,859), including microinjection (U.S. Pat. No. 5,789,215); by electroporation (U.S. Pat. No. 5,384,253); by calcium phosphate precipitation (Chen and Okayama, Mol. Cell Biol., 7(8):2745-2752, 1987); by using DEAE-dextran followed by polyethylene glycol (Gopal, Mol. Cell Biol., 5:1188-1190, 1985); by direct sonic loading (Fechheimer et al., Proc. Natl. Acad Sci. USA, 84:8463-8467, 1987); by liposome mediated transfection (Nicolau and Sene, Biochim. Biophys. Acta, 721:185-190, 1982; Kaneda et al., Science, 243:375-378, 1989; Kato et al, J. Biol. Chem., 266:3361-3364, 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880; by agitation with silicon carbide fibers (U.S. Pat. Nos. 5,302,523 and 5,464,765); by *Agrobacterium*-mediated transformation (U.S. Pat. Nos. 5,591,616 and 5,563,055); or by PEG-mediated transformation of protoplasts (U.S. Pat. Nos. 4,684,611 and 4,952,500; by desiccation/inhibition-mediated DNA uptake (Potrykus et al., Mol. Gen. Genet., 199(2):169-77, 1985). Through the application of techniques such as these, organelle(s), cell(s), tissue(s) or organism(s) may be stably or transiently transformed.

Nucleic Acid Sequences Encoding Anti-Cancer Agents

The nucleotide sequence encoding an anti-cancer agent can be selected from those encoding a wide variety of proteins such as, but not limited to, cytotoxic gene products, cytostatic gene products, viral replication proteins, drug metabolizing enzymes and inducers of apoptosis.

The anti-cancer agent may be a toxin, such as a bacterial toxin, a plant toxin, or a fungal toxin, either the full-length protein, but more preferably a cytotoxic fragment of a naturally occurring toxin. Exemplary bacterial toxins include, but are not limited to, diphtheria toxin, such as diphtheria toxin fragment A (DT-A), *Pseudomonas* exotoxin (PE), cholera toxin, anthrax toxin, botulinum toxin, pertussis toxin, *E. coli* enterotoxin, and shiga toxin. Exemplary plant toxins include, but are not limited to, ricin, modeccin, abrin, volkensin and viscumin. Examples of fungal toxins include α-sarcin (see for example, Nagano et al., J Antibiot (Tokyo). 1996 January; 49(1):81-5); restrictocin (see e.g., Rathore et al FEBS Lett 2 Sep. 1996, 392(3):259-262); mitogillin (see e.g., Better et al., J Biol Chem Aug. 15; 1992 267, 16712-16718); enomycin (see e.g., Takeuchi et al., J Antibiot (Tokyo). 1997 January; 50(1):27-31); a fungal ribotoxin, for example RNase T1 (for review see e.g., Lacadena et al., FEMS Microbiol Rev. 2007 March; 31(2):212-37) and phenomycin (see e.g., Sakata et al., J Antibiot (Tokyo). 1994 March; 47(3):370-1).

The toxin for use in the invention may be the A chain of a ricin-like protein, as disclosed for example in U.S. Pat. No. 7,375,186.

A diphtheria toxin for use in the invention may correspond to the full-length 535 amino acid polypeptide secreted by Corynbacterium diphtheria or it may be a cytotoxic fragment thereof, in particular fragment A comprising the N-terminal catalytic domain (see, e.g., Genbank Accession Nos. A04646 and AY820132; Greenfield et al., 1983 Proc. Natl. Acad Sci. USA 80:6853-6857; Tweten et al., 1983 J. Bacteriol. 156: 680-685; Kaczorek et al., 1983 Science 221:855-858; Leong et al., 1983 Science 220:515-517).

Examples 3 and 4 herein disclose a construct comprising a nucleic acid sequence encoding diphtheria toxin fragment A operably linked to a miR-21 promoter sequence and its cytotoxic effect on cancer cells in vitro and in vivo.

In a particular embodiment, a nucleic acid sequence encoding a diphtheria toxin comprises SEQ ID NO: 18. In a particular embodiment, the construct encodes a diphtheria toxin comprising an amino acid sequence of SEQ ID NO: 19.

In other embodiments, a nucleic acid sequence encoding a *Pseudomonas* exotoxin (PE) may be used in the invention, for example that corresponding to the full-length protein of 613 amino acids secreted by *Pseudomonas aeruginosa*, or that encoding a cytotoxic fragment thereof, such as a cytotoxic fragment corresponding to domain III i.e. amino acid residues 400-613 (see, e.g., U.S. Pat. No. 5,602,095; Siegall et al., J. Biol. Chem. 264:14256-14261, 1989). Other forms of PE which may be encoded and expressed by the constructs of the invention include for example, PE38 (see e.g., U.S. Pat. No. 5,608,039, and Pastan et al., 1997, Biochim. Biophys. Acta 1333:C1-C6), disclosed herein as SEQ ID NO: 21; PE38 KDEL (see e.g., Brinkmann et al 1991, Proc Nat Acad Sci USA 88:8616-8621), disclosed herein as SEQ ID NO: 22; PE37 (see e.g., U.S. Pat. No. 5,602,095) disclosed herein as SEQ ID NO: 23; and PE40 (see e.g., U.S. Pat. No. 6,051,405) disclosed herein as SEQ ID NO: 24.

The invention further encompasses use of a nucleic acid encoding a drug-metabolizing enzyme which converts a prodrug into a cytotoxic product.

In a particular embodiment, the drug-converting enzyme is a thymidine kinase (e.g. from herpes simplex virus or varicella zoster virus), which has the capacity to convert the prodrug form of ganciclovir (2-amino-9-{[(1,3-dihydroxypropan-2-yl)oxy]methyl}-6,9-dihydro-3H-purin-6-one) into its active phosphorylated form, which is a deoxyguanosine triphosphate (dGTP) analog. This analog competitively inhibits the incorporation of dGTP into cellular DNA, resulting in cell death.

Drug metabolizing enzymes that convert a prodrug into a cytotoxic product include, but are not limited to, thymidine kinase (e.g. from herpes simplex virus or varicella zoster virus), cytosine deaminase, nitroreductase, cytochrome p-450 2B1, thymidine phosphorylase, *E. coli* guanine phosphoribosyl transferase, purine nucleoside phosphorylase, alkaline phosphatase, carboxypeptidases A and G2, linamarase, beta-lactamase, xanthine oxidase, and variants thereof (see, e.g., Pandha et al., 1999, J Clin Oncol. 17:2180 2189; Rigg and Sikora, 1997, Mol Med Today. 3:359 366).

The anti-cancer agent may further be an inducer of apoptosis, such as PUMA (see, e.g. GenBank accession No. AF354654); BAX (see, e.g. GenBank accession No. AY217036); BAK (see, e.g. GenBank accession No. NR_027882); Bcl-XS (see, e.g. GenBank accession No. NM_001191); BAD (see, e.g. GenBank accession No. BCO01901); BIM (see, e.g. GenBank accession No. BC033694); BIK (see, e.g. GenBank accession No. U34584); BID (see, e.g. GenBank accession No. BC036364); HRK (see, e.g. GenBank accession No. HSU76376); Ad E1B; ICE-CED3 proteases (see, e.g. GenBank accession Nos. NM_001080124 and NP_001073593); TRAIL (see, e.g. GenBank accession Nos. NM_003810 and NP_003801); SARP-2 (see, e.g. GenBank accession Nos. NM_003012 and NP_003003); and apoptin (see, e.g. GenBank accession Nos. NM_012234 and NP_036366).

Oligonucleotide sequences useful for preparing nucleic acid sequences encoding such apoptosis inducers are disclosed for example in U.S. Patent Application publication No. 2009/0298071.

Examples 3 and 4 herein discloses construction and use of a construct and vector comprising a sequence encoding PUMA for use in anti-cancer therapy.

Polynucleotides encoding cytostatic agents that suppress cell growth and multiplication are useful for the invention. These include, but are not limited to, gene products derived from p21 (Waf1), p27 (Kip1), p53, p53175P, p57 (Kip2), p15 (INK4b), p16 (INK4a), p18(INK4c), p19(Arf), p73, GADD45, APC1, p73RB1, WT1, NF1, VHL, and variants thereof (see e.g., Koga et al., Hepatology. 33:1087 1097; Huang et al., 2001, Cancer Res. 61:3373 3381; Li et al., 2001, Cancer Res. 61:1493 1499; Mazur et al., 1998, Biotechnol Prog. 14:705 713; Tsugu et al., 2000, Am J Pathol. 157:919 932; Dyer et al., 2001, J Neurosci. 21:4259 4571; Kovalev et al., 2001, J Immunol. 167:3285 3292; Modesitt et al., 2001, Clin Cancer Res. 7:1765 1772; Wong et al., 2001, J Pathol. 194:35 42; Shapiro et al., 2000, Cell Biochem Biophys. 33:189 197; Fuxe et al., 2000, Cell Growth Differ. 11:373 384; Latres et al., 2000, EMBO J. 19:3496 3506; Weber et al., 2000, Genes Dev. 14:2358 2365; Sasaki et al., 2001, Gene Ther. 8:1401 1408; Zhu et al., 1998, Cancer Res. 58:5061 5065; Mullan et al., 2001, Oncogene. 20:6123 6131; Velasco-Miguel et al., 1999, Oncogene. 18:127 137; Jorgensen et al., 2001, Gene. 262:51 59; Kurasawa and Todokoro, 1999, Oncogene 18:5131 5137; Basu et al., 1999, Int J. Oncol. 15:701 708; Yamagami et al., 1998, Leuk Res. 22:383 384; Murata et al., 1997, FEBS Lett. 409:41 45; Uhlmann et al., 2001, Cell Biochem Biophys. 34:61 78; Zhang et al., 1998, J Exp Med. 187:1893 1902; Norton et al., 1996, Neuroreport. 7:601 604; Baba et al., 2001, Oncogene. 20:2727 2736; Davidowitz et al., 2001, Mol Cell Biol. 21:865 874).

Pharmaceutical Compositions, Formulations and Modes of Administration

The nucleic acid constructs and vectors of the invention may be administered to a subject alone or in the form of a pharmaceutical composition. Pharmaceutical compositions may be formulated in conventional manner using one or more physiologically acceptable carriers, diluents, excipients or auxiliaries which facilitate processing of the nucleic acids into preparations which can be used pharmaceutically. Proper formulation is dependent upon the route of administration chosen.

Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. For injection, the nucleic acids of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the nucleic acid molecules may be in powder form for reconstitution with a suitable vehicle, e.g., sterile pyrogen-free water, before use. For transmucosal administration, penetrants appropriate to the barrier to be permeated are used in the formulation. For administration by inhalation, the molecules for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the nucleic acids and a suitable powder base such as lactose or starch. The nucleic acid molecules may also be formulated in rectal or vaginal compositions such as suppositories or retention enemas, e.g., containing conventional suppository bases such as cocoa butter or other glycerides. For oral administration, the nucleic acids can be readily formulated by combining the molecules with pharmaceutically acceptable carriers well known in the art. Such carriers enable the nucleic acids of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the molecules may take the form of tablets, lozenges, etc. formulated in conventional manner.

The nucleic acid molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt.

A nucleic acid of the invention may be administered in combination with a carrier or lipid to increase cellular uptake. For example, nucleic acids may be administered in combination with a cationic lipid. Examples of cationic lipids include, but are not limited to, Lipofectin®, DOTMA, DOPE, and DOTAP, and T-shaped cholesterol ester derivative (see e.g. Lee et al Biorg Med Chem Lett 14 (2004):2637-2641. Various nucleic acid formulations and methods of administration are disclosed for example in U.S. Pat. Nos. 7,470,675; 5,844,107; 5,877,302; 6,008,336; 6,077,835; 6,200,801, and 5,972,900, and in U.S. Patent Application Publication Nos. 2003/0203865; 2002/0150626; 2003/0032615, and 2004/0048787.

In addition, liposomes and emulsions are well-known examples of delivery vehicles that may be used to deliver nucleic acids of the invention. Suitable liposomes can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, described example, in Szoka et al. (1980), Ann. Rev. Biophys. Bioeng. 9:467; and U.S. Pat. Nos. 4,235,871, 4,501,728, 4,837,028, and 5,019,369.

Liposomes for use in the present methods can comprise a ligand molecule that targets the liposome to cancer cells, for example a monoclonal antibody that binds a tumor cell antigen.

can also be modified so as to avoid clearance by the mononuclear macrophage system ("MMS") and reticuloendothelial system ("RES"). Such modified liposomes have opsonization-inhibition moieties on the surface or incorporated into the liposome structure. In a particular embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016.

Examples of opsonization-inhibiting moieties suitable for modifying liposomes are water-soluble polymers with a number-average molecular weight from about 500 to about 40,000 daltons, such as about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof Liposomes modified with PEG or PEG-derivatives are sometimes called "PEGylated liposomes."

An opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al. (1988), Proc. Natl. Acad Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the or nucleic acids of the invention to tumor cells.

The nucleic acids may also be administered in combination with a cationic amine such as poly (L-lysine). Nucleic acids may also be conjugated to a chemical moiety, such as transferrin and cholesteryls. In addition, oligonucleotides may be targeted to certain organelles by linking specific chemical groups to the oligonucleotide. For example, linking the oligonucleotide to a suitable array of mannose residues will target the oligonucleotide to the liver.

Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Nucleic acids may be included in any of the above-described formulations as the free acids or bases or as pharmaceutically acceptable salts. Pharmaceutically acceptable salts are those salts that substantially retain the biologic activity of the free bases and which are prepared by reaction with inorganic acids. Pharmaceutical salts tend to be more soluble in aqueous and other protic solvents than are the corresponding free base forms.

Pharmaceutical compositions of the present invention comprise an effective amount of one or more nucleic acid molecules or vectors dissolved or dispersed in a pharmaceutically acceptable carrier. The phrases "pharmaceutically acceptable" refers to molecular entities and compositions that do not produce an adverse, allergic or other untoward reaction when administered to an animal, such as, for example, a human, as appropriate. The preparation of a pharmaceutical composition that contains at least one nucleic acid ingredient will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by health regulatory agencies such as the FDA Office of Biological Standards.

As used herein, "pharmaceutically acceptable carrier, diluent or excipient" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

The pharmaceutical compositions comprising nucleic molecules may comprise different types of carriers depending on whether it is to be administered in solid, liquid or aerosol form, and in accordance with the general need for sterility for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in lipid compositions (e.g., liposomes), or by other method or any combination of the forgoing as would be known to one of ordinary skill in the art.

The actual dosage amount of a composition of the present invention administered to the subject, such as a human patient, can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from at least about 1 microgram/kg/body weight, including about 5, about 10, about 50, about 100, about 200, about 350 weight, about 500 microgram/kg/body weight; or at least about 1 milligram (mg)/kg/body weight, such as about 5, about 10, about 50, about 100, about 200, about 350, about 500, to about 1000 mg/kg/body weight or more per administration, and any range derivable therein.

The composition may comprise various antioxidants to retard oxidation of one or more component. Additionally, the composition may comprise preservatives such as various antibacterial and antifungal agents, including but not limited to parabens (e.g., methylparabens, propylparabens), chlorobutanol, phenol, sorbic acid, thimerosal or combinations thereof.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

Therapeutic Uses and Methods of Treatment

The nucleic acid constructs and vectors of the invention may be used for treating a subject having cancer, such as for inhibiting tumor progression, for inhibiting tumor metastasis, or for reducing or alleviating a symptom associated with a neoplastic disorder.

The invention is particularly useful for treating types of cancer, tumors or neoplastic disorders characterized inter alia by endogenous expression of miR-21 in at least a portion of the cells thereof.

The cancer, tumor or neoplastic disorder may be a sarcoma, a carcinoma, an adenocarcinoma, a lymphoma, and a leukemia. Included within the scope of the invention are breast cancer, colon cancer, hepatocellular carcinoma, cervical cancer, cholangiocarcinoma, endometrioid ovarian carcinoma, esophageal cancer, glioblastoma, head and neck cancer, leukemia (e.g. chronic lymphocytic leukemia), lymphoma (e.g. diffuse large B cell lymphoma, activated B cell-like lymphoma), lung cancer, multiple myeloma, pancreatic (e.g. endocrine and acinar) cancer, osteosarcoma, pituitary tumor, prostate cancer, stomach cancer, and uterine leiomyoma.

The constructs and vectors of the invention treat cancer by inhibiting cancer cell proliferation, and/or by arresting or slowing the growth of the cancer cells and/or by inhibiting tumor progression, and/or by inhibiting tumor metastasis. Any of the aforementioned effects may be permanent or temporary. Inhibition of cancer cell proliferation can be inferred if the number of such cells in the subject remains constant or decreases after administration of the constructs and vectors. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

Any mode of administration of the constructs and vectors can be used so long as it results in the expression of the anti-cancer agent in the desired tissue, in an amount sufficient to be therapeutically and/or prophylactically effective. The miR-21 promoter containing constructs and vectors can be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material e.g. gelfoam sponge depots; hydrogels) or topical applications during surgery; and inhalation. Particularly suitable administration routes are injection, infusion and direct injection into the tumor.

Means of injection include biolistic injectors and particle accelerators (e.g., "gene guns" or pneumatic "needleless" injectors), such as those marketed as Med-E-Jet™ (Vahlsing, H., et al., J. Immunol. Methods 171, 11-22 (1994)), Biojector™ (Davis, H., et al., Vaccine 12, 1503-1509 (1994); Gramzinski, R., et al., Mol. Med. 4, 109-118 (1998)), AdvantaJet™ (Linmayer, I., et al., Diabetes Care 9:294-297 (1986)), and Medi-Jector™ (Martins, J., and Roedl, E. J. Occup. Med. 21:821-824 (1979)).

The nucleic acid constructs and vectors may be administered as a single dose or multiple doses, administered at suitable time intervals.

The term "therapeutically effective amount" refers to an amount of a construct or vector of the invention that is effective to achieve the desired result following administration.

The constructs and vectors may be administered in conjunction with one or more additional modalities of cancer therapy including, but not limited to bone marrow transplant, cord blood cell transplant, surgery, chemotherapy, radiation therapy, and immunotherapy. The polynucleotide construct or pharmaceutical composition of the present invention can be administered prior to the commencement of one or more of the additional cancer therapies, during the practice of one or more of the additional modalities of cancer therapy, and after the end of one or more of the additional modalities of cancer therapy.

Types of bone marrow transplant include, but are not limited to autologous bone marrow transplant and heterologous (i.e., from a donor) bone marrow transplant.

Chemotherapeutic agents include, but are not limited to alkylating agents, including mechlorethamine, cyclophosphamide, ifosfamide, melphalan, chlorambucil, dicarbazine, streptazocine, carmustine, lomustine, semustine, chlorozotocin, busulfan, triethylenemelamine, thiotepa, hexamethylmelamine; antimetabolites, including methotrexate; pyrimidine analogs, including fluorouracil, 5-fluorouracil, floxuridine (5'-fluoro-2'-deoxyuridine), idoxuridine, cytarabine, N-phosphonoacetyl-L-aspartate, 5-azacytidine, azaribine, 6-azauridine, pyrazofuran, 3-deazauridine, acivicin; purine analogs, including thioguanine, mercaptopurine, azathioprine, pentostatin, erythrohydroxynonyladenine; vinca alkaloids, including vincristine and vinblastine; epipodophyllotoxins, including etoposide and teniposide; antibiotics, including dactinomycin, daunorubicin, doxorubicin, bleomycin sulfate, plicamycin, mitomycin; enzymes, including L-asparaginase; platinum coordination complexes, including cisplatin, carboplatin; hydroxyurea, procarbazine, mitotane; and hormones or related agents, including adrenocorticosteroids such as prednisone and prednisolone; aminoglutethimide; progestins such as hydroxyprogesterone caproate, medroxyprogesterone acetate, megesterol acetate, estrogens and androgens such as diethylstilbestrol, fluoxymesterone, ethynyl estradiol, antiestrogens such as tamoxifen, and gonadotropin-releasing hormone analogs such as leuprolide.

The methods of the invention may further comprise a step of determining the level of miR-21 transcriptional activity in a biological sample e.g. cells or tissue, from the subject. The presence or level of at least one miR-21 gene product in the sample may be indicative that the cancer or tumor or neoplasm is treatable by the methods of the invention.

The level of a miR-21 gene product can be measured in a biological sample obtained from the subject. For example, a tissue sample can be removed from a subject suspected of having breast cancer by conventional biopsy techniques. In another example, a blood sample can be removed from the subject, and white blood cells can be isolated for DNA extraction by standard techniques. The blood or tissue sample is preferably obtained from the subject prior to initiation of treatment according to the invention or any other type of intervention such as radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR-21 gene product produced from a miR-21 gene in cells from the subject's sample can be compared to the corresponding miR-21 gene product levels from cells of the control sample.

Some cancers are characterized by an alteration, particularly an increase, in the level of an miR-21 gene product in a sample obtained from the subject, relative to the level of a corresponding miR-21 gene product in a control sample. When the level of at least one miR-21 gene product in the test sample is greater than the level of the corresponding miR-21 gene product in the control sample, the expression of the miR-21 gene product is "up-regulated".

The relative miR-21 gene expression in the control and normal samples can be determined with respect to one or more RNA expression standards. The standards can comprise, for example, a zero miR-21 gene expression level, the miR-21 gene expression level in a standard cell line, or the average level of miR-21 gene expression previously obtained for a population of normal human controls.

The level of a miR-21 gene product in a sample can be measured using any technique that is suitable for detecting RNA expression levels in a biological sample. Suitable techniques for determining RNA expression levels in cells from a biological sample (e.g., Northern blot analysis, RT-PCR, in situ hybridization) are well known to those of skill in the art. In a particular embodiment, the level of at least one miR-21 gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Sambrook et al., supra Chapter 7.

Suitable probes for Northern blot hybridization of a given miR-21 gene product can be produced from their known nucleic acid sequences, as disclosed herein and in publicly available databases. Methods for preparation of labeled DNA and RNA probes, and the conditions for hybridization thereof to target nucleotide sequences, are described in Sambrook et al., supra.

Probes can be labeled for example with a radionuclide, a heavy metal; a ligand capable of functioning as a specific binding pair member for a labeled ligand (e.g., biotin, avidin or an antibody), a fluorescent molecule, a chemiluminescent molecule, an enzyme or the like, to high specific activity using methods well known in the art. Autoradiographic Detection of hybridization is performed by a means appropriate for the labeling entity e.g. autoradiography for radiolabeled probes; reacting biotinylated probes with biotin-binding proteins that produce color reactions.

In situ hybridization involves depositing whole cells onto a microscope cover slip and probing the nucleic acid content of the cell with a solution containing radioactive or otherwise labeled nucleic acid probes. This technique is particularly well-suited for analyzing tissue biopsy samples from subjects (see e.g. U.S. Pat. No. 5,427,916).

The relative number of miR-21 gene transcripts in cells can also be determined by reverse transcription of miR-21 gene transcripts, followed by amplification of the reverse-transcribed transcripts by polymerase chain reaction (RT-PCR). The levels of miR-21 gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). The methods for quantitative RT-PCR and variations thereof are within the skill in the art.

In some instances, it may be desirable to simultaneously determine the expression level of a plurality of different miRNA gene products in a sample. In other instances, it may be desirable to determine the expression level of the transcripts of all known miRNA genes correlated with a cancer. Suitable microarray techniques are known in the art, as described for example in U.S. Pat. Application Publication No. 2008/0306018.

Kits

The present invention also provides kits containing compositions of the invention or compositions to implement methods of the invention. In some embodiments, the kits are for therapeutic use and contain multiple dosage units of the constructs or vectors and instructions for use for administering to a subject having cancer.

In some embodiments, the kits are for prognostic use, for example to evaluate the susceptibility of one or more miR-21 expressing target cells to the cytotoxic effects of the construct of the invention.

Individual components of the kit may be provided in concentrated amounts; in some embodiments, a component is provided individually in the same concentration as it would be in a solution with other components.

Negative and/or positive control vectors are included in some kit embodiments. The control molecules can be used to verify transfection efficiency and/or control for transfection-induced changes in cells. The kit may also include one or more transfection reagent(s) to facilitate delivery of the construct or vector to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent, provided in a separate container means.

The kits may also include components that preserve or maintain the constructs and vectors or that protect against its degradation.

A kit will also include instructions for employing the kit components as well the use of any other reagent not included in the kit. Instructions may include variations that can be implemented.

The following examples are presented in order to more fully illustrate some embodiments of the invention. They should, in no way be construed, however, as limiting the broad scope of the invention.

EXAMPLES

Example 1

Differential Expression of Endogenous miR-21 in Cancer Cells and tissues.

Table 1 summarizes the differential miR-21 expression in cancerous vs. non-cancerous tissues and cells (NS=not specified).

TABLE 1

| Tumor/cancer type | Method | Fold over expression (Mean) | Reference |
|---|---|---|---|
| Glioblastoma | Microarray, Northern blots | 10-40 | [5] |
| | real-time PCR | | [6] |
| Breast cancer | Microarray | 1.6 | [7] |
| | In situ hybridization | NS | [8] |
| | Real-time PCR | 5 | [9] |
| | Real-time PCR | NS | [10] |
| | Microarray | 2 | [11] |
| Hepatocellular carcinomas | Microarray | ~2 | [12] |
| | small RNA cloning and sequencing | 4.5 | [13] |
| | real-time PCR | >2 | [14] |
| | Microarray, real-time PCR | 10-45 | [15] |
| Cholangiocarcinoma | Northern blots and real-time polymerase chain reaction | 6-12 | [16] |
| Pancreatic endocrine and acinar tumors | Microarray | NS | [17] |
| Pancreatic cancer | Microarray | 15.7 | [18] |
| | In situ hybridization | NS | [19] |
| Lung, breast, stomach, prostate, colon, and pancreatic tumors | Microarray | NS | [20] |
| Chronic lymphocytic leukemia | miRNA cloning and real-time-PCR | ~3 | [21] |
| Osteosarcoma | miRNA cloning and real-time-PCR, Northern blots | NS | [22] |
| Endometrioid ovarian carcinoma | Microarray, Northern blots | 4 | [23] |
| Diffuse large B cell lymphoma (activated B cell-like) | Microarray | 20 | [24] [25] |

TABLE 1-continued

| Tumor/cancer type | Method | Fold over expression (Mean) | Reference |
|---|---|---|---|
| Cervical cancer | Direct sequencing | 5 | [26] |
| Multiple myeloma | NS | NS | [27] |
|  | Microarray, Real-time-PCR |  | [28] |
| Colon cancer | Real-time-PCR | 5 | [29] |
|  | Microarray | NS | [30] |
|  | Microarray | NS | [31] |
|  | Real-time-PCR | 10-70 | [32] |
| Head and neck cancer | Microarray, Northern blots | NS | [33] |
| Esophageal cancer | Microarray | 7.2 | [34] |
|  | Microarray | 3-5 | [35] |
| Uterine leiomyomas | Microarray | 1.2-5 | [36] |
| Pituitary tumors | Real-time-PCR | 2.4 | [37] |
| Lung cancer | Real time RT-PCR | NS | [38] |
| Ovarian carcinoma | Microarray, Northern blots | 3 | [39] |
| Bladder cancer | Microarray | 10 | [40] |

Example 2

Expression of Heterologous Genes Under miR-21 Promoter Control

A recombinant vector that expresses the firefly luciferase gene (Luc) under the control of a miR-21 promoter sequence (miR-21-Luc; SEQ ID NO: 11) was produced by standard recombinant procedures, as detailed herein. As a negative control, a vector containing the TATA box of the miR-21 promoter (TATA-Luc; SEQ ID NO: 20), rather than the miR-21 promoter, was prepared.

The human hepatocellular carcinoma cell line Huh7 was used as a genomic DNA template for amplification of an miR-21 promoter sequence of SEQ ID NO: 1, using the following primers: fw 5'-GGGGTACCGAAGGAGCTC-CGAGTA CATAAAT-3' (SEQ ID NO: 14) and rev 5'-CCCAAGCTTCTACTCTGGTATGGCACAAAG 3' (SEQ ID NO: 15). The PCR product was cloned into the pGL3-Basic (Promega, Madison, Wis.) vector, which carries the firefly luciferase gene.

A DNA sequence corresponding to the TATA box of the miR-21 promoter (SEQ ID NO: 6) was constructed by annealing the following oligonucleotides: fw 5'-CCTAGTGGT-GATAAATGTGGGACTTCTGAGAAGTCAT-TCATTTTATTCTTTGTGCC ATACCAGAGTACAA-3' (SEQ ID NO: 16) and 5'-TCGAAACATGAGACCATACC GTGTTTCTTATTTTACTTACTGAA-GAGTCTTCAGGGTGTAAATAGTGGTGATCCCAT G-3' (SEQ ID NO: 17). The resultant fragment was directly cloned into pGL3-Basic to yield the vector TATA-Luc (SEQ ID NO: 20)

To examine the selective expression of heterologous gene products under miR-21 promoter control in cancerous cells, miR-21-Luc and its control TATA-Luc were transfected into different transformed and untransformed cells and the luciferase expression levels of the transfected cell lines were compared.

Figure 2:
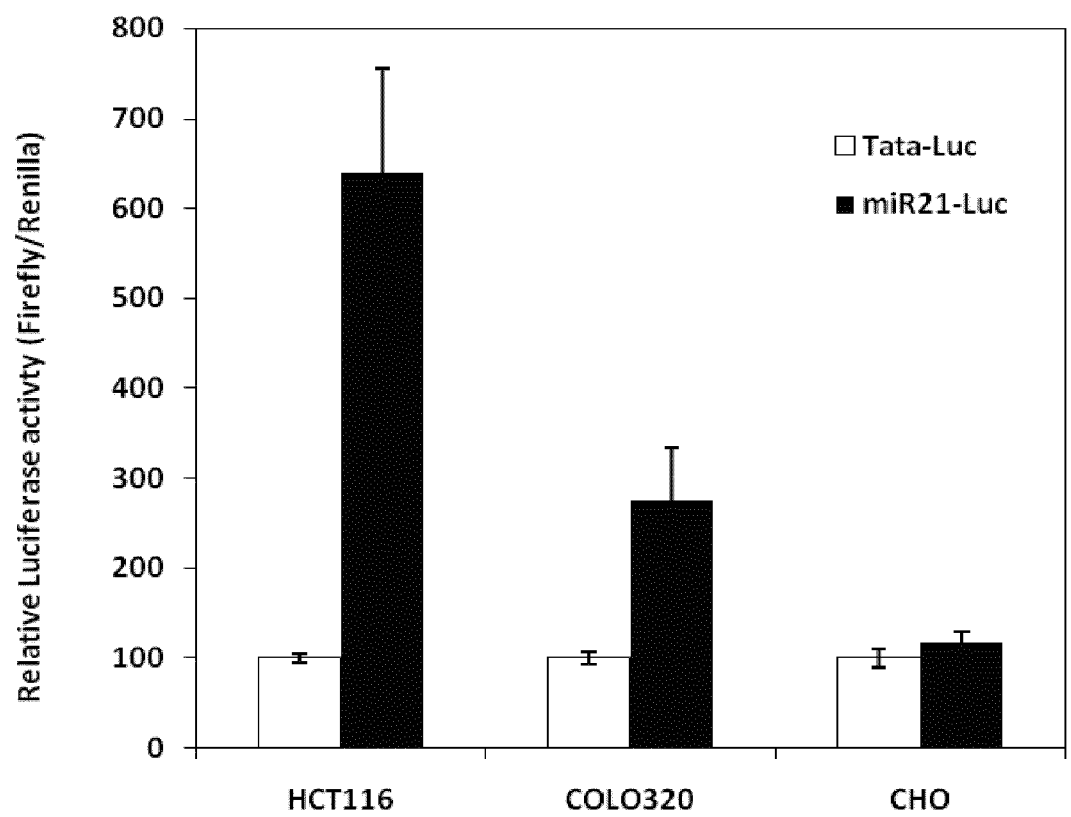
FIG. 2 demonstrates miR-21 promoter-driven expression of a reporter luciferase gene in different cell lines. A vector containing the firefly luciferase gene (Luc) under the control of the miR-21 promoter (miR-21-Luc; SEQ ID NO: 11; black bars), and a control vector containing the firefly luciferase gene under the control of the TATA box sequence of the miR-21 promoter (TATA-Luc; SEQ ID NO: 20; white bars) were each transfected into different cell lines. The cell lines tested included Chinese hamster ovary (CHO, right bars) and the human colorectal cancer cell lines HCT116 (left bars) and COLO320 (middle bars). Y axis—relative luciferase activity.

FIG. 2 demonstrates miR-21 promoter-driven expression of the luciferase gene in Chinese hamster ovary cells (CHO) and the human colorectal cancer cell lines HCT116 and COLO320. As can be seen from FIG. 2, the human cancer cell lines transfected with miR-21-Luc exhibited significantly higher expression of luciferase, as compared to the cancer cells transfected with the control vector TATA-Luc. In addition, the CHO cells transfected with either vector showed low levels of expression of luciferase, similar to the levels exhibited by the cancer cells transfected with the control vector TATA-Luc. These results indicate that heterologous gene products may be expressed at high levels in miR-21-expressing cells, such as certain cancers, using constructs encoding the heterologous gene under the control of an mir-21 promoter sequence.

Example 3 miR-21 Promoter Driven "Killer Gene" Expression

To determine the ability of regulatory promoter sequences of miR-21 to specifically drive the expression of a "killer gene", the luciferase coding regions of the reporter and control vectors described in Example 2 were replaced with a nucleic acid sequence encoding the cytotoxic fragment A of diphtheria toxin (DT-A). DT-A inhibits protein synthesis, triggers apoptosis and detachment of cells, and has been previously used as a "killer gene" for targeting cancer cells.

The DNA sequence encoding DT-A, and the corresponding amino acid sequence are provided herein as SEQ ID NO: 18 and SEQ ID NO: 19, respectively. The constructed plasmids containing the miR-21 promoter sequence of SEQ ID NO:1 or its TATA box of SEQ ID NO: 6 were respectively designated miR-21 Pr-DT-A (SEQ ID NO: 9) and miR-21 TATA box DT-A (SEQ ID NO: 13).

Figure 3:
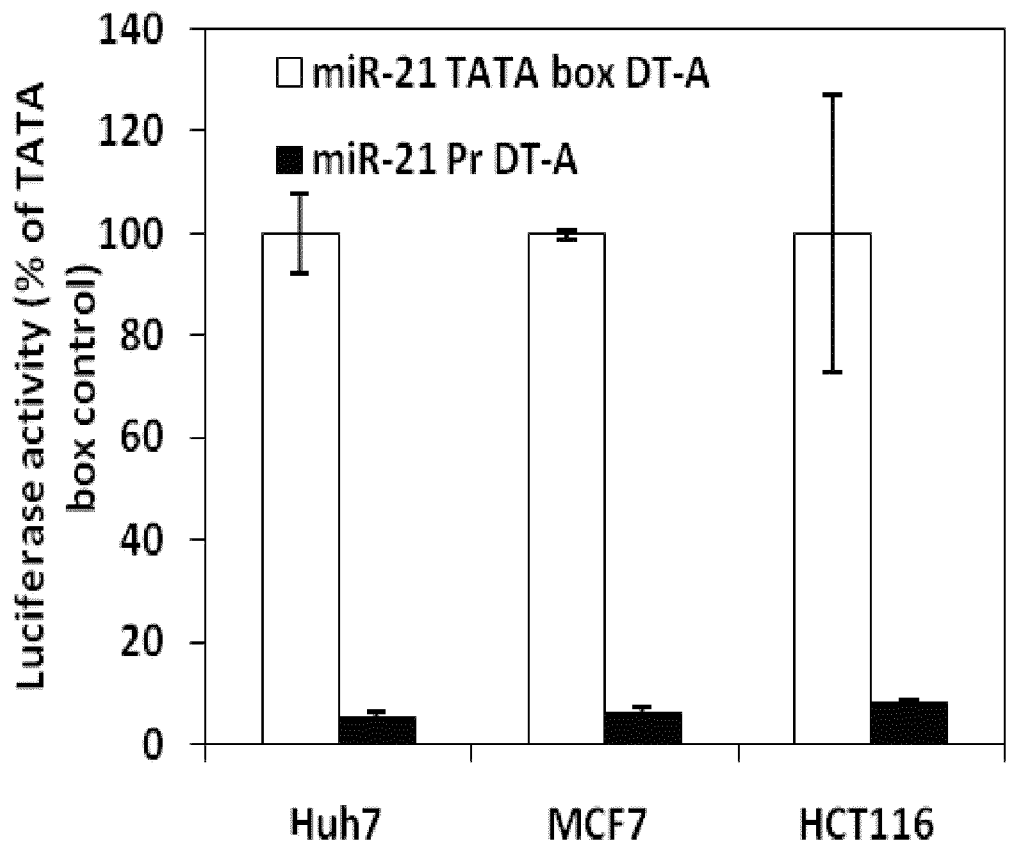
FIG. 3 demonstrates inhibition of *Renilla* luciferase expression in a model of reduction of de novo protein synthesis induced by constructs encoding a fragment of diphtheria toxin (DT-A). Cells were co-transfected with a plasmid encoding *Renilla* luciferase under the control of an SV-40 promoter (SEQ ID NO: 28) and either a plasmid encoding DT-A under the control of the miR-21 promoter (miR-21 Pr DT-A; SEQ ID NO: 9), or a plasmid encoding DT-A under the control of the TATA-box sequence of the miR-21 promoter (miR-21 TATA box DT-A (SEQ ID NO: 13). Cells were harvested 72 hours post-transfection and subjected to luciferase assay.

Apoptosis levels and protein synthesis rates were determined to confirm the miR-21 promoter-driven expression of DT-A. To determine the reduction in de novo protein synthesis, miR-21 Pr DT-A and a expression vector containing Renilla luciferase under the control of an SV-40 promoter were cotransfected into cells. As demonstrated in FIG. 3, transfectants of three different cancer cell types (Huh7, human hepatocellular carcinoma; MCF7, human breast cancer; HCT116, human colon carcinoma) containing miR-21 Pr DT-A showed strong reduction in luciferase activity, compared to the corresponding transfectants containing miR-21 TATA box DT-A, indicating the efficiency of the miR-21 promoter-driven approach.

The next set of experiments was performed using a plasmid in which the nucleic acid sequence encoding the p53 up-regulated modulator of apoptosis (PUMA) replaced the Luc sequence in the plasmids described in Example 2. Thus, the plasmid miR-21 pr PUMA (SEQ ID NO: 10), having the PUMA sequence under the control of the miR-21 promoter sequence of SEQ ID NO:1 was produced. miR-21 pr PUMA and miR-21 Pr DT-A were co-transfected into cells together with a luciferase expressing plasmid. Forty eight hours post transfection the cells were harvested and luciferase activity was determined Reduction in de novo protein synthesis by DT-A and induction of apoptosis by PUMA were observed in cells transfected with the miR-21 promoter driven plasmids, but not in cells transfected with the TATA box control plasmids (FIG. 4A).

A similar experiment was carried out in which a plasmid encoding green fluorescent protein (GFP; SEQ ID NO: 25) was co-transfected together with the miR-21 promoter driven plasmids (miR-21 Pr DT-A or miR-21 pr PUMA) or the TATA box control plasmids (miR-21 TATA box DT-A or miR-21 TATA box PUMA). After 48 hours the cells were lysed and the lysates subjected to Western blot analysis with an anti-GFP antibody (FIG. 4B). As seen in FIG. 4B, the GFP signal was completely eliminated in the cotransfection systems with miR-21 DT-A and with miR-21 PUMA, but not in the systems with the TATA box driven controls.

Example 4 miR-21 Promoter Driven DT-A Expression Inhibits Tumor Formation in Vivo

Figure 5:
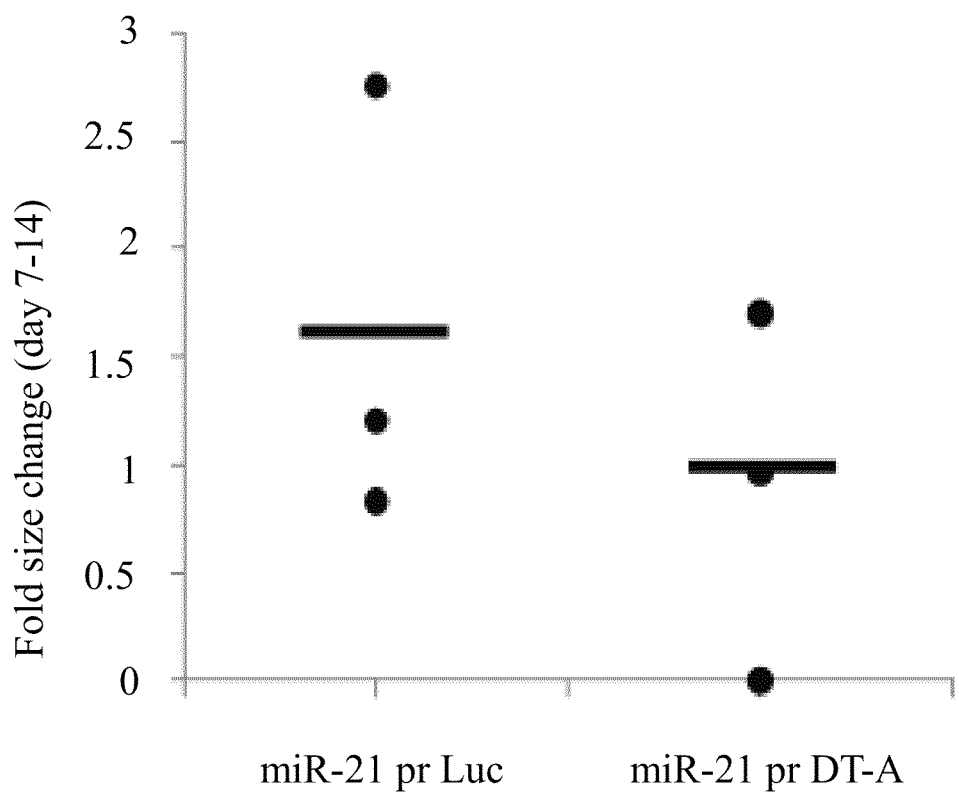
FIG. 5 demonstrates that miR-21 Pr DT-A expression inhibits tumor formation in vivo. Nude mice (n=3 per group) were injected with $1\times10^7$ HCT116 cells. Two weeks following tumor cell injection, mice were administered endotoxin-free miR-21 Pr DT-A (SEQ ID NO: 9) by intra-tumor injection (dose of 25 ug). An additional injection was administered 7 days later. Tumor size was recorded at days 0, 7 and 14 following tumor cell injection using a manual caliper. Control-treated mice were administered miR-21-Luc (SEQ ID NO: 11) by intra-tumor injection.

Nude mice (n=3 in each group) were injected with 1×107 HCT116 cells. Two weeks post injection tumor starting size was determined Two weeks following tumor cell injection, endotoxin-free miR-21 Pr DT-A (25 ug) complexed with the transfection reagent JETPEI™ (Polyplus, France) was injected intratumorly. An additional injection was administered 7 days later. Tumor size was recorded at days 0, 7 and 14 using a manual caliper. Injection of miR-21-Luc (described in Example 2) served as a control. In one mouse injected with miR-21 Pr DT-A, the tumor completely disappeared. In another mouse similarly treated with miR-21 Pr DT-A, the tumor growth was inhibited but its size was not reduced. Overall, the mean fold change for the treated mice was 1 compared to 1.6 in the control mice, as shown in FIG. 5.

In additional experiments, the expression level of miR-21 may be examined in cancer cells, such as cell lines of human hepatocellular carcinoma, colorectal cancer, and breast cancer. Particularly preferred are cancer cells which have shown to be susceptible to the cytotoxic effects of the constructs and vectors of the invention upon transfection and expression of the anti-cancer agent encoded therein. Determination of expression levels of miR-21 may be carried out using for example, real-time RT-PCR.

References

1. Ohana, P., P. Schachter, B. Ayesh, A. Mizrahi, T. Birman, T. Schneider, I. Matouk, S. Ayesh, P. J. Kuppen, N. de Groot, A. Czerniak, and A. Hochberg, Regulatory sequences of H19 and IGF2 genes in DNA-based therapy of colorectal rat liver metastases. J Gene Med, 2005. 7(3): p. 366-374.

2. Varda-Bloom, N., I. Hodish, A. Shaish, S. Greenberger, R. Tal, B. Feder, J. Roitelman, E. Breitbart, L. Bangio, I. Barshack, R. Pfeffer, and D. Harats, Specific Induction of Tumor Neovasculature Death by Modified Murine PPE-1 Promoter Armed with HSV-TK. Pathobiology, 2008. 75(6): p. 346-355.

3. Giladi, N., H. Dvory-Sobol, E. Sagiv, D. Kazanov, E. Liberman, and N. Arber, Gene therapy approach in prostate cancer cells using an active Wnt signal. Biomedicine & Pharmacotherapy, 2007. 61(9): p. 527-530.

4. Barnes, D., M. Kunitomi, M. Vignuzzi, K. Saksela, and R. Andino, Harnessing Endogenous miRNAs to Control Virus Tissue Tropism as a Strategy for Developing Attenuated Virus Vaccines. Cell Host & Microbe, 2008. 4(3): p. 239-248.

5. Chan, J. A., A. M. Krichevsky, and K. S. Kosik, MicroRNA-21 is an antiapoptotic factor in human glioblastoma cells. Cancer Res, 2005. 65(14): p. 6029-6033.

6. Gabriely, G., T. Wurdinger, S. Kesari, C. C. Esau, J. Burchard, P. S. Linsley, and A. M. Krichevsky, MicroRNA 21 promotes glioma invasion by targeting matrix metalloproteinase regulators. Mol Cell Biol, 2008. 28(17): p. 5369-5380.

7. Iorio, M. V., M. Ferracin, C. G. Liu, A. Veronese, R. Spizzo, S. Sabbioni, E. Magri, M. Pedriali, M. Fabbri, M. Campiglio, S. Menard, J. P. Palazzo, A. Rosenberg, P. Musiani, S. Volinia, I. Nenci, G. A. Calin, P. Querzoli, M. Negrini, and C. M. Croce, MicroRNA gene expression deregulation in human breast cancer. Cancer Res, 2005. 65(16): p. 7065-7070.

8. Sempere, L. F., M. Christensen, A. Silahtaroglu, M. Bak, C. V. Heath, G. Schwartz, W. Wells, S. Kauppinen, and C. N. Cole, Altered MicroRNA expression confined to specific epithelial cell subpopulations in breast cancer. Cancer Res, 2007. 67(24): p. 11612-11620.

9. Si, M. L., S. Zhu, H. Wu, Z. Lu, F. Wu, and Y. Y. Mo, miR-21-mediated tumor growth. Oncogene, 2007. 26(19): p. 2799-2803.

10. Qian, B., D. Katsaros, L. Lu, M. Preti, A. Durando, R. Arisio, L. Mu, and H. Yu, High miR-21 expression in breast cancer associated with poor disease-free survival in early stage disease and high TGF-beta1. Breast Cancer Res Treat, 2008.

11. Yan, L. X., X. F. Huang, Q. Shao, M. Y. Huang, L. Deng, Q. L. Wu, Y. X. Zeng, and J. Y. Shao, MicroRNA miR-21 overexpression in human breast cancer is associated with advanced clinical stage, lymph node metastasis and patient poor prognosis. RNA, 2008. 14(11): p. 2348-2360.

12. Kutay, H., S. Bai, J. Datta, T. Motiwala, I. Pogribny, W. Frankel, S. T. Jacob, and K. Ghoshal, Downregulation of miR-122 in the rodent and human hepatocellular carcinomas. J Cell Biochem, 2006. 99(3): p. 671-678.

13. Connolly, E., M. Melegari, P. Landgraf, T. Tchaikovskaya, B. C. Tennant, B. L. Slagle, L. E. Rogler, M. Zavolan, T. Tuschl, and C. E. Rogler, Elevated expression of the miR-17-92 polycistron and miR-21 in hepadnavirus-associated hepatocellular carcinoma contributes to the malignant phenotype. Am J Pathol, 2008. 173(3): p. 856-864.

14. Jiang, J., Y. Gusev, I. Aderca, T. A. Mettler, D. M. Nagorney, D. J. Brackett, L. R. Roberts, and T. D. Schmittgen, Association of MicroRNA expression in hepatocellular carcinomas with hepatitis infection, cirrhosis, and patient survival. Clin Cancer Res, 2008. 14(2): p. 419-427.

15. Ladeiro, Y., G. Couchy, C. Balabaud, P. Bioulac-Sage, L. Pelletier, S. Rebouissou, and J. Zucman-Rossi, MicroRNA profiling in hepatocellular tumors is associated with clinical features and oncogene/tumor suppressor gene mutations. Hepatology, 2008. 47(6): p. 1955-1963.

16. Meng, F., R. Henson, M. Lang, H. Wehbe, S. Maheshwari, J. T. Mendell, J. Jiang, T. D. Schmittgen, and T. Patel, Involvement of human micro-RNA in growth and response to chemotherapy in human cholangiocarcinoma cell lines. Gastroenterology, 2006. 130(7): p. 2113-2129.

17. Roldo, C., E. Missiaglia, J. P. Hagan, M. Falconi, P. Capelli, S. Bersani, G. A. Calin, S. Volinia, C. G. Liu, A. Scarpa, and C. M. Croce, MicroRNA expression abnormalities in pancreatic endocrine and acinar tumors are associated with distinctive pathologic features and clinical behavior. J Clin Oncol, 2006. 24(29): p. 4677-4684.

18. Lee, E. J., Y. Gusev, J. Jiang, G. J. Nuovo, M. R. Lerner, W. L. Frankel, D. L. Morgan, R. G. Postier, D. J. Brackett, and T. D. Schmittgen, Expression profiling identifies microRNA signature in pancreatic cancer. Int J Cancer, 2007. 120(5): p. 1046-1054.

19. Dillhoff, M., J. Liu, W. Frankel, C. Croce, and M. Bloomston, MicroRNA-21 is Overexpressed in Pancreatic Cancer and a Potential Predictor of Survival. J Gastrointest Surg, 2008.

20. Volinia, S., G. A. Calin, C. G. Liu, S. Ambs, A. Cimmino, F. Petrocca, R. Visone, M. Iorio, C. Roldo, M. Ferracin, R. L. Prueitt, N. Yanaihara, G. Lanza, A. Scarpa, A. Vecchione, M. Negrini, C. C. Harris, and C. M. Croce, A microRNA expression signature of human solid tumors defines cancer gene targets. Proc Natl Acad Sci USA, 2006. 103(7): p. 2257-2261.

21. Fulci, V., S. Chiaretti, M. Goldoni, G. Azzalin, N. Carucci, S. Tavolaro, L. Castellano, A. Magrelli, F. Citarella, 22. Gao, J., T. T. Yang, X. C. Qiu, B. Yu, J. W. Han, Q. Y. Fan, and B. A. Ma, [Cloning and identification of microRNA from human osteosarcoma cell line SOSP-9607]. Ai Zheng, 2007. 26(6): p. 561-565.

21. M. Messina, R. Maggio, N. Peragine, S. Santangelo, F. R. Mauro, P. Landgraf, T. Tuschl, D. B. Weir, M. Chien, J. J. Russo, J. Ju, R. Sheridan, C. Sander, M. Zavolan, A. Guarini, R. Foa, and G. Macino, Quantitative technologies establish a novel microRNA profile of chronic lymphocytic leukemia. Blood, 2007. 109(11): p. 4944-4951.

23. Iorio, M. V., R. Visone, G. Di Leva, V. Donati, F. Petrocca, P. Casalini, C. Taccioli, S. Volinia, C. G. Liu, H. Alder, G. A. Calin, S. Menard, and C. M. Croce, MicroRNA signatures in human ovarian cancer. Cancer Res, 2007. 67(18): p. 8699-8707.

24. Lawrie, C. H., S. Soneji, T. Marafioti, C. D. Cooper, S. Palazzo, J. C. Paterson, H. Cattan, T. Enver, R. Mager, J. Boultwood, J. S. Wainscoat, and C. S. Hatton, MicroRNA expression distinguishes between germinal center B cell-like and activated B cell-like subtypes of diffuse large B cell lymphoma. Int J Cancer, 2007. 121(5): p. 1156-1161.

25. Lawrie, C. H., S. Gal, H. M. Dunlop, B. Pushkaran, A. P. Liggins, K. Pulford, A. H. Banham, F. Pezzella, J. Boultwood, J. S. Wainscoat, C. S. Hatton, and A. L. Harris, Detection of elevated levels of tumour-associated microRNAs in serum of patients with diffuse large B-cell lymphoma. Br J Haematol, 2008. 141(5): p. 672-675.

26. Lui, W. O., N. Pourmand, B. K. Patterson, and A. Fire, Patterns of known and novel small RNAs in human cervical cancer. Cancer Res, 2007. 67(13): p. 6031-6043.

27. Loffler, D., K. Brocke-Heidrich, G. Pfeifer, C. Stocsits, J. Hackermuller, A. K. Kretzschmar, R. Burger, M. Gramatzki, C. Blumert, K. Bauer, H. Cvijic, A. K. Ullmann, P. F. Stadler, and F. Horn, Interleukin-6 dependent survival of multiple myeloma cells involves the Stat3-mediated induction of microRNA-21 through a highly conserved enhancer. Blood, 2007. 110(4): p. 1330-1333.

28. Pichiorri, F., S. S. Suh, M. Ladetto, M. Kuehl, T. Palumbo, D. Drandi, C. Taccioli, N. Zanesi, H. Alder, J. P. Hagan, R. Munker, S. Volinia, M. Boccadoro, R. Garzon, A. Palumbo, R. I. Aqeilan, and C. M. Croce, MicroRNAs regulate critical genes associated with multiple myeloma pathogenesis. Proc Natl Acad Sci USA, 2008. 105(35): p. 12885-12890.

29. Slaby, O., M. Svoboda, P. Fabian, T. Smerdova, D. Knoflickova, M. Bednarikova, R. Nenutil, and R. Vyzula, Altered expression of miR-21, miR-31, miR-143 and miR-145 is related to clinicopathologic features of colorectal cancer. Oncology, 2007. 72(5-6): p. 397-402.

30. Chan, S. H., C. W. Wu, A. F. Li, C. W. Chi, and W. C. Lin, miR-21 microRNA expression in human gastric carcinomas and its clinical association. Anticancer Res, 2008. 28(2A): p. 907-911.

31. Schetter, A. J., S. Y. Leung, J. J. Sohn, K. A. Zanetti, E. D. Bowman, N. Yanaihara, S. T. Yuen, T. L. Chan, D. L. Kwong, G. K. Au, C. G. Liu, G. A. Calin, C. M. Croce, and C. C. Harris, MicroRNA expression profiles associated with prognosis and therapeutic outcome in colon adenocarcinoma. JAMA, 2008. 299(4): p. 425-436.

32. Zhang, Z., Z. Li, C. Gao, P. Chen, J. Chen, W. Liu, S. Xiao, and H. Lu, miR-21 plays a pivotal role in gastric cancer pathogenesis and progression. Lab Invest, 2008.

33. Tran, N., T. McLean, X. Zhang, C. J. Zhao, J. M. Thomson, C. O'Brien, and B. Rose, MicroRNA expression profiles in head and neck cancer cell lines. Biochem Biophys Res Commun, 2007. 358(1): p. 12-17.

34. Chang, S. S., W. W. Jiang, I. Smith, L. M. Poeta, S. Begum, C. Glazer, S. Shan, W. Westra, D. Sidransky, and J. A. Califano, MicroRNA alterations in head and neck squamous cell carcinoma. Int J Cancer, 2008. 123(12): p. 2791-2797.

35. Feber, A., L. Xi, J. D. Luketich, A. Pennathur, R. J. Landreneau, M. Wu, S. J. Swanson, T. E. Godfrey, and V. R. Litle, MicroRNA expression profiles of esophageal cancer. J Thorac Cardiovasc Surg, 2008. 135(2): p. 255-260; discussion 260.

36. Wang, T., X. Zhang, L. Obijuru, J. Laser, V. Aris, P. Lee, K. Mittal, P. Soteropoulos, and J. J. Wei, A micro-RNA signature associated with race, tumor size, and target gene activity in human uterine leiomyomas. Genes Chromosomes Cancer, 2007. 46(4): p. 336-347.

37. Amaral, F. C., N. Torres, F. Saggioro, L. Neder, H. R. Machado, W. A. Silva, Jr., A. C. Moreira, and M. Castro, MicroRNAs differentially expressed in ACTH-secreting pituitary tumors. J Clin Endocrinol Metab, 2008.

38. Markou, A., E. G. Tsaroucha, L. Kaklamanis, M. Fotinou, V. Georgoulias, and E. S. Lianidou, Prognostic value of mature microRNA-21 and microRNA-205 overexpression in non-small cell lung cancer by quantitative real-time RT-PCR. Clin Chem, 2008. 54(10): p. 1696-1704.

39. Nam, E. J., H. Yoon, S. W. Kim, H. Kim, Y. T. Kim, J. H. Kim, J. W. Kim, and S. Kim, MicroRNA expression profiles in serous ovarian carcinoma. Clin Cancer Res, 2008. 14(9): p. 2690-2695.

40. Neely, L. A., K. M. Rieger-Christ, B. S, Neto, A. Eroshkin, J. Garver, S. Patel, N. A. Phung, S. McLaughlin, J. A. Libertino, D. Whitney, and I. C. Summerhayes, A microRNA expression ratio defining the invasive phenotype in bladder tumors. Urol Oncol, 2008.

41. Betel, D., M. Wilson, A. Gabow, D. S. Marks, and C. Sander, The microRNA.org resource: targets and expression. Nucl. Acids Res., 2008. 36(suppl_1): p. D149-153.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A nucleic acid construct comprising an miR-21 promoter sequence and at least one nucleic acid sequence encoding a cytotoxic agent, wherein the nucleic acid sequence encoding the cytotoxic agent is operably linked to the miR-21 promoter sequence, wherein the miR-21 promoter sequence has at least 80% identity with SEQ ID NO: 1.

2. The construct of claim 1, wherein the miR-21 promoter sequence comprises SEQ ID NO: 1.

3. The construct of claim 1, wherein the cytotoxic agent is selected from the group consisting of a toxin, a fragment of a toxin, a drug-metabolizing enzyme, and an inducer of apoptosis.

4. The construct of claim 1, wherein said cytotoxic agent is a toxin selected from the group consisting of a bacterial toxin, a plant toxin, a fungal toxin and a combination thereof; a drug-metabolizing enzyme comprising a kinase; or an inducer of apoptosis selected from the group consisting of PUMA; BAX; BAK; Bci-XS; BAD; BIM; BIK; BID; HRK; Ad EIB; an ICE-CED3 protease; TRAIL; SARP-2; and apoptin.

5. The construct of claim 4, wherein said cytotoxic agent is a toxin consisting of a bacterial toxin selected from the group consisting of diphtheria toxin, *Pseudomonas* exotoxin, cholera toxin, anthrax toxin, botulinum toxin, pertussis toxin, *E. coli* enterotoxin, and shiga toxin; a plant toxin selected from the group consisting of ricin, modeccin, abrin, volkensin and viscumin; or a fungal toxin selected from the group consisting of a sarcin, restrictocin, mitogillin, enomycin, RNase T1 and phenomycin.

6. The construct of claim 5, wherein said toxin is a diphtheria toxin consisting of fragment A of diphtheria toxin (DT-A) and having the amino acid sequence of SEQ ID NO: 19.

7. The construct of claim 1, comprising SEQ ID NO: 1 as the miR-21 promoter sequence, and further comprising SEQ ID NO: 18 as the nucleic acid sequence encoding a cytotoxic agent.

8. The construct of claim 1, wherein the nucleic acid construct is substantially devoid of a nucleic acid sequence corresponding to or complementary to a form of miR-21 selected from the group consisting of: a primary transcript of miR-21 (pri-miR-21); a precursor of miR-21 (pre-miR-21); an RNA duplex of miR-21, and a mature miR-21.

9. The construct of claim 1, comprising a sequence selected from the group consisting of SEQ ID NO: 7 and SEQ ID NO: 8.

10. A vector comprising the nucleic acid construct of claim 1.

11. The vector of claim 10, selected from the group consisting of SEQ ID NO: 9 and SEQ ID NO: 10.

12. An isolated host cell comprising the vector of claim 10.

13. A pharmaceutical composition comprising as an active ingredient the construct of claim 1, and at least one pharmaceutically acceptable carrier, excipient or diluent.

14. A kit comprising;
  i) one or more dosage units of the vector of claim 10; and
  ii) instructions for administering said nucleic acid construct to a subject in need thereof.

\* \* \* \* \*

SEQUENCE LISTING

<160> NUMBER OF SEQ ID NOS: 30

<210> SEQ ID NO 1
<211> LENGTH: 507
<212> TYPE: DNA
<213> ORGANISM: Artificial Sequence

```
<220> FEATURE:
<223> OTHER INFORMATION: Synthetic

<400> SEQUENCE: 1
tgtattctgg gtaagaagga gctccgagta cataaattta tcaaagatca ctatcccaat      60
catctcagaa caagctgtta ctaatgtact ggagtttctg tgcaaactgt ctaccataaa     120
ccatgaaagg attcaaagtt catagttcct tctttgttcc tttgttaatc actgacttct     180
gactagtggg aggtgcctcc caagtttgct aatgcattct ttttggataa ggatgacgca     240
cagattgtcc taataaggac ttagattgag aaagaccgcc ccctctgaga gaggggaca      300
agtcagagag agggcgggca gtttcttttt taactaggat gacacaagca taagtcattt     360
ccttattaat tggttcaaac cagttcttac aggaactagt ggtgataatg tgggacttct     420
gagaagtcat tcattttatt ctttgtgcca taccagagta cagtatcagc tgagctgacc     480
ttactctgag gactaactct tttgctg                                         507

<210> SEQ ID NO 2
<211> LENGTH: 3404
<212> TYPE: DNA
<213> ORGANISM: Artificial Sequence
<220> FEATURE:
<223> OTHER INFORMATION: Synthetic

<400> SEQUENCE: 2
gtcttttctg taaacgattc tgaggcaaag ggaaatgact agaagaggat gagtaaacaa      60
taacctgaaa tgggaaactc gagggaagca caggtttttt ttgttttgtt ttgtttggtt     120
cgttttttgt tctttggggt ttttttgaga cagaatttcg ctctcgttgc ccaagttgga     180
gtgcaatggc gcgatcttgg ctcactgcaa cctccgcctc ccgggttcaa gcgattctcc     240
tgcctcagcc tcccaagtag ctgtgattcc aggcacgtgc caccacacca gctaattttt     300
tgtatttttaa tagaaacagg gtttcaccgt gttagccagg ctggtctcaa actgacctca     360
gatgatccgc ccgccttggc ctcccaaagt gctgggatta cagatgtgag ccaccgcgcc     420
cggccagagc actgtttttt ttaatggcct tgcactcttc ttatggacct tgctgccct      480
cagttgacca aacatgacat cagaaacaga tacatttgtg tgttttaaaa acagctccta     540
atactggaac aaaaatattt aactgtcttg acaatactca tgagtatctg catggcgact     600
tcagagttga gtttaatcaa agagtttatt cttaggtcct agtagaagag ctaacctcac     660
actcatccca ttctaaacta tgtgattcaa cactgatttt acatccaaca aagtgaaatc     720
ttgatagttg ggtgtaaaaa ggagagtaat ggagatttca gagtagttgg ggttgcttac     780
ttttcatttt taattcttta ggttttgtaa gttacacact tcaagcatta tagatgatcc     840
tcttttttact actgaactaa tgaagccttt ttcattgcat tgttctgcat ttatttctac     900
agggagaaaa ctggttgtcc tggatgtttg aaaagttggt cgttgtcatg gtgtgttact     960
tcatcctatc tatcattaac tccatggcac aaagttatgc caaacgaatc cagcagcggt    1020
tgaactcaga ggagaaaact aaataagtag agaaagtttt aaactgcaga aattggagtg    1080
gatgggttct gccttaaatt gggaggactc caagccggga aggaaaattc ccttttccaa    1140
cctgtatcaa ttttttacaac tttttttcctg aaagcagttt agtccatact ttgcactgac    1200
atactttttc cttctgtgct aaggtaaggt atccaccctc gatgcaatcc accttgtgtt    1260
ttcttagggt ggaatgtgat gttcagcagc aaacttgcaa cagactggcc ttctgtttgt    1320
tactttcaaa aggcccacat gatacaatta gagaattccc accgcacaaa aaagttcct     1380
```

```
aagtatgtta aatatgtcaa gcttttagg  cttgtcacaa atgattgctt tgttttccta   1440
agtcatcaaa atgtatataa attatctaga ttggataaca gtcttgcatg tttatcatgt   1500
tacaatttaa tattccatcc tgcccaaccc ttcctctccc atcctcaaaa aagggccatt   1560
ttatgatgca ttgcacaccc tctggggaaa ttgatcttta aattttgaga cagtataagg   1620
aaaatctggt tggtgtctta caagtgagct gacaccattt tttattctgt gtatttagaa   1680
tgaagtcttg aaaaaaactt tataaagaca tctttaatca ttccaaaatt gtgtccgttt   1740
tcttgagcgt tttgattttt tacttttagc ttataccagc tgaatggcag ccttgcctaa   1800
tccacctaca acaagaattt cttaagcttt cttttatttg catgagagag ccactaccaa   1860
ggcatgtttt gttatgctga aactgggctg ctgcatactg ctaaatggca cctctgggat   1920
tggcctacct ggggatttct tggtttgtga aacaggaga  ggagaaatat ctcatacaag   1980
tgaaaggata ctggagagag aaattaccca tttctaaaaa aaaaccacac tctgtcgtat   2040
ctgtgttaat gttttctagc atgtactctg gtttcaacag acacaaattt atatgttaac   2100
ccagttttct tgccgttctg taagtgtttt attcttagtg tgactttttt ccattgggat   2160
gttttgatt  gaacttgttc attttgtttt gcttgggagg aaaataaaca attttacttt   2220
tttcctttag gagcattatg agcattatgt cagaatagaa tagaattggg gttcgatctt   2280
aacaggccag aaatgcctgg gttttttttgg tttgttttg  tttttgtttt tttatcaaat   2340
cctgcctgac tgtctgcttg ttttgcctac catcgtgaca tctccatggc tgtaccacct   2400
tgtcgggtag cttatcagac tgatgttgac tgttgaatct catggcaaca ccagtcgatg   2460
ggctgtctga cattttggta tctttcatct gaccatccat atccaatgtt ctcatttaaa   2520
cattacccag catcattgtt tataatcaga aactctggtc cttctgtctg gtggcactta   2580
gagtcttttg tgccataatg cagcagtatg gagggaggat tttatggaga aatggggata   2640
gtcttcatga ccacaaataa ataaaggaaa actaagctgc attgtgggtt ttgaaaaggt   2700
tattatactt cttaacaatt ctttttttca gggactttc  tagctgtatg actgttactt   2760
gaccttcttt gaaaagcatt cccaaaatgc tctatttag  atagattaac attaaccaac   2820
ataatttttt ttagatcgag tcagcataaa tttctaagtc agcctctagt cgtggttcat   2880
ctctttcacc tgcattttat ttggtgtttg tctgaagaaa ggaagagga  aagcaaatac   2940
gaattgtact atttgtacca aatctttggg attcattggc aaataatttc agtgtggtgt   3000
attattaaat agaaaaaaaa aattttgttt cctaggttga aggtctaatt gatacgtttg   3060
acttatgatg accatttatg cactttcaaa tgaatttgct ttcaaaataa atgaagagca   3120
gctgtccttc tttcctcttt taagtgttca gctgtggcat gctcagaggt tcctgctgga   3180
ttccagctgg agcggtgtga tacccttctt ttttcagctgt tcgtgccttc ctttcttgta   3240
tccaccaaag tggagacaaa tacatgatct caaagataca cagtacctac ttaattccag   3300
ctgatgggag accaagaat  ttgcaagtgg atggtttggt atcactgtaa ataaaaagag   3360
ggcctgggaa ttcttgcgat tccatctcta aaaaaaaaa  aaaa                    3404
```

<210> SEQ ID NO 3
<211> LENGTH: 3463
<212> TYPE: DNA
<213> ORGANISM: Artificial Sequence
<220> FEATURE:
<223> OTHER INFORMATION: Synthetic

<400> SEQUENCE: 3

```
ataaaccaag gctcttacca tagctgaact ttaaaactta gactgtcttt tctgtaaacg     60
```

-continued

```
attctgaggc aaagggaaat gactagaaga ggatgagtaa acaataacct gaaatgggaa      120
actcgaggga agcacaggtt ttttttgttt tgttttgttt ggttcgtttt ttgttctttg      180
gggtttcttt gagacagaat ttcgctctcg ttgcccaagt tggagtgcaa tggcgcgatc      240
ttggctcact gcaacctccg cctcccgggt tcaagcgatt ctcctgcctc agcctcccaa      300
gtagctgtga ttccaggcac gtgccaccac accagctaat ttttgtatt ttaatagaaa       360 cagggtttca ccgtgttagc caggctggtc tcaaactgac ctcagatgat ccgcccgcct      420
tggcctccca aagtgctggg attacagatg tgagccaccg cgcccggcca gagcactgtt      480 tttttttaatg gccttgcact cttcttatgg acctttgctg ccctcagttg accaaacatg     540
acatcagaaa cagatacatt tgtgtgtttt aaaaacagct cctaatactg gaacaaaaat      600
atttaactgt cttgacaata ctcatgagta tctgcatggc gacttcagag ttgagtttaa      660
tcaaagagtt tattcttagg tcctagtaga agagctaacc tcacactcat cccattctaa     720
actatgtgat tcaacactga ttttacatcc cacaaagtga aatcttgata gttgggtgta     780
aaaaggagag taatggagat tcagagtag ttggggttgc ttacttttca ttttaattc        840 tttaggttt gtaagttaca cacttcaagc attatagatg atcctctttt tactactgaa       900
ctaatgaagc cttttcatt gcattgttct gcatttattt ctacagggag aaaactggtt       960
gtcctggatg tttgaaaagt tggtcgttgt catggtgtgt tacttcatcc tatctatcat     1020
taactccatg gcacaaagtt atgccaaacg aatccagcag cggttgaact cagaggagaa    1080
aactaaataa gtagagaaag ttttaaactg cagaaattgg agtggatggg ttctgcctta    1140
aattgggagg actccaagcc gggaaggaaa attccctttt ccaacctgta tcaattttta    1200 caacttttt cctgaaagca gtttagtcca tactttgcac tgacatactt tttccttctg      1260
tgctaaggta aggtatccac cctcgatgca atccaccttg tgttttctta gggtggaatg    1320
tgatgttcag cagcaaactt gcaacagact ggccttctgt ttgttacttt caaaaggccc    1380
acatgataca attagagaat tcccaccgca caaaaaaagt tcctaagtat gttaaatatg    1440
tcaagctttt taggcttgtc acaaatgatt gctttgtttt cctaagtcat caaaatgtat    1500
ataaattatc tagattggat aacagtcttg catgtttatc atgttacaat ttaatattcc    1560
atcctgccca accttcctc tcccatcctc aaaaagggc catttatga tgcattgcac       1620 accctctggg gaaattgatc tttaaatttt gagacagtat aaggaaaatc tggttggtgt    1680
cttacaagtg agctgacacc attttttatt ctgtgtattt agaatgaagt cttgaaaaaa    1740
actttataaa gacatcttta atcattccaa aattgtgtcc gttttcttga gcgttttgat    1800 tttttactttt tagcttatac cagctgaatg gcagccttgc ctaatccacc tacaacaaga    1860
atttcttaag ctttctttta tttgcatgag agagccacta ccaaggcatg ttttgttatg    1920
ctgaaactgg gctgctgcat actgctaaat ggcacctctg ggattggcct acctggggat    1980
ttcttggttt gtgaaaacag gagagggaa atatctcata caagtgaaag gatactggag    2040
agagaaatta cccatttcta aaaaaaaacc acactctgtc gtatctgtgt taatgttttc    2100
tagcatgtac tctggtttca acagacacaa atttatatgt taacccagtt ttcttgccgt    2160
tctgtaagtg ttttattctt agtgtgattt ttttccattg ggatgttttt gattgaactt    2220
gttcattttg ttttgcttgg gaggaaaata aacaattta ctttttttcct ttaggagcat     2280 tatgagcatt atgtcagaat agaatagaat tggggttcga tcttaacagg ccagaaatgc    2340
ctgggttttt tttggtttgt ttttgttttt gttttttat caaatcctgc ctgactgtct     2400
```

```
gcttgttttg cctaccatcg tgacatctcc atggctgtac caccttgtcg ggtagcttat    2460
cagactgatg ttgactgttg aatctcatgg caacaccagt cgatgggctg tctgacattt    2520
tggtatcttt catctgacca tccatatcca atgttctcat ttaaacatta cccagcatca    2580
ttgtttataa tcagaaactc tggtccttct gtctggtggc acttagagtc ttttgtgcca    2640
taatgcagca gtatggaggg aggattttat ggagaaatgg ggatagtctt catgaccaca    2700
aataaataaa ggaaaactaa gctgcattgt gggttttgaa aaggttatta tacttcttaa    2760
caattctttt tttcagggac ttttctagct gtatgactgt tacttgacct tcttgaaaa     2820 gcattcccaa aatgctctat tttagataga ttaacattaa ccaacataat ttttttaga    2880 tcgagtcagc ataaatttct aagtcagcct ctagtcgtgg ttcatctctt tcacctgcat    2940
tttatttggt gtttgtctga agaaaggaaa gaggaaagca aatacgaatt gtactatttg    3000
taccaaatct ttgggattca ttggcaaata atttcagtgt ggtgtattat taaatagaaa    3060
aaaaaatttt gtttcctagg ttgaaggtct aattgatacg tttgacttat gatgaccatt    3120
tatgcacttt caaatgaatt tgctttcaaa ataaatgaag agcagctgtc cttctttcct    3180
cttttaagtg ttcagctgtg gcatgctcag aggttcctgc tggattccag ctggagcggt    3240
gtgataccct tcttttcag ctgttcgtgc cttcctttct tgtgtccacc aaagtggaga    3300
caaatacatg atctcaaaga tacacagtac ctacttaatt ccagctgatg ggagaccaaa    3360
gaatttgcaa gtggatggtt tggtatcact gtaaataaaa agagggcctg ggaattcttg    3420
cgattccatc tctaaaaaaa aaaaaaaaaa aaaaaaaaaa aaa                       3463

<210> SEQ ID NO 4
<211> LENGTH: 72
<212> TYPE: DNA
<213> ORGANISM: Artificial Sequence
<220> FEATURE:
<223> OTHER INFORMATION: Synthetic

<400> SEQUENCE: 4
tgtcgggtag cttatcagac tgatgttgac tgttgaatct catggcaaca ccagtcgatg    60
ggctgtctga ca                                                        72

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
tagcttatca gactgatgtt ga                                              22

<210> SEQ ID NO 6
<211> LENGTH: 68
<212> TYPE: DNA
<213> ORGANISM: Artificial Sequence
<220> FEATURE:
<223> OTHER INFORMATION: Synthetic

<400> SEQUENCE: 6
tagtggtgat aaatgtggga cttctgagaa gtcattcatt ttattctttg tgccatacca    60
gagtacag                                                             68

<210> SEQ ID NO 7
<211> LENGTH: 1052
```

<212> TYPE: DNA
<213> ORGANISM: Artificial Sequence
<220> FEATURE:
<223> OTHER INFORMATION: Synthetic

<400> SEQUENCE: 7

```
accgaaggag ctccgagtac ataaatttat caaagatcac tatcccaatc atctcagaac      60
aagctgttac taatgtactg gagtttctgt gcaaactgtc taccataaac catgaaagga     120
ttcaaagttc atagttcctt ctttgttcct ttgttaatca ctgacttctg actagtggga     180
ggtgcctccc aagtttgcta atgcattctt tttggataag gatgacgcac agattgtcct     240
aataaggact tagattgaga aagaccgccc cctctgagaa gagggacaa gtcagagaga      300
gggcgggcag tttcttttttt aactagggat gacacaagca taagtcattt ccttattaat    360
tggttcaaac cagttcttac aggaactagt ggtgataaat gtgggacttc tgagaagtca     420
ttcattttat tctttgtgcc ataccagagt agaagcttgg cattccggta ctgttggtaa     480
agccaccatg ggcgctgatg atgttgttga ttcttctaaa tcttttgtga tggaaaactt     540
ttcttcgtac cacgggacta aacctggtta tgtagattcc attcaaaaag gtatacaaaa     600
gccaaaatct ggtacacaag gaaattatga cgatgattgg aaagggtttt atagtaccga     660
caataaatac gacgctgcgg gatactctgt agataatgaa aacccgctct ctggaaaagc     720
tggaggcgtg gtcaaagtga cgtatccagg actgacgaag gttctcgcac taaaagtgga     780
taatgccgaa actattaaga aagagttagg tttaagtctc actgaaccgt tgatggagca     840
agtcggaacg gaaagagttta tcaaaaggtt cggtgatggt gcttcgcgtg tagtgctcag    900
ccttcccttc gctgagggga gttctagcgt tgaatatatt aataactggg aacaggcgaa     960
agcgttaagc gtagaacttg agattaattt tgaaacccgt ggaaaacgtg gccaagatgc    1020
gatgtatgag tatatggctc aagccttcta ga                                 1052
```

<210> SEQ ID NO 8
<211> LENGTH: 1046
<212> TYPE: DNA
<213> ORGANISM: Artificial Sequence
<220> FEATURE:
<223> OTHER INFORMATION: Synthetic

<400> SEQUENCE: 8

```
accgaaggag ctccgagtac ataaatttat caaagatcac tatcccaatc atctcagaac      60
aagctgttac taatgtactg gagtttctgt gcaaactgtc taccataaac catgaaagga     120
ttcaaagttc atagttcctt ctttgttcct ttgttaatca ctgacttctg actagtggga     180
ggtgcctccc aagtttgcta atgcattctt tttggataag gatgacgcac agattgtcct     240
aataaggact tagattgaga aagaccgccc cctctgagaa gagggacaa gtcagagaga      300
gggcgggcag tttcttttttt aactagggat gacacaagca taagtcattt ccttattaat    360
tggttcaaac cagttcttac aggaactagt ggtgataaat gtgggacttc tgagaagtca     420
ttcattttat tctttgtgcc ataccagagt agaagcttat ggcccgcgca cgccaggagg     480
gcagctcccc ggagcccgta gagggcctgg cccgcgacgg cccgcgcccc ttccgctcg      540
gccgcctggt gccctcggca gtgtcctgcg gcctctgcga gccggcctg gctgccgccc      600
ccgccgcccc caccctgctg cccgctgcct acctctgcgc cccaccgcc ccacccgccg      660
tcaccgccgc cctgggggt tcccgctggc ctggggtcc ccgcagccgg ccccgaggcc      720
cgcgcccgga cggtcctcag ccctcgctct cgctggcgga gcagcacctg gagtcgcccg    780
```

| | |
|---|---|
| tgcccagcgc cccgggggct ctggcgggcg gtcccaccca ggcggccccg ggagtccgcg | 840 |
| gggaggagga acagtgggcc cgggagatcg gggcccagct gcggcggatg gcggacgacc | 900 |
| tcaacgcaca gtacgagcgg cggagacaag aggagcagca gcggcaccgc ccctcaccct | 960 |
| ggagggtcct gtacaatctc atcatgggac tcctgccctt acccagggc cacagagccc | 1020 |
| ccgagatgga gcccaattag tctaga | 1046 |

<210> SEQ ID NO 9
<211> LENGTH: 4126
<212> TYPE: DNA
<213> ORGANISM: Artificial Sequence
<220> FEATURE:
<223> OTHER INFORMATION: Synthetic

<400> SEQUENCE: 9

| | |
|---|---|
| ggtaccgaag gagctccgag tacataaatt tatcaaagat cactatccca atcatctcag | 60 |
| aacaagctgt tactaatgta ctggagtttc tgtgcaaact gtctaccata aaccatgaaa | 120 |
| ggattcaaag ttcatagttc cttctttgtt cctttgttaa tcactgactt ctgactagtg | 180 |
| ggaggtgcct cccaagtttg ctaatgcatt cttttggat aaggatgacg cacagattgt | 240 |
| cctaataagg acttagattg agaaagaccg ccccctctga aagagggga caagtcagag | 300 |
| agagggcggg cagtttcttt tttaactagg gatgacacaa gcataagtca tttccttatt | 360 |
| aattggttca aaccagttct tacaggaact agtggtgata aatgtgggac ttctgagaag | 420 |
| tcattcattt tattctttgt gccataccag agtagaagct tggcattccg gtactgttgg | 480 |
| taaagccacc atgggcgctg atgatgttgt tgattcttct aaatcttttg tgatggaaaa | 540 |
| cttttcttcg taccacggga ctaaacctgg ttatgtagat tccattcaaa aggtataca | 600 |
| aaagccaaaa tctggtacac aaggaaatta tgacgtatgat tggaaagggt tttatagtac | 660 |
| cgacaataaa tacgacgctg cggatactc tgtagataat gaaaaccgc tctctggaaa | 720 |
| agctggaggc gtggtcaaag tgacgtatcc aggactgacg aaggttctcg cactaaaagt | 780 |
| ggataatgcc gaaactatta gaaagagtt aggtttaagt ctcactgaac cgttgatgga | 840 |
| gcaagtcgga acggaagagt ttatcaaaag gttcggtgat ggtgcttcgc gtgtagtgct | 900 |
| cagccttccc ttcgctgagg ggagttctag cgttgaatat attaataact gggaacaggc | 960 |
| gaaagcgtta agcgtagaac ttgagattaa ttttgaaacc cgtggaaaac gtggccaaga | 1020 |
| tgcgatgtat gagtatatgg ctcaagcctt ctagagtcgg gcggccggc cgcttcgagc | 1080 |
| agacatgata agatacattg atgagtttgg acaaaccaca actagaatgc agtgaaaaaa | 1140 |
| atgctttatt tgtgaaattt gtgatgctat tgctttattt gtaaccatta taagctgcaa | 1200 |
| taaacaagtt aacaacaaca attgcattca ttttatgttt caggttcagg ggaggtgtg | 1260 |
| ggaggttttt taaagcaagt aaaacctcta caaatgtggt aaaatcgata aggatccgtc | 1320 |
| gaccgatgcc cttgagagcc ttcaacccag tcagctcctt ccggtgggcg cggggcatga | 1380 |
| ctatcgtcgc cgcacttatg actgtcttct ttatcatgca actcgtagga caggtgccgg | 1440 |
| cagcgctctt ccgcttcctc gctcactgac tcgctgcgct cggtcgttcg gctgcggcga | 1500 |
| gcggtatcag ctcactcaaa ggcggtaata cggttatcca cagaatcagg ggataacgca | 1560 |
| ggaaagaaca tgtgagcaaa aggccagcaa aaggccagga accgtaaaaa ggccgcgttg | 1620 |
| ctggcgtttt tccataggct ccgcccccct gacgagcatc acaaaaatcg acgctcaagt | 1680 |
| cagaggtggc gaaacccgac aggactataa agataccagg cgtttccccc tggaagctcc | 1740 |
| ctcgtgcgct ctcctgttcc gaccctgccg cttaccggat acctgtccgc ctttctccct | 1800 |

```
tcgggaagcg tggcgctttc tcaatgctca cgctgtaggt atctcagttc ggtgtaggtc    1860
gttcgctcca agctgggctg tgtgcacgaa ccccccgttc agcccgaccg ctgcgcctta    1920
tccggtaact atcgtcttga gtccaacccg gtaagacacg acttatcgcc actggcagca    1980
gccactggta acaggattag cagagcgagg tatgtaggcg gtgctacaga gttcttgaag    2040
tggtggccta actacggcta cactagaagg acagtatttg gtatctgcgc tctgctgaag    2100
ccagttacct tcggaaaaag agttggtagc tcttgatccg gcaaacaaac caccgctggt    2160
agcggtggtt ttttttgttg caagcagcag attacgcgca gaaaaaaagg atctcaagaa    2220
gatcctttga tcttttctac ggggtctgac gctcagtgga acgaaaactc acgttaaggg    2280
attttggtca tgagattatc aaaaaggatc ttcacctaga tccttttaaa ttaaaaatga    2340
agttttaaat caatctaaag tatatatgag taaacttggt ctgacagtta ccaatgctta    2400
atcagtgagg cacctatctc agcgatctgt ctatttcgtt catccatagt tgcctgactc    2460
cccgtcgtgt agataactac gatacgggag ggcttaccat ctggccccag tgctgcaatg    2520
ataccgcgag acccacgctc accggctcca gatttatcag caataaacca gccagccgga    2580
agggccgagc gcagaagtgg tcctgcaact ttatccgcct ccatccagtc tattaattgt    2640
tgccgggaag ctagagtaag tagttcgcca gttaatagtt tgcgcaacgt tgttgccatt    2700
gctacaggca tcgtggtgtc acgctcgtcg tttggtatgg cttcattcag ctccggttcc    2760
caacgatcaa ggcgagttac atgatccccc atgttgtgca aaaaagcggt tagctccttc    2820
ggtcctccga tcgttgtcag aagtaagttg gccgcagtgt tatcactcat ggttatggca    2880
gcactgcata attctcttac tgtcatgcca tccgtaagat gcttttctgt gactggtgag    2940
tactcaacca agtcattctg agaatagtgt atgcggcgac cgagttgctc ttgcccggcg    3000
tcaatacggg ataataccgc gccacatagc agaactttaa aagtgctcat cattggaaaa    3060
cgttcttcgg ggcgaaaact ctcaaggatc ttaccgctgt tgagatccag ttcgatgtaa    3120
cccactcgtg cacccaactg atcttcagca tcttttactt tcaccagcgt ttctgggtga    3180
gcaaaaacag gaaggcaaaa tgccgcaaaa aagggaataa gggcgacacg gaaatgttga    3240
atactcatac tcttcctttt tcaatattat tgaagcattt atcagggtta ttgtctcatg    3300
agcggataca tatttgaatg tatttagaaa aataaacaaa taggggttcc gcgcacattt    3360
ccccgaaaag tgccacctga cgcgccctgt agcggcgcat taagcgcggc gggtgtggtg    3420
gttacgcgca gcgtgaccgc tacacttgcc agcgccctag cgcccgctcc tttcgctttc    3480
ttcccttcct ttctcgccac gttcgccggc tttccccgtc aagctctaaa tcggggctc    3540
cctttagggt tccgatttag tgctttacgg cacctcgacc ccaaaaaact tgattagggt    3600
gatggttcac gtagtgggcc atcgccctga tagacggttt ttcgcccttt gacgttggag    3660
tccacgttct ttaatagtgg actcttgttc caaactggaa caacactcaa ccctatctcg    3720
gtctattctt ttgatttata agggattttg ccgatttcgg cctattggtt aaaaaatgag    3780
ctgatttaac aaaaatttaa cgcgaatttt aacaaaatat taacgtttac aatttcccat    3840
tcgccattca ggctgcgcaa ctgttgggaa gggcgatcgg tgcgggcctc ttcgctatta    3900
cgccagccca agctaccatg ataagtaagt aatattaagg tacgggaggt acttggagcg    3960
gccgcaataa aatatcttta ttttcattac atctgtgtgt tggttttttg tgtgaatcga    4020
tagtactaac atacgctctc catcaaaaca aaacgaaaca aaacaaacta gcaaaatagg    4080
ctgtccccag tgcaagtgca ggtgccagaa catttctcta tcgata                   4126
```

<210> SEQ ID NO 10
<211> LENGTH: 4120
<212> TYPE: DNA
<213> ORGANISM: Artificial Sequence
<220> FEATURE:
<223> OTHER INFORMATION: Synthetic

<400> SEQUENCE: 10

```
ggtaccgaag gagctccgag tacataaatt tatcaaagat cactatccca atcatctcag      60
aacaagctgt tactaatgta ctggagtttc tgtgcaaact gtctaccata aaccatgaaa     120
ggattcaaag ttcatagttc cttctttgtt cctttgttaa tcactgactt ctgactagtg     180
ggaggtgcct cccaagtttg ctaatgcatt cttttttggat aaggatgacg cacagattgt     240
cctaataagg acttagattg agaaagaccg ccccctctga agagggga caagtcagag         300
agagggcggg cagtttcttt tttaactagg gatgacacaa gcataagtca tttccttat       360
aattggttca aaccagttct tacaggaact agtggtgata atgtgggac ttctgagaag         420
tcattcattt tattctttgt gccataccag agtagaagct tatggcccgc gcacgccagg      480
agggcagctc cccggagccc gtagagggcc tggcccgcga cggcccgcgc ccttcccgc        540
tcggccgcct ggtgccctcg gcagtgtcct gcggcctctg cgagcccggc ctggctgccg      600
ccccgccgc ccccacctg ctgcccgctg cctacctctg cgccccacc gccccacccg          660
ccgtcaccgc cgccctgggg ggttcccgct ggcctggggg tccccgcagc cggccccgag      720
gccccgcgccc ggacggtcct cagccctcgc tctcgctggc ggagcagcac ctggagtcgc     780
ccgtgcccag cgccccgggg gctctggcgg gcggtcccac ccaggcggcc ccgggagtcc      840
gcggggagga ggaacagtgg gcccgggaga tcggggccca gctgcggcgg atggcggacg      900
acctcaacgc acagtacgag cggcggagac aagaggagca gcagcggcac cgcccctcac      960
cctggagggt cctgtacaat ctcatcatgg gactcctgcc cttacccagg ggccacagag    1020
cccccgagat ggagcccaat tagtctctag tcggggcggc cggccgcttc gagcagacat    1080
gataagatac attgatgagt ttggacaaac cacaactaga atgcagtgaa aaaaatgctt    1140
tatttgtgaa atttgtgatg ctattgcttt atttgtaacc attataagct gcaataaaca    1200
agttaacaac aacaattgca ttcattttat gtttcaggtt cagggggagg tgtgggaggt    1260
tttttaaagc aagtaaaacc tctacaaatg tggtaaaatc gataaggatc cgtcgaccga    1320
tgcccttgag agccttcaac ccagtcagct ccttccggtg ggcgcggggc atgactatcg    1380
tcgccgcact tatgactgtc ttctttatca tgcaactcgt aggacaggtg ccggcagcgc    1440
tcttccgctt cctcgctcac tgactcgctg cgctcggtcg ttcggctgcg gcgagcggta    1500
tcagctcact caaaggcggt aatacggtta tccacagaat caggggataa cgcaggaaag    1560
aacatgtgag caaaaggcca gcaaaggcc aggaaccgta aaaaggccgc gttgctggcg    1620
ttttccata ggctccgccc ccctgacgag catcacaaaa atcgacgctc aagtcagagg    1680
tggcgaaacc cgacaggact ataaagatac caggcgtttc ccctggaag ctccctcgtg    1740
cgctctcctg ttccgaccct gccgcttacc ggatacctgt ccgcctttct cccttcggga    1800
agcgtggcgc tttctcaatg ctcacgcgt aggtatctca gttcggtgta ggtcgttcgc    1860
tccaagctgg gctgtgtgca cgaaccccc gttcagcccg accgctgcgc cttatccggt    1920
aactatcgtc ttgagtccaa cccggtaaga cacgacttat cgccactggc agcagccact    1980
ggtaacagga ttagcagagc gaggtatgta ggcggtgcta cagagttctt gaagtggtgg    2040
cctaactacg gctacactag aaggacagta tttggtatct gcgctctgct gaagccagtt    2100
```

```
accttcggaa aaagagttgg tagctcttga tccggcaaac aaaccaccgc tggtagcggt    2160
ggttttttg  tttgcaagca gcagattacg cgcagaaaaa aaggatctca agaagatcct    2220
ttgatctttt ctacggggtc tgacgctcag tggaacgaaa actcacgtta agggattttg    2280
gtcatgagat tatcaaaaag gatcttcacc tagatccttt taaattaaaa atgaagtttt    2340
aaatcaatct aaagtatata tgagtaaact tggtctgaca gttaccaatg cttaatcagt    2400
gaggcaccta tctcagcgat ctgtctattt cgttcatcca tagttgcctg actccccgtc    2460
gtgtagataa ctacgatacg ggagggctta ccatctggcc ccagtgctgc aatgataccg    2520
cgagacccac gctcaccggc tccagattta tcagcaataa accagccagc cggaagggcc    2580
gagcgcagaa gtggtcctgc aactttatcc gcctccatcc agtctattaa ttgttgccgg    2640
gaagctagag taagtagttc gccagttaat agtttgcgca acgttgttgc cattgctaca    2700
ggcatcgtgg tgtcacgctc gtcgtttggt atggcttcat tcagctccgg ttcccaacga    2760
tcaaggcgag ttacatgatc ccccatgttg tgcaaaaaag cggttagctc cttcggtcct    2820
ccgatcgttg tcagaagtaa gttggccgca gtgttatcac tcatggttat ggcagcactg    2880
cataattctc ttactgtcat gccatccgta agatgctttt ctgtgactgg tgagtactca    2940
accaagtcat tctgagaata gtgtatgcgg cgaccgagtt gctcttgccc ggcgtcaata    3000
cgggataata ccgcgccaca tagcagaact ttaaaagtgc tcatcattgg aaaacgttct    3060
tcggggcgaa aactctcaag gatcttaccg ctgttgagat ccagttcgat gtaacccact    3120
cgtgcaccca actgatcttc agcatctttt actttcacca gcgtttctgg gtgagcaaaa    3180
acaggaaggc aaaatgccgc aaaaaaggga ataagggcga cacggaaatg ttgaatactc    3240
atactcttcc ttttcaata ttattgaagc atttatcagg gttattgtct catgagcgga    3300
tacatatttg aatgtattta gaaaaataaa caaatagggg ttccgcgcac atttccccga    3360
aaagtgccac ctgacgcgcc ctgtagcggc gcattaagcg cggcgggtgt ggtggttacg    3420
cgcagcgtga ccgctacact tgccagcgcc ctagcgcccg ctcctttcgc tttcttccct    3480
tcctttctcg ccacgttcgc cggctttccc cgtcaagctc taaatcgggg gctcccttta    3540
gggttccgat ttagtgcttt acggcacctc gaccccaaaa aacttgatta gggtgatggt    3600
tcacgtagtg ggccatcgcc ctgatagacg gttttcgcc  ctttgacgtt ggagtccacg    3660
ttctttaata gtggactctt gttccaaact ggaacaacac tcaacccat  ctcggtctat    3720
tcttttgatt tataagggat tttgccgatt tcggcctatt ggttaaaaaa tgagctgatt    3780
taacaaaaat ttaacgcgaa ttttaacaaa atattaacgt ttacaatttc ccattcgcca    3840
ttcaggctgc gcaactgttg ggaagggcga tcggtgcggg cctcttcgct attacgccag    3900
cccaagctac catgataagt aagtaatatt aaggtacggg aggtacttgg agcggccgca    3960
ataaaatatc tttattttca ttacatctgt gtgttggttt tttgtgtgaa tcgatagtac    4020
taacatacgc tctccatcaa aacaaaacga aacaaaacaa actagcaaaa taggctgtcc    4080
ccagtgcaag tgcaggtgcc agaacatttc tctatcgata                        4120
```

<210> SEQ ID NO 11
<211> LENGTH: 2140
<212> TYPE: DNA
<213> ORGANISM: Artificial Sequence
<220> FEATURE:
<223> OTHER INFORMATION: Synthetic

<400> SEQUENCE: 11

| | |
|---|---|
| accgaaggag ctccgagtac ataaatttat caaagatcac tatcccaatc atctcagaac | 60 |
| aagctgttac taatgtactg gagtttctgt gcaaactgtc taccataaac catgaaagga | 120 |
| ttcaaagttc atagttcctt ctttgttcct tgttaatca ctgacttctg actagtggga | 180 |
| ggtgcctccc aagtttgcta atgcattctt tttggataag gatgacgcac agattgtcct | 240 |
| aataaggact tagattgaga aagaccgccc cctctgagaa gagggacaa gtcagagaga | 300 |
| gggcgggcag tttcttttt aactagggat gacacaagca taagtcattt ccttattaat | 360 |
| tggttcaaac cagttcttac aggaactagt ggtgataaat gtgggacttc tgagaagtca | 420 |
| ttcatttat tctttgtgcc ataccagagt agaagcttgg cattccggta ctgttggtaa | 480 |
| agccaccatg gaagacgcca aaaacataaa gaaaggcccg gcgccattct atccgctgga | 540 |
| agatggaacc gctggagagc aactgcataa ggctatgaag agatacgccc tggttcctgg | 600 |
| aacaattgct tttacagatg cacatatcga ggtggacatc acttacgctg agtacttcga | 660 |
| aatgtccgtt cggttggcag aagctatgaa acgatatggg ctgaatacaa atcacagaat | 720 |
| cgtcgtatgc agtgaaaact ctcttcaatt ctttatgccg gtgttgggcg cgttatttat | 780 |
| cggagttgca gttgcgcccg cgaacgacat ttataatgaa cgtgaattgc tcaacagtat | 840 |
| gggcatttcg cagcctaccg tggtgttcgt ttccaaaaag gggttgcaaa aaattttgaa | 900 |
| cgtgcaaaaa aagctcccaa tcatccaaaa aattattatc atggattcta aaacggatta | 960 |
| ccagggattt cagtcgatgt acacgttcgt cacatctcat ctacctcccg gttttaatga | 1020 |
| atacgatttt gtgccagagt ccttcgatag ggacaagaca attgcactga tcatgaactc | 1080 |
| ctctggatct actggtctgc ctaaaggtgt cgctctgcct catagaactg cctgcgtgag | 1140 |
| attctcgcat gccagagatc ctatttttgg caatcaaatc attccggata ctgcgatttt | 1200 |
| aagtgttgtt ccattccatc acggttttgg aatgtttact acactcggat atttgatatg | 1260 |
| tggatttcga gtcgtcttaa tgtatagatt tgaagaagag ctgtttctga ggagccttca | 1320 |
| ggattacaag attcaaagtg cgctgctggt gccaacccta ttctccttct cgccaaaag | 1380 |
| cactctgatt gacaaatacg atttatctaa tttacacgaa attgcttctg gtggcgctcc | 1440 |
| cctctctaag gaagtcgggg aagcggttgc caagaggttc catctgccag gtatcaggca | 1500 |
| aggatatggg ctcactgaga ctacatcagc tattctgatt acacccgagg gggatgataa | 1560 |
| accgggcgcg gtcggtaaag ttgttccatt ttttgaagcg aaggttgtgg atctggatac | 1620 |
| cgggaaaacg ctgggcgtta atcaaagagg cgaactgtgt gtgagaggtc ctatgattat | 1680 |
| gtccggttat gtaaacaatc cggaagcgac caacgccttg attgacaagg atggatggct | 1740 |
| acattctgga gacatagctt actgggacga agacgaacac ttcttcatcg ttgaccgcct | 1800 |
| gaagtctctg attaagtaca aaggctatca ggtggctccc gctgaattgg aatccatctt | 1860 |
| gctccaacac cccaacatct tcgacgcagg tgtcgcaggt cttcccgacg atgacgccgg | 1920 |
| tgaacttccc gccgccgttg ttgttttgga gcacggaaag acgatgacgg aaaaagagat | 1980 |
| cgtggattac gtcgccagtc aagtaacaac cgcgaaaaag ttgcgcggag gagttgtgtt | 2040 |
| tgtggacgaa gtaccgaaag gtcttaccgg aaaactcgac gcaagaaaaa tcagagagat | 2100 |
| cctcataaag gccaagaagg gcggaaagat cgccgtgtaa | 2140 |

<210> SEQ ID NO 12
<211> LENGTH: 637
<212> TYPE: DNA
<213> ORGANISM: Artificial Sequence
<220> FEATURE:
<223> OTHER INFORMATION: Synthetic

<400> SEQUENCE: 12

```
ctagtggtga taaatgtggg acttctgaga agtcattcat tttattcttt gtgccatacc    60
agagtacaag cttatgggcg ctgatgatgt tgttgattct tctaaatctt ttgtgatgga   120
aaacttttct tcgtaccacg ggactaaacc tggttatgta gattccattc aaaaaggtat   180
acaaaagcca aaatctggta cacaaggaaa ttatgacgat gattggaaag gttttatag    240
taccgacaat aaatacgacg ctgcgggata ctctgtagat aatgaaaacc cgctctctgg   300
aaaagctgga ggcgtggtca agtgacgta tccaggactg acgaaggttc tcgcactaaa    360
agtggataat gccgaaacta ttaagaaaga gttaggttta agtctcactg aaccgttgat   420
ggagcaagtc ggaacggaag agtttatcaa aaggttcggt gatggtgctt cgcgtgtagt   480
gctcagcctt cccttcgctg aggggagttc tagcgttgaa tatattaata actgggaaca   540
ggcgaaagcg ttaagcgtag aacttgagat taattttgaa acccgtggaa aacgtggcca   600
agatgcgatg tatgagtata tggctcaagc ctctaga                            637
```

<210> SEQ ID NO 13
<211> LENGTH: 3714
<212> TYPE: DNA
<213> ORGANISM: Artificial Sequence
<220> FEATURE:
<223> OTHER INFORMATION: Synthetic

<400> SEQUENCE: 13

```
ggtaccctag tggtgataaa tgtgggactt ctgagaagtc attcatttta ttctttgtgc    60
cataccagag tacaagctta tgggcgctga tgatgttgtt gattcttcta atcttttgt   120
gatggaaaac ttttcttcgt accacgggac taaacctggt tatgtagatt ccattcaaaa   180
aggtatacaa aagccaaaat ctggtacaca aggaaattat gacgatgatt ggaaagggtt   240
ttatagtacc gacaataaat acgacgctgc gggatactct gtagataatg aaaacccgct   300
ctctggaaaa gctggaggcg tggtcaaagt gacgtatcca ggactgacga aggttctcgc   360
actaaaagtg gataatgccg aaactattaa gaaagagtta ggtttaagtc tcactgaacc   420
gttgatggag caagtcggaa cggaagagtt tatcaaaagg ttcggtgatg gtgcttcgcg   480
tgtagtgctc agccttccct tcgctgaggg gagttctagc gttgaatata ttaataactg   540
ggaacaggcg aaagcgttaa gcgtagaact tgagattaat tttgaaaccc gtggaaaacg   600
tggccaagat gcgatgtatg agtatatggc tcaagcctct agagtcgggg cggccggccg   660
cttcgagcag acatgataag atacattgat gagtttggac aaaccacaac tagaatgcag   720
tgaaaaaaat gctttatttg tgaaatttgt gatgctattg ctttatttgt aaccattata   780
agctgcaata acaagttaa caacaacaat gcattcatt ttatgtttca ggttcagggg    840
gaggtgtggg aggttttta agcaagtaa acctctaca aatgtggtaa atcgataag      900
gatccgtcga ccgatgccct tgagagcctt caacccagtc agctccttcc ggtgggcgcg   960
gggcatgact atcgtcgccg cacttatgac tgtcttcttt atcatgcaac tcgtaggaca  1020
ggtgccggca gcgctcttcc gcttcctcgc tcactgactc gctgcgctcg gtcgttcggc  1080
tgcggcgagc ggtatcagct cactcaaagg cggtaatacg gttatccaca gaatcagggg  1140
ataacgcagg aaagaacatg tgagcaaaag gccagcaaaa ggccaggaac cgtaaaaagg  1200
ccgcgttgct ggcgtttttc cataggctcc gccccctga cgagcatcac aaaaatcgac   1260
gctcaagtca gaggtggcga aacccgacag gactataaag ataccaggcg tttccccctg  1320
```

```
gaagctccct cgtgcgctct cctgttccga ccctgccgct taccggatac ctgtccgcct    1380
ttctcccttc gggaagcgtg gcgctttctc aatgctcacg ctgtaggtat ctcagttcgg    1440
tgtaggtcgt tcgctccaag ctgggctgtg tgcacgaacc ccccgttcag cccgaccgct    1500
gcgccttatc cggtaactat cgtcttgagt ccaacccggt aagacacgac ttatcgccac    1560
tggcagcagc cactggtaac aggattagca gagcgaggta tgtaggcggt gctacagagt    1620
tcttgaagtg gtggcctaac tacggctaca ctagaaggac agtatttggt atctgcgctc    1680
tgctgaagcc agttaccttc ggaaaaagag ttggtagctc ttgatccggc aaacaaacca    1740
ccgctggtag cggtggtttt tttgtttgca agcagcagat tacgcgcaga aaaaaggat     1800 ctcaagaaga tcctttgatc ttttctacgg ggtctgacgc tcagtggaac gaaaactcac    1860
gttaagggat tttggtcatg agattatcaa aaaggatctt cacctagatc cttttaaatt    1920
aaaaatgaag ttttaaatca atctaaagta tatatgagta aacttggtct gacagttacc    1980
aatgcttaat cagtgaggca cctatctcag cgatctgtct atttcgttca tccatagttg    2040
cctgactccc cgtcgtgtag ataactacga tacgggaggg cttaccatct ggccccagtg    2100
ctgcaatgat accgcgagac ccacgctcac cggctccaga tttatcagca ataaaccagc    2160
cagccggaag ggccgagcgc agaagtggtc ctgcaacttt atccgcctcc atccagtcta    2220
ttaattgttg ccgggaagct agagtaagta gttcgccagt taatagtttg cgcaacgttg    2280
ttgccattgc tacaggcatc gtggtgtcac gctcgtcgtt tggtatggct tcattcagct    2340
ccggttccca acgatcaagg cgagttacat gatcccccat gttgtgcaaa aaagcggtta    2400
gctccttcgg tcctccgatc gttgtcagaa gtaagttggc cgcagtgtta tcactcatgg    2460
ttatggcagc actgcataat tctcttactg tcatgccatc cgtaagatgc ttttctgtga    2520
ctggtgagta ctcaaccaag tcattctgag aatagtgtat gcggcgaccg agttgctctt    2580
gcccggcgtc aatacgggat aataccgcgc cacatagcag aactttaaaa gtgctcatca    2640
ttggaaaacg ttcttcgggg cgaaaactct caaggatctt accgctgttg agatccagtt    2700
cgatgtaacc cactcgtgca cccaactgat cttcagcatc ttttactttc accagcgttt    2760
ctgggtgagc aaaaacagga aggcaaaatg ccgcaaaaaa gggaataagg gcgacacgga    2820
aatgttgaat actcatactc ttcctttttc aatattattg aagcatttat cagggttatt    2880
gtctcatgag cggatacata tttgaatgta tttagaaaaa taaacaaata ggggttccgc    2940
gcacatttcc ccgaaaagtg ccacctgacg cgccctgtag cggcgcatta agcgcggcgg    3000
gtgtggtggt tacgcgcagc gtgaccgcta cacttgccag cgccctagcg cccgctcctt    3060
tcgctttctt cccttccttt ctcgccacgt tcgccggctt tccccgtcaa gctctaaatc    3120
gggggctccc tttagggttc cgatttagtg ctttacggca cctcgacccc aaaaaacttg    3180
attagggtga tggttcacgt agtgggccat cgccctgata cggttttt cgcccttga     3240 cgttggagtc cacgttcttt aatagtggac tcttgttcca aactggaaca cactcaacc    3300 ctatctcggt ctattctttt gatttataag ggattttgcc gatttcggcc tattggttaa    3360
aaaatgagct gatttaacaa aaatttaacg cgaattttaa caaaatatta cgtttacaa    3420 tttcccattc gccattcagg ctgcgcaact gttgggaagg gcgatcggtg cgggcctctt    3480
cgctattacg ccagcccaag ctaccatgat aagtaagtaa tattaaggta cgggaggtac    3540
ttggagcggc cgcaataaaa tatctttatt ttcattacat ctgtgtgttg gttttttgtg    3600
tgaatcgata gtactaacat acgctctcca tcaaaacaaa acgaaacaaa acaaactagc    3660
aaaataggct gtccccagtg caagtgcagg tgccagaaca tttctctatc gata          3714
```

<210> SEQ ID NO 14
<211> LENGTH: 31
<212> TYPE: DNA
<213> ORGANISM: Artificial Sequence
<220> FEATURE:
<223> OTHER INFORMATION: Synthetic

<400> SEQUENCE: 14
ggggtaccga aggagctccg agtacataaa t                          31

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
cccaagcttc tactctggta tggcacaaag                            30

<210> SEQ ID NO 16
<211> LENGTH: 70
<212> TYPE: DNA
<213> ORGANISM: Artificial Sequence
<220> FEATURE:
<223> OTHER INFORMATION: Synthetic

<400> SEQUENCE: 16
cctagtggtg ataaatgtgg gacttctgag aagtcattca ttttattctt tgtgccatac    60
cagagtacaa                                                          70

<210> SEQ ID NO 17
<211> LENGTH: 78
<212> TYPE: DNA
<213> ORGANISM: Artificial Sequence
<220> FEATURE:
<223> OTHER INFORMATION: Synthetic

<400> SEQUENCE: 17
tcgaaacatg agaccatacc gtgtttctta ttttacttac tgaagagtct tcaggtgta    60 aatagtggtg atcccatg                                                 78

<210> SEQ ID NO 18
<211> LENGTH: 558
<212> TYPE: DNA
<213> ORGANISM: Artificial Sequence
<220> FEATURE:
<223> OTHER INFORMATION: Synthetic

<400> SEQUENCE: 18
atgggcgctg atgatgttgt tgattcttct aaatcttttg tgatggaaaa ctttcttcg    60 taccacggga ctaaacctgg ttatgtagat tccattcaaa aaggtataca aaagccaaaa   120
tctggtacac aaggaaatta tgacgatgat tggaaagggt tttatagtac cgacaataaa   180
tacgacgctg cgggatactc tgtagataat gaaaacccgc tctctggaaa agctggaggc   240
gtggtcaaag tgacgtatcc aggactgacg aaggttctcg cactaaaagt ggataatgcc   300
gaaactatta agaaagagtt aggtttaagt ctcactgaac cgttgatgga gcaagtcgga   360
acggaagagt ttatcaaaag gttcggtgat ggtgcttcgc gtgtagtgct cagccttccc   420
ttcgctgagg ggagttctag cgttgaatat attaataact gggaacaggc gaaagcgtta   480

```
agcgtagaac ttgagattaa ttttgaaacc cgtggaaaac gtggccaaga tgcgatgtat      540
gagtatatgg ctcaagcc                                                   558

<210> SEQ ID NO 19
<211> LENGTH: 186
<212> TYPE: PRT
<213> ORGANISM: Artificial Sequence
<220> FEATURE:
<223> OTHER INFORMATION: Synthetic

<400> SEQUENCE: 19

Met Gly Ala Asp Asp Val Val Asp Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala
            180                 185

<210> SEQ ID NO 20
<211> LENGTH: 1752
<212> TYPE: DNA
<213> ORGANISM: Artificial Sequence
<220> FEATURE:
<223> OTHER INFORMATION: Synthetic

<400> SEQUENCE: 20
ctagtggtga taaatgtggg acttctgaga agtcattcat tttattcttt gtgccatacc       60
agagtacaag cttggcattc cggtactgtt ggtaaagcca ccatggaaga cgccaaaaac      120
ataaagaaag gcccggcgcc attctatccg ctggaagatg aaccgctgg agagcaactg      180 cataaggcta tgaagagata cgccctggtt cctggaacaa ttgcttttac agatgcacat      240
atcgaggtgg acatcactta cgctgagtac ttcgaaatgt ccgttcggtt ggcagaagct      300
atgaaacgat atgggctgaa tacaaatcac agaatcgtcg tatgcagtga aaactctctt      360
caattcttta tgccggtgtt gggcgcgtta tttatcggag ttgcagttgc gcccgcgaac      420
gacatttata tgaacgtga attgctcaac agtatgggca tttcgcagcc taccgtggtg      480
ttcgtttcca aaaggggtt gcaaaaaatt ttgaacgtgc aaaaaagct cccaatcatc      540 caaaaaatta ttatcatgga ttctaaaacg gattaccagg gatttcagtc gatgtacacg      600
```

```
ttcgtcacat ctcatctacc tcccggtttt aatgaatacg attttgtgcc agagtccttc    660
gatagggaca agacaattgc actgatcatg aactcctctg gatctactgg tctgcctaaa    720
ggtgtcgctc tgcctcatag aactgcctgc gtgagattct cgcatgccag agatcctatt    780
tttggcaatc aaatcattcc ggatactgcg attttaagtg ttgttccatt ccatcacggt    840
tttggaatgt ttactacact cggatatttg atatgtggat ttcgagtcgt cttaatgtat    900
agatttgaag aagagctgtt tctgaggagc cttcaggatt acaagattca aagtgcgctg    960
ctggtgccaa ccctattctc cttcttcgcc aaaagcactc tgattgacaa atacgattta   1020
tctaatttac acgaaattgc ttctggtggc gctcccctct ctaaggaagt cggggaagcg   1080
gttgccaaga ggttccatct gccaggtatc aggcaaggat atgggctcac tgagactaca   1140
tcagctattc tgattacacc cgagggggat gataaaccgg gcgcggtcgg taaagttgtt   1200
ccattttttg aagcgaaggt tgtggatctg gataccggga aaacgctggg cgttaatcaa   1260
agaggcgaac tgtgtgtgag aggtcctatg attatgtccg gttatgtaaa caatccggaa   1320
gcgaccaacg ccttgattga caaggatgga tggctacatt ctggagacat agcttactgg   1380
gacgaagaca acacttcctt catcgttgac cgcctgaagt ctctgattaa gtacaaaggc   1440
tatcaggtgg ctcccgctga attggaatcc atcttgctcc aacacccaa catcttcgac    1500 gcaggtgtcg caggtcttcc cgacgatgac gccggtgaac ttcccgccgc cgttgttgtt   1560
ttggagcacg gaaagacgat gacggaaaaa gagatcgtgg attacgtcgc cagtcaagta   1620
acaaccgcga aaaagttgcg cggaggagtt gtgtttgtgg acgaagtacc gaaaggtctt   1680
accggaaaac tcgacgcaag aaaaatcaga gagatcctca taaaggccaa gaagggcgga   1740
aagatcgccg tg                                                        1752
```

<210> SEQ ID NO 21
<211> LENGTH: 613
<212> TYPE: PRT
<213> ORGANISM: Artificial Sequence
<220> FEATURE:
<223> OTHER INFORMATION: Synthetic

<400> SEQUENCE: 21

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
```

-continued

```
            145                 150                 155                 160
        Met Gln Pro Thr Leu Ala Ile Ser His Ala Gly Val Ser Val Met
                        165                 170                 175
        Ala Gln Thr Gln Pro Arg Arg Glu Lys Arg Trp Ser Glu Trp Ala Ser
                        180                 185                 190
        Gly Lys Val Leu Cys Leu Leu Asp Pro Leu Asp Gly Tyr Asn Tyr
                        195                 200                 205
        Leu Ala Gln Gln Arg Cys Asn Leu Asp Asp Thr Trp Glu Gly Lys Ile
            210                 215                 220
        Tyr Arg Val Leu Ala Gly Asn Pro Ala Lys His Asp Leu Asp Ile Lys
        225                 230                 235                 240
        Pro Thr Val Ile Ser His Arg Leu His Phe Pro Glu Gly Gly Ser Leu
                        245                 250                 255
        Ala Ala Leu Thr Ala His Gln Ala Cys His Leu Pro Leu Glu Thr Phe
                        260                 265                 270
        Thr Arg His Arg Gln Pro Arg Gly Trp Glu Gln Leu Glu Gln Cys Gly
                        275                 280                 285
        Tyr Pro Val Gln Arg Leu Val Ala Leu Tyr Leu Ala Ala Arg Leu Ser
            290                 295                 300
        Trp Asn Gln Val Asp Gln Val Ile Arg Asn Ala Leu Ala Ser Pro Gly
        305                 310                 315                 320
        Ser Gly Gly Asp Leu Gly Glu Ala Ile Arg Glu Gln Pro Glu Gln Ala
                        325                 330                 335
        Arg Leu Ala Leu Thr Leu Ala Ala Ala Glu Ser Glu Arg Phe Val Arg
                        340                 345                 350
        Gln Gly Thr Gly Asn Asp Glu Ala Gly Ala Ala Asn Ala Asp Val Val
                        355                 360                 365
        Ser Leu Thr Cys Pro Val Ala Ala Gly Glu Cys Ala Gly Pro Ala Asp
                        370                 375                 380
        Ser Gly Asp Ala Leu Leu Glu Arg Asn Tyr Pro Thr Gly Ala Glu Phe
        385                 390                 395                 400
        Leu Gly Asp Gly Gly Asp Val Ser Phe Ser Thr Arg Gly Thr Gln Asn
                        405                 410                 415
        Trp Thr Val Glu Arg Leu Leu Gln Ala His Arg Gln Leu Glu Glu Arg
                        420                 425                 430
        Gly Tyr Val Phe Val Gly Tyr His Gly Thr Phe Leu Glu Ala Ala Gln
                        435                 440                 445
        Ser Ile Val Phe Gly Val Arg Ala Arg Ser Gln Asp Leu Asp Ala
            450                 455                 460
        Ile Trp Arg Gly Phe Tyr Ile Ala Gly Asp Pro Ala Leu Ala Tyr Gly
        465                 470                 475                 480
        Tyr Ala Gln Asp Gln Glu Pro Asp Ala Arg Gly Arg Ile Arg Asn Gly
                        485                 490                 495
        Ala Leu Leu Arg Val Tyr Val Pro Arg Ser Ser Leu Pro Gly Phe Tyr
                        500                 505                 510
        Arg Thr Ser Leu Thr Leu Ala Ala Pro Glu Ala Ala Gly Glu Val Glu
                        515                 520                 525
        Arg Leu Ile Gly His Pro Leu Pro Leu Arg Leu Asp Ala Ile Thr Gly
                        530                 535                 540
        Pro Glu Glu Glu Gly Gly Arg Leu Glu Thr Ile Leu Gly Trp Pro Leu
        545                 550                 555                 560
        Ala Glu Arg Thr Val Val Ile Pro Ser Ala Ile Pro Thr Asp Pro Arg
                        565                 570                 575
```

```
Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 22
<211> LENGTH: 353
<212> TYPE: PRT
<213> ORGANISM: Artificial Sequence
<220> FEATURE:
<223> OTHER INFORMATION: Synthetic

<400> SEQUENCE: 22

Ala Ala Ala Ser Gly Gly Pro Glu Gly Gly Ser Leu Ala Ala Leu Thr
1               5                   10                  15

Ala His Gln Ala Cys His Leu Pro Leu Glu Thr Phe Thr Arg His Arg
            20                  25                  30

Gln Pro Arg Gly Trp Glu Gln Leu Glu Gln Cys Gly Tyr Pro Val Gln
        35                  40                  45

Arg Leu Val Ala Leu Tyr Leu Ala Ala Arg Leu Ser Trp Asn Gln Val
50                  55                  60

Asp Gln Val Ile Arg Asn Ala Leu Ala Ser Pro Gly Ser Gly Gly Asp
65                  70                  75                  80

Leu Gly Glu Ala Ile Arg Glu Gln Pro Glu Gln Ala Arg Leu Ala Leu
                85                  90                  95

Thr Leu Ala Ala Ala Glu Ser Glu Arg Phe Val Arg Gln Gly Thr Gly
            100                 105                 110

Asn Asp Glu Ala Gly Ala Ala Asn Gly Pro Ala Asp Ser Gly Asp Ala
        115                 120                 125

Leu Leu Glu Arg Asn Tyr Pro Thr Gly Ala Glu Phe Leu Gly Asp Gly
    130                 135                 140

Gly Asp Val Ser Phe Ser Thr Arg Gly Thr Gln Asn Trp Thr Val Glu
145                 150                 155                 160

Arg Leu Leu Gln Ala His Arg Gln Leu Glu Glu Arg Gly Tyr Val Phe
                165                 170                 175

Val Gly Tyr His Gly Thr Phe Leu Glu Ala Ala Gln Ser Ile Val Phe
            180                 185                 190

Gly Gly Val Arg Ala Arg Ser Gln Asp Leu Asp Ala Ile Trp Arg Gly
        195                 200                 205

Phe Tyr Ile Ala Gly Asp Pro Ala Leu Ala Tyr Gly Tyr Ala Gln Asp
    210                 215                 220

Gln Glu Pro Asp Ala Arg Gly Arg Ile Arg Asn Gly Ala Leu Leu Arg
225                 230                 235                 240

Val Tyr Val Pro Arg Ser Ser Leu Pro Gly Phe Tyr Arg Thr Ser Leu
                245                 250                 255

Thr Leu Ala Ala Pro Glu Ala Ala Gly Glu Val Glu Arg Leu Ile Gly
            260                 265                 270

His Pro Leu Pro Leu Arg Leu Asp Ala Ile Thr Gly Pro Glu Glu Glu
        275                 280                 285

Gly Gly Arg Leu Glu Thr Ile Leu Gly Trp Pro Leu Ala Glu Arg Thr
    290                 295                 300

Val Val Ile Pro Ser Ala Ile Pro Thr Asp Pro Arg Asn Val Gly Gly
305                 310                 315                 320
```

```
Asp Leu Asp Pro Ser Ser Ile Pro Asp Lys Glu Gln Ala Ile Ser Ala
            325                 330                 335

Leu Pro Asp Tyr Ala Ser Gln Pro Gly Lys Pro Pro Arg Lys Asp Glu
            340                 345                 350

Leu

<210> SEQ ID NO 23
<211> LENGTH: 334
<212> TYPE: PRT
<213> ORGANISM: Artificial Sequence
<220> FEATURE:
<223> OTHER INFORMATION: Synthetic

<400> SEQUENCE: 23

Met Trp Glu Gln Leu Glu Gln Ser Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg Asn Ala Leu Ala Ser Pro Gly Ser Gly Gly Asp Leu Gly Glu
        35                  40                  45

Ala Ile Arg Glu Gln Pro Glu Gln Ala Arg Leu Ala Leu Thr Leu Ala
    50                  55                  60

Ala Ala Glu Ser Glu Arg Phe Val Arg Gln Gly Thr Gly Asn Asp Glu
65                  70                  75                  80

Ala Gly Ala Ala Asn Ala Asp Val Val Ser Leu Thr Cys Pro Val Ala
                85                  90                  95

Ala Gly Glu Cys Ala Gly Pro Ala Asp Ser Gly Asp Ala Leu Leu Glu
            100                 105                 110

Arg Asn Tyr Pro Thr Gly Ala Glu Phe Leu Gly Asp Gly Gly Asp Val
        115                 120                 125

Ser Phe Ser Thr Arg Gly Thr Gln Asn Trp Thr Val Glu Arg Leu Leu
130                 135                 140

Gln Ala His Arg Gln Leu Glu Glu Arg Gly Tyr Val Phe Val Gly Tyr
145                 150                 155                 160

His Gly Thr Phe Leu Glu Ala Ala Gln Ser Ile Val Phe Gly Gly Val
                165                 170                 175

Arg Ala Arg Ser Gln Asp Leu Asp Ala Ile Trp Arg Gly Phe Tyr Ile
            180                 185                 190

Ala Gly Asp Pro Ala Leu Ala Tyr Gly Tyr Ala Gln Asp Gln Glu Pro
        195                 200                 205

Asp Ala Arg Gly Arg Ile Arg Asn Gly Ala Leu Leu Arg Val Tyr Val
    210                 215                 220

Pro Arg Ser Ser Leu Pro Gly Phe Tyr Arg Thr Ser Leu Thr Leu Ala
225                 230                 235                 240

Ala Pro Glu Ala Ala Gly Glu Val Glu Arg Leu Ile Gly His Pro Leu
                245                 250                 255

Pro Leu Arg Leu Asp Ala Ile Thr Gly Pro Glu Glu Gly Gly Arg
            260                 265                 270

Leu Glu Thr Ile Leu Gly Trp Pro Leu Ala Glu Arg Thr Val Val Ile
        275                 280                 285

Pro Ser Ala Ile Pro Thr Asp Pro Arg Asn Val Gly Gly Asp Leu Asp
    290                 295                 300

Pro Ser Ser Ile Pro Asp Lys Glu Gln Ala Ile Ser Ala Leu Pro Asp
305                 310                 315                 320
```

Tyr Ala Ser Gln Pro Gly Lys Pro Arg Glu Asp Leu Lys
            325                 330

<210> SEQ ID NO 24
<211> LENGTH: 361
<212> TYPE: PRT
<213> ORGANISM: Artificial Sequence
<220> FEATURE:
<223> OTHER INFORMATION: Synthetic

<400> SEQUENCE: 24

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Asp Leu Gly Glu Ala Ile Arg Glu Gln
65                  70                  75                  80

Pro Glu Gln Ala Arg Leu Ala Leu Thr Leu Ala Ala Glu Ser Glu
            85                  90                  95

Arg Phe Val Arg Gln Gly Thr Gly Asn Asp Glu Ala Gly Ala Ala Asn
        100                 105                 110

Ala Asp Val Val Ser Leu Thr Cys Pro Val Ala Ala Gly Glu Cys Ala
    115                 120                 125

Gly Pro Ala Asp Ser Gly Asp Ala Leu Leu Glu Arg Asn Tyr Pro Thr
130                 135                 140

Gly Ala Glu Phe Leu Gly Asp Gly Gly Asp Val Ser Phe Ser Thr Arg
145                 150                 155                 160

Gly Thr Gln Asn Trp Thr Val Glu Arg Leu Leu Gln Ala His Arg Gln
            165                 170                 175

Leu Glu Glu Arg Gly Tyr Val Phe Val Gly Tyr His Gly Thr Phe Leu
        180                 185                 190

Glu Ala Ala Gln Ser Ile Val Phe Gly Val Arg Ala Arg Ser Gln
    195                 200                 205

Asp Leu Asp Ala Ile Trp Arg Gly Phe Tyr Ile Ala Gly Asp Pro Ala
210                 215                 220

Leu Ala Tyr Gly Tyr Ala Gln Asp Gln Glu Pro Asp Ala Arg Gly Arg
225                 230                 235                 240

Ile Arg Asn Gly Ala Leu Leu Arg Val Tyr Val Pro Arg Ser Ser Leu
            245                 250                 255

Pro Gly Phe Tyr Arg Thr Ser Leu Thr Leu Ala Ala Pro Glu Ala Ala
        260                 265                 270

Gly Glu Val Glu Arg Leu Ile Gly His Pro Leu Pro Leu Arg Leu Asp
    275                 280                 285

Ala Ile Thr Gly Pro Glu Glu Gly Gly Arg Leu Glu Thr Ile Leu
290                 295                 300

Gly Trp Pro Leu Ala Glu Arg Thr Val Val Ile Pro Ser Ala Ile Pro
305                 310                 315                 320

Thr Asp Pro Arg Asn Val Gly Gly Asp Leu Asp Pro Ser Ser Ile Pro
            325                 330                 335

Asp Lys Glu Gln Ala Ile Ser Ala Leu Pro Asp Tyr Ala Ser Gln Pro
        340                 345                 350

Gly Lys Pro Pro Arg Glu Asp Leu Lys
        355                 360

<210> SEQ ID NO 25
<211> LENGTH: 720
<212> TYPE: DNA
<213> ORGANISM: Artificial Sequence
<220> FEATURE:
<223> OTHER INFORMATION: Synthetic

<400> SEQUENCE: 25

```
atggctagca aaggagaaga acttttcact ggagttgtcc caattcttgt tgaattagat      60
ggtgatgtta atgggcacaa attttctgtc agtggagagg gtgaaggtga tgctacatac     120
ggaaagctta cccttaaatt tatttgcact actggaaaac tacctgttcc atggccaaca     180
cttgtcacta ctttctctta tggtgttcaa tgcttttccc gttatccgga tcatatgaaa     240
cggcatgact tttcaagag tgccatgccc gaaggttatg tacaggaacg cactatatct     300
ttcaaagatg acgggaacta caagacgcgt gctgaagtca agtttgaagg tgataccctt     360
gttaatcgta tcgagttaaa aggtattgat tttaagaag atggaaacat tctcggacac     420
aaactcgagt acaactataa ctcacacaat gtatacatca cggcagacaa acaaaagaat     480
ggaatcaaag ctaacttcaa aattcgccac aacattgaag atggatccgt tcaactagca     540
gaccattatc aacaaaatac tccaattggc gatggccctg tccttttacc agacaaccat     600
tacctgtcga cacaatctgc cctttcgaaa gatcccaacg aaaagcgtga ccacatggtc     660
cttcttgagt ttgtaactgc tgctgggatt acacatggca tggatgagct ctacaaataa     720
```

<210> SEQ ID NO 26
<211> LENGTH: 3530
<212> TYPE: DNA
<213> ORGANISM: Artificial Sequence
<220> FEATURE:
<223> OTHER INFORMATION: Synthetic

<400> SEQUENCE: 26

```
cattttattc tttgtgccat accagagtac agtatcagct gagctgacct tactctgagg      60
actaactctt ttgctggaag cggtttctga tttacagctc ttggtttctc ccagacatgt     120
tggtgggaga gatttggtt tttaaggggt tgttagatgg agtaaatttt ctttttttt     180
tttttttttt ttaactaaaa aggggtcaca gaatttcagc agttctctga tttttatatt     240
ttattcctct tcctatccaa tccctgcctt ttgagtccag gtggtaagta catttcttt     300
aacgtttttc ctgcttttct tcccaaatgt gtctttttct ttgggctact gtaccctgct     360
tccagtgctg tccccggcat aggtccatct ctgcagaagc catttcagga gtacctggag     420
gctcaacggc agaagcttca ccacaaaagc gaaatgggca caccacaggt aagactttaa     480
tccggttttct ctcccctct gggaagtttc gggctgaaat tacattcaca gctctcactc     540
acattttag gcaaataagt gaagttggtt tgccagtgtt ccttgacaga agttgagcgt     600
ctgtgtatgc tctactggga aatttgtctt tgtcttagac tagaaagtgt aacttctgta     660
catcttctcc taaaacaag ggtagagcca atgaaagta atggttctgt tacatagaat     720
gagttgttgc cttgatctta aatgatgtat tggtagatat acttcccaag tggattaaaa     780
agttaaaact tacagcataa caaagtatta gacttactga ggtgacttga atatctcctt     840
ttgattttca ctctattttt cttttcaccc atgggaaaat gataattttt taataaacca     900
aggctcttac catagctgaa ctttaaaact tagactgtct tttctgtaaa cgattctgag     960
```

-continued

```
gcaaagggaa atgactagaa gaggatgagt aaacaataac ctgaaatggg aaactcgagg    1020
gaagcacagg ttttttttgt tttgttttgt ttggttcgtt ttttgttctt tggggttttt    1080
ttgagacaga atttcgctct cgttgcccaa gttggagtgc aatggcgcga tcttggctca    1140
ctgcaacctc cgcctcccgg gttcaagcga ttctcctgcc tcagcctccc aagtagctgt    1200
gattccaggc acgtgccacc acaccagcta attttttgta ttttaataga aacagggttt    1260
caccgtgtta gccaggctgg tctcaaactg acctcagatg atccgcccgc cttggcctcc    1320
caaagtgctg ggattacaga tgtgagccac cgcgcccggc cagagcactg ttttttttaa    1380
tggccttgca ctcttcttat ggacctttgc tgccctcagt tgaccaaaca tgacatcaga    1440
aacagataca tttgtgtgtt ttaaaaacag ctcctaatac tggaacaaaa atatttaact    1500
gtcttgacaa tactcatgag tatctgcatg gcgacttcag agttgagttt aatcaaagag    1560
tttattctta ggtcctagta aagagctaaa cctcacactc atcccattct aaactatgtg    1620
attcaacact gattttacat ccaacaaagt gaaatcttga tagttgggtg taaaaaggag    1680
agtaatggag atttcagagt agttggggtt gcttactttt cattttttaat tctttaggtt    1740 ttgtaagtta cacacttcaa gcattataga tgatcctctt tttactactg aactaatgaa    1800 gccttttttca ttgcattgtt ctgcatttat ttctacaggg agaaaactgg ttgtcctgga    1860
tgtttgaaaa gttggtcgtt gtcatggtgt gttacttcat cctatctatc attaactcca    1920
tggcacaaag ttatgccaaa cgaatccagc agcggttgaa ctcagaggag aaaactaaat    1980
aagtagagaa agttttaaac tgcagaaatt ggagtggatg ggttctgcct taaattggga    2040
ggactccaag ccgggaagga aaattccctt ttccaacctg tatcatttttt acaacttttt    2100 tcctgaaagc agtttagtcc atactttgca ctgacatact ttttccttct gtgctaaggt    2160
aaggtatcca ccctcgatgc aatccacctt gtgttttctt agggtggaat gtgatgttca    2220
gcagcaaact tgcaacagac tggccttctg tttgttactt tcaaaaggcc cacatgatac    2280
aattagagaa ttcccaccgc acaaaaaaag ttcctaagta tgttaaatat gtcaagcttt    2340
ttaggcttgt cacaaatgat tgcttgtttt cctaagtcat caaaatgtat ataaattatc    2400
tagattggat aacagtcttg catgtttatc atgttacaat ttaatattcc atcctgccca    2460
acccttcctc tcccatcctc aaaaaagggc cattttatga tgcattgcac accctctggg    2520
gaaattgatc tttaaatttt gagacagtat aaggaaaatc tggttggtgt cttacaagtg    2580
agctgacacc atttttttatt ctgtgtattt agaatgaagt cttgaaaaaa actttataaa    2640
gactctttaa tcattccaaa attgtgtccg ttttcttgag cgttttgatt ttttactttt    2700
agcttatacc agctgaatgg cagccttgcc taatccacct acaacaagaa tttcttaagc    2760
tttcttttat ttgcatgaga gagccactac caaggcatgt tttgttatgc tgaaactggg    2820
ctgctgcata ctgctaaatg gcacctctgg gattggccta cctggggatt tcttggtttg    2880
tgaaaacagg agaggagaaa tatctcatac aagtgaaagg atactggaga gagaaattac    2940
ccatttctaa aaaaaaacca cactctgtcg tatctgtgtt aatgtttttct agcatgtact    3000 ctggtttcaa cagacacaaa tttatatgtt aacccagttt tcttgccgtt ctgtaagtgt    3060
ttattcttag tgtgactttt ttccattggg atgttttga ttgaacttgt tcatttttgtt    3120 ttgcttggga ggaaaataaa caatttact ttttttcctttt aggagcatta tgagcattat    3180
gtcagaatag aatagaattg gggttcgatc ttaacaggcc agaaatgcct gggttttttt    3240
ggtttgtttt tgtttttgtt tttttatcaa atcctgcctg actgtctgct tgttttgcct    3300
accatcgtga catctccatg gctgtaccac cttgtcgggt agcttatcag actgatgttg    3360
```

```
actgttgaat ctcatggcaa caccagtcga tgggctgtct gacattttgg tatctttcat    3420
ctgaccatcc atatccaatg ttctcattta acattaccc agcatcattg tttataatca     3480
gaaactctgg tccttctgtc tggtggcact tagagtcttt tgtgccataa                3530

<210> SEQ ID NO 27
<211> LENGTH: 1008
<212> TYPE: DNA
<213> ORGANISM: Artificial Sequence
<220> FEATURE:
<223> OTHER INFORMATION: Synthetic

<400> SEQUENCE: 27
ttaattggtt caaaccagtt cttacaggaa ctagtggtga taaatgtggg acttctgaga      60
agtcattcat tttattcttt gtgccatacc agagtacagt atcagctgag ctgaccttac     120
tctgaggact aactcttttg ctggaagcgg tttctgattt acagctcttg gtttctccca    180
gacatgttgg tgggagagat tttggttttt aaggggttgt tagatggagt aaattttctt    240
tttttttttt tttttttta actaaaaagg ggtcacagaa tttcagcagt tctctgattt     300
ttatatttta ttcctcttcc tatccaatcc ctgccttttg agtccaggtg gtaagtacat    360
tttctttaac gttttttcctg cttttcttcc caaatgtgtc ttttttctttg ggctactgta  420 ccctgcttcc agtgctgtcc ccggcatagg tccatctctg cagaagccat tcaggagta    480 cctggaggct caacggcaga agcttcacca caaaagcgaa atgggcacac cacaggtaag    540
actttaatcc ggtttcttct cccctctggg aagtttcggg ctgaaattac attcacagct    600
ctcactcaca tttttaggca aataagtgaa gttggtttgc cagtgttcct tgacagaagt    660
tgagcgtctg tgtatgctct actgggaaat ttgtctttgt cttagactag aaagtgtaac   720
ttctgtacat cttctcctaa aaacaagggt agagccaatg gaaagtaatg gttctgttac    780
atagaatgag ttgttgcctt gatcttaaat gatgtattgg tagatatact tcccaagtgg   840
attaaaaagt taaaacttac agcataacaa agtattagac ttactgaggt gacttgaata   900
tctccttttg atttcactc tattttttctt ttcacccatg ggaaaatgat aattttttaa    960
taaaccaagg ctcttaccat agctgaactt taaaacttag actgtctt                1008

<210> SEQ ID NO 28
<211> LENGTH: 3705
<212> TYPE: DNA
<213> ORGANISM: Artificial Sequence
<220> FEATURE:
<223> OTHER INFORMATION: Synthetic

<400> SEQUENCE: 28
agatctgcgc agcaccatgg cctgaaataa cctctgaaag aggaacttgg ttaggtacct     60
tctgaggcgg aaagaaccag ctgtggaatg tgtgtcagtt agggtgtgga aagtccccag    120
gctccccagc aggcagaagt atgcaaagca tgcatctcaa ttagtcagca accaggtgtg   180
gaaagtcccc aggctcccca gcaggcagaa gtatgcaaag catgcatctc aattagtcag    240
caaccatagt cccgcccta actccgccca tcccgcccct aactccgccc agttccgccc    300
attctccgcc ccatggctga ctaatttttt ttatttatgc agaggccgag gccgcctcgg   360
cctctgagct attccagaag tagtgaggag gctttttggg aggcctaggc ttttgcaaaa    420
agcttgattc ttctgacaca acagtctcga acttaagctg cagaagttgg tcgtgaggca   480
ctgggcaggt aagtatcaag gttacaagac aggtttaagg agaccaatag aaactgggct    540
```

```
tgtcgagaca gagaagactc ttgcgtttct gataggcacc tattggtctt actgacatcc      600
actttgcctt tctctccaca ggtgtccact cccagttcaa ttacagctct taaggctaga      660
gtacttaata cgactcacta taggctagcc accatgactt cgaaagttta tgatccagaa      720
caaaggaaac ggatgataac tggtccgcag tggtgggcca gatgtaaaca aatgaatgtt      780
cttgattcat ttattaatta ttatgattca gaaaaacatg cagaaaatgc tgttatttt       840 ttacatggta acgcggcctc ttcttattta tggcgacatg ttgtgccaca tattgagcca      900
gtagcgcggt gtattatacc agaccttatt ggtatgggca aatcaggcaa atctggtaat      960
ggttcttata ggttacttga tcattacaaa tatcttactg catggtttga acttcttaat     1020
ttaccaaaga agatcatttt tgtcggccat gattggggtg cttgtttggc atttcattat     1080
agctatgagc atcaagataa gatcaaagca atagttcacg ctgaaagtgt agtagatgtg     1140
attgaatcat gggatgaatg gcctgatatt gaagaagata ttgcgttgat caaatctgaa     1200
gaaggagaaa aaatggtttt ggagaataac ttcttcgtgg aaaccatgtt gccatcaaaa     1260
atcatgagaa agttagaacc agaagaattt gcagcatatc ttgaaccatt caaagagaaa     1320
ggtgaagttc gtcgtccaac attatcatgg cctcgtgaaa tcccgttagt aaaaggtggt     1380
aaacctgacg ttgtacaaat tgttaggaat tataatgctt atctacgtgc aagtgatgat     1440
ttaccaaaaa tgtttattga atcggaccca ggattctttt ccaatgctat tgttgaaggt     1500
gccaagaagt ttcctaatac tgaatttgtc aaagtaaaag gtcttcattt ttcgcaagaa     1560
gatgcacctg atgaaatggg aaaatatatc aaatcgttcg ttgagcgagt tctcaaaaat     1620
gaacaataat tctagagcgg ccgcttcgag cagacatgat aagatacatt gatgagtttg     1680
gacaaaccac aactagaatg cagtgaaaaa aatgctttat tgtgaaaatt tgtgatgcta     1740
ttgctttatt tgtaaccatt ataagctgca ataaacaagt taacaacaac aattgcattc     1800
attttatgtt tcaggttcag ggggaggtgt gggaggtttt ttaaagcaag taaaacctct     1860
acaaatgtgg taaaatcgat aaggatccag gtggcacttt tcggggaaat gtgcgcggaa     1920
cccctatttg tttattttc taaatacatt caaatatgta tccgctcatg agacaataac     1980
cctgataaat gcttcaataa tattgaaaaa ggaagagtat gagtattcaa catttccgtg     2040
tcgcccttat tccctttttt gcggcatttt gccttcctgt ttttgctcac ccagaaacgc     2100
tggtgaaagt aaaagatgct gaagatcagt tgggtgcacg agtgggttac atcgaactgg     2160
atctcaacag cggtaagatc cttgagagtt ttcgccccga agaacgtttt ccaatgatga     2220 gcactttaa agttctgcta tgtggcgcgg tattatcccg tattgacgcc gggcaagagc     2280
aactcggtcg ccgcatacac tattctcaga atgacttggt tgagtactca ccagtcacag     2340
aaaagcatct tacgggatggc atgacagtaa gagaattatg cagtgctgcc ataaccatga     2400
gtgataacac tgcggccaac ttacttctga caacgatcgg aggaccgaag gagctaaccg     2460
cttttttgca caacatgggg gatcatgtaa ctcgccttga tcgttgggaa ccggagctga     2520
atgaagccat accaaacgac gagcgtgaca ccacgatgcc tgtagcaatg gcaacaacgt     2580
tgcgcaaact attaactggc gaactactta ctctagcttc ccggcaacaa ttaatagact     2640
ggatggaggc ggataaagtt gcaggaccac ttctgcgctc ggcccttccg gctggctggt     2700
ttattgctga taaatctgga gccggtgagc gtgggtctcg cggtatcatt gcagcactgg     2760
ggccagatgg taagccctcc cgtatcgtag ttatctacac gacggggagt caggcaacta     2820
tggatgaacg aaatagacag atcgctgaga taggtgcctc actgattaag cattggtaac     2880
tgtcagacca agtttactca tatatacttt agattgattt aaaacttcat ttttaattta     2940
```

| | |
|---|---:|
| aaaggatcta ggtgaagatc cttttttgata atctcatgac caaaatccct taacgtgagt | 3000 |
| tttcgttcca ctgagcgtca gacccccgtag aaaagatcaa aggatcttct tgagatcctt | 3060 |
| ttttttctgcg cgtaatctgc tgcttgcaaa caaaaaaacc accgctacca gcggtggttt | 3120 |
| gtttgccgga tcaagagcta ccaactcttt ttccgaaggt aactggcttc agcagagcgc | 3180 |
| agataccaaa tactgttctt ctagtgtagc cgtagttagg ccaccacttc aagaactctg | 3240 |
| tagcaccgcc tacatacctc gctctgctaa tcctgttacc agtggctgct gccagtggcg | 3300 |
| ataagtcgtg tcttaccggg ttggactcaa gacgatagtt accggataag gcgcagcggt | 3360 |
| cgggctgaac ggggggttcg tgcacacagc ccagcttgga gcgaacgacc tacaccgaac | 3420 |
| tgagatacct acagcgtgag ctatgagaaa gcgccacgct tcccgaaggg agaaaggcgg | 3480 |
| acaggtatcc ggtaagcggc agggtcggaa caggagagcg cacgagggag cttccagggg | 3540 |
| gaaacgcctg gtatctttat agtcctgtcg ggtttcgcca cctctgactt gagcgtcgat | 3600 |
| ttttgtgatg ctcgtcaggg gggcggagcc tatggaaaaa cgccagcaac gcggcctttt | 3660 |
| tacggttcct ggccttttgc tggccttttg ctcacatggc tcgac | 3705 |

<210> SEQ ID NO 29
<211> LENGTH: 661
<212> TYPE: DNA
<213> ORGANISM: Artificial Sequence
<220> FEATURE:
<223> OTHER INFORMATION: Synthetic

<400> SEQUENCE: 29

| | |
|---|---:|
| ctagtggtga taaatgtggg acttctgaga agtcattcat tttattcttt gtgccatacc | 60 |
| agagtacaag cttatggccc cgcacgcca ggagggcagc tccccggagc ccgtagaggg | 120 |
| cctggcccgc gacggcccgc gccccttccc gctcggccgc ctggtgccct cggcagtgtc | 180 |
| ctgcggcctc tgcgagcccg gcctggctgc cgccccgcc gccccaccc tgctgccccgc | 240 |
| tgcctacctc tgcgccccca ccgccccacc cgccgtcacc gccgccctgg ggggttcccg | 300 |
| ctggcctggg ggtccccgca gccggccccg aggcccgcgc ccggacggtc ctcagccctc | 360 |
| gctctcgctg gcggagcagc acctggagtc gcccgtgccc agcgccccgg gggctctggc | 420 |
| gggcggtccc acccaggcgg ccccgggagt ccgcggggag gaggaacagt gggcccggga | 480 |
| gatcggggcc cagctgcggc ggatggcgga cgacctcaac gcacagtacg agcggcggag | 540 |
| acaagaggag cagcagcggc accgccccctc accctggagg gtcctgtaca atctcatcat | 600 |
| gggactcctg cccttaccca ggggccacag agcccccgag atggagccca attagtctag | 660 |
| a | 661 |

<210> SEQ ID NO 30
<211> LENGTH: 3738
<212> TYPE: DNA
<213> ORGANISM: Artificial Sequence
<220> FEATURE:
<223> OTHER INFORMATION: Synthetic

<400> SEQUENCE: 30

| | |
|---|---:|
| ggtaccctag tggtgataaa tgtgggactt ctgagaagtc attcatttta ttctttgtgc | 60 |
| cataccagag tacaagctta tggcccgcgc acgccaggag ggcagctccc cggagcccgt | 120 |
| agagggcctg gccgcgacg gcccgcgccc cttcccgctc ggccgcctgg tgccctcggc | 180 |
| agtgtcctgc ggcctctgcg agcccggcct ggctgccgcc ccgccgcccc caccctgct | 240 |

```
gcccgctgcc tacctctgcg cccccaccgc cccacccgcc gtcaccgccg ccctgggggg     300
ttcccgctgg cctggggggtc cccgcagccg gccccgaggc ccgcgcccgg acggtcctca    360
gccctcgctc tcgctggcgg agcagcacct ggagtcgccc gtgcccagcg ccccgggggc    420
tctggcgggg gtcccacccc aggcggcccc gggagtccgc ggggaggagg aacagtgggc    480
ccgggagatc ggggcccagc tgcggcggat ggcggacgac ctcaacgcac agtacgagcg    540
gcggagacaa gaggagcagc agcggcaccg cccctcaccc tggagggtcc tgtacaatct    600
catcatggga ctcctgccct tacccagggg ccacagagcc cccgagatgg agcccaatta    660
gtctagagtc ggggcggccg gccgcttcga gcagacatga aagatacat tgatgagttt     720 ggacaaacca caactagaat gcagtgaaaa aaatgcttta tttgtgaaat tgtgatgct     780 attgctttat ttgtaaccat tataagctgc aataaacaag ttaacaacaa caattgcatt    840
cattttatgt ttcaggttca gggggaggtg tgggaggttt tttaaagcaa gtaaaacctc    900
tacaaatgtg gtaaaatcga taaggatccg tcgaccgatg cccttgagag ccttcaaccc    960
agtcagctcc ttccggtggg cgcggggcat gactatcgtc gccgcactta tgactgtctt   1020
ctttatcatg caactcgtag acaggtgccg gcagcgctc ttccgcttcc tcgctcactg     1080
actcgctgcg ctcggtcgtt cggctgcggc gagcggtatc agctcactca aaggcggtaa   1140
tacggttatc cacagaatca ggggataacg caggaaagaa catgtgagca aaaggccagc    1200
aaaaggccag gaaccgtaaa aaggccgcgt tgctggcgtt ttttccatagg ctccgcccc    1260 ctgacgagca tcacaaaaat cgacgctcaa gtcagaggtg cgaaacccg acaggactat    1320 aaagatacca ggcgtttccc cctggaagct ccctcgtgcg ctctcctgtt ccgaccctgc    1380
cgcttaccgg atacctgtcc gcctttctcc cttcgggaag cgtggcgctt tctcaatgct    1440
cacgctgtag gtatctcagt tcggtgtagg tcgttcgctc caagctgggc tgtgtgcacg    1500
aaccccccgt tcagcccgac cgctgcgcct tatccggtaa ctatcgtctt gagtccaacc    1560
cggtaagaca cgacttatcg ccactggcag cagccactgg taacaggatt agcagagcga    1620
ggtatgtagg cggtgctaca gagttcttga agtggtggcc taactacggc tacactagaa    1680
ggacagtatt tggtatctgc gctctgctga agccagttac cttcggaaaa agagttggta    1740
gctcttgatc cggcaaacaa accaccgctg gtagcggtgg ttttttttgtt tgcaagcagc    1800 agattacgcg cagaaaaaaa ggatctcaag aagatccttt gatctttct acggggtctg    1860 acgctcagtg gaacgaaaac tcacgttaag ggattttggt catgagatta tcaaaaagga    1920
tcttcaccta gatccttta aattaaaaat gaagttttaa atcaatctaa agtatatatg    1980
agtaaacttg gtctgacagt taccaatgct taatcagtga ggcacctatc tcagcgatct    2040
gtctatttcg ttcatccata gttgcctgac tccccgtcgt gtagataact acgatacggg    2100
agggcttacc atctggcccc agtgctgcaa tgataccgcg agacccacgc tcaccggctc    2160
cagatttatc agcaataaac cagccagccg gaagggccga gcgcagaagt ggtcctgcaa    2220
ctttatccgc ctccatccag tctattaatt gttgccggga agctagagta agtagttcgc    2280
cagttaatag tttgcgcaac gttgttgcca ttgctacagg catcgtggtg tcacgctcgt    2340
cgtttggtat ggcttcattc agctccggtt cccaacgatc aaggcgagtt acatgatccc    2400
ccatgttgtg caaaaaagcg gttagctcct tcggtcctcc gatcgttgtc agaagtaagt    2460
tggccgcagt gttatcactc atggttatgg cagcactgca taattctctt actgtcatgc    2520
catccgtaag atgcttttct gtgactggtg agtactcaac caagtcattc tgagaatagt    2580
gtatgcggcg accgagttgc tcttgcccgg cgtcaatacg ggataatacc gcgccacata    2640
```

```
gcagaacttt aaaagtgctc atcattggaa aacgttcttc ggggcgaaaa ctctcaagga    2700
tcttaccgct gttgagatcc agttcgatgt aacccactcg tgcacccaac tgatcttcag    2760
catcttttac tttcaccagc gtttctgggt gagcaaaaac aggaaggcaa aatgccgcaa    2820
aaaagggaat aagggcgaca cggaaatgtt gaatactcat actcttcctt tttcaatatt    2880
attgaagcat ttatcagggt tattgtctca tgagcggata catatttgaa tgtatttaga    2940
aaaataaaca aataggggtt ccgcgcacat ttccccgaaa agtgccacct gacgcgccct    3000
gtagcggcgc attaagcgcg gcgggtgtgg tggttacgcg cagcgtgacc gctacacttg    3060
ccagcgccct agcgcccgct cctttcgctt tcttcccttc ctttctcgcc acgttcgccg    3120
gctttccccg tcaagctcta aatcgggggc tccctttagg gttccgattt agtgctttac    3180
ggcacctcga ccccaaaaaa cttgattagg gtgatggttc acgtagtggg ccatcgccct    3240
gatagacggt ttttcgccct tgacgttgg agtccacgtt ctttaatagt ggactcttgt    3300
tccaaactgg aacaacactc aaccctatct cggtctattc ttttgattta taagggattt    3360
tgccgatttc ggcctattgg ttaaaaaatg agctgattta acaaaaattt aacgcgaatt    3420
ttaacaaaat attaacgttt acaatttccc attcgccatt caggctgcgc aactgttggg    3480
aagggcgatc ggtgcgggcc tcttcgctat tacgccagcc caagctacca tgataagtaa    3540
gtaatattaa ggtacgggag gtacttggag cggccgcaat aaaatatctt tattttcatt    3600
acatctgtgt gttggttttt tgtgtgaatc gatagtacta acatacgctc tccatcaaaa    3660
caaaacgaaa caaaacaaac tagcaaaata ggctgtcccc agtgcaagtg caggtgccag    3720
aacatttctc tatcgata                                                 3738
```